(12) United States Patent
Hlasta et al.

(10) Patent No.: US 6,458,771 B1
(45) Date of Patent: Oct. 1, 2002

(54) KETOLIDE ANTIBACTERIALS

(75) Inventors: Dennis J. Hlasta, Doylestown, PA (US); Todd C. Henninger, Neshanic Station, NJ (US); Eugene B. Grant, Edison, NJ (US); Chaitin Khosla, Palo Alto, CA (US); Daniel T. W. Chu, Santa Clara, CA (US)

(73) Assignees: Ortho-McNeil Pharmaceutical, Inc., Raritan, NJ (US); Kosan Biosciences, Inc., Raritan, NJ (US)

(*) Notice: Subject to any disclaimer, the term of this patent is extended or adjusted under 35 U.S.C. 154(b) by 0 days.

(21) Appl. No.: 09/548,584

(22) Filed: Apr. 13, 2000

Related U.S. Application Data

(60) Provisional application No. 60/131,383, filed on Apr. 28, 1999, provisional application No. 60/172,159, filed on Dec. 17, 1999, provisional application No. 60/129,729, filed on Apr. 16, 1999, provisional application No. 60/172,154, filed on Dec. 17, 1999, and provisional application No. 60/140,175, filed on Jun. 18, 1999.

(51) Int. Cl.$^7$ .................. A61K 31/70; C07H 17/08
(52) U.S. Cl. .................................. 514/29; 536/7.4
(58) Field of Search ............................ 536/7.5; 574/29

(56) References Cited

U.S. PATENT DOCUMENTS

| | | |
|---|---|---|
| 4,742,049 A | 5/1988 | Baker et al. |
| 4,826,820 A | 5/1989 | Brain |
| 4,874,748 A | 10/1989 | Katz et al. |
| 4,935,340 A | 6/1990 | Baltz et al. |
| 5,081,023 A | 1/1992 | Yaginuma et al. |
| 5,087,563 A | 2/1992 | Beremand et al. |
| 5,110,728 A | 5/1992 | Kridl et al. |
| 5,141,926 A | 8/1992 | Weber et al. |
| 5,635,485 A | 6/1997 | Agouridas et al. |
| 5,656,607 A | 8/1997 | Agouridas et al. |
| 5,672,491 A | 9/1997 | Khosla et al. |
| 5,747,467 A | 5/1998 | Agouridas et al. |
| 5,760,233 A | 6/1998 | Agouridas et al. |
| 5,770,579 A | 6/1998 | Agouridas et al. |
| 5,824,513 A | 10/1998 | Katz et al. |
| 5,866,549 A | 2/1999 | Or et al. |
| 5,962,290 A | 10/1999 | Khosla et al. |
| 6,004,787 A | 12/1999 | Katz et al. |
| 6,011,142 A | 1/2000 | Bonnet et al. |
| 6,060,234 A | 5/2000 | Katz et al. |
| 6,066,721 A | 5/2000 | Khosla et al. |
| 6,080,555 A | 6/2000 | Khosla et al. |
| 6,121,432 A | 9/2000 | Bonnet et al. |
| 6,124,269 A | 9/2000 | Phan et al. |
| 6,271,255 B1 | 8/2001 | Leadlay et al. |

FOREIGN PATENT DOCUMENTS

| | | |
|---|---|---|
| FR | 2732023 | 3/1995 |
| WO | WO 9801546 | 1/1998 |
| WO | WO 9801571 | 1/1998 |
| WO | WO 9935156 | 7/1999 |
| WO | WO 0000500 | 1/2000 |
| WO | WO 0034297 | 6/2000 |
| WO | WO 0044761 | 8/2000 |
| WO | WO 71557 | 11/2000 |

OTHER PUBLICATIONS

Constantin Agouridas et al., J. Med. Chem. (1998), 41 (21), 4080–4100 Synthesis and Antibacterial Activity of Ketolides . . . .

Alexis Denis et al., Bioorg. Med. Chem. Lett., (1999), 9(21), 3075–3080 Synthesis and Antibacterial Activity of HMR 3647, A New Ketokide . . . .

Yat Sun Or et al., J. Med. Chem (2000), 43(6), 1045–1049, Design, Synthesis and Antimicrobial Activity of 6–0–Substituted Ketolides Active . . . .

*Primary Examiner*—Elli Peselev

(57) ABSTRACT

A series of ketolide antibacterials in the macrolide family of the formula:

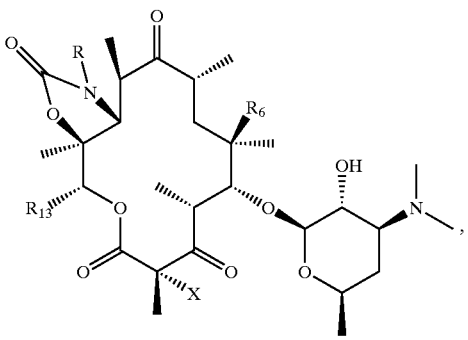

intermediates used in their manufacture and pharmaceutical compositions containing them. The compounds are erythromycin analogues useful in the treatment of bacterial and protozoal infections and in the treatment of other conditions involving gastric motility.

28 Claims, No Drawings

KETOLIDE ANTIBACTERIALS

This application claims priority under 35 USC §119 from Ser. Nos. 60/131,383 filed Apr. 28, 1999, 60/172,159, filed Dec. 17, 1999, 60/129,729, filed Apr. 16, 1999, 60/172,154 filed Dec. 17, 1999 and 60/140,175 filed Jun. 18, 1999. The contents of these applications are incorporated herein by reference.

FIELD OF THE INVENTION

This invention relates to a series of ketolide antibacterials in the macrolide family, intermediates used in their manufacture and pharmaceutical compositions containing them. The compounds are erythromycin analogues useful in the treatment of bacterial and protozoal infections and in the treatment of other conditions involving gastric motility.

BACKGROUND OF THE INVENTION

Polyketides are a family of natural products that include many compounds possessing antibiotic and other pharmacologic properties. Erythromycins are a class of macrolide antibiotics originally discovered in 1952 in the metabolic products of a strain of *Streptomyces erythreus*. The antibiotic occurs in various glycosylated forms, designated A, B, C and D. Since their discovery, many have worked to prepare derivatives of the molecule to improve or modify its properties. The focus of much of this work involved chemical modification of the naturally produced erythromycin molecule. This work has produced a number of derivatives including the semi-synthetic antibiotic, clarithromycin, which is 6-O-methylerythromycin. 12,11 oxycarbonyl substituted imino chemical derivatives of erythromycin are described in U.S. Pat. No. 5,635,485. However, because of the complexity of the macrolide molecule, medicinal chemistry efforts to produce derivatives have been limited by the kinds of modifications that can be made to the naturally occurring products.

Recently, work surrounding the search for modified polyketide antibiotics expanded with the discovery and isolation of the modular polyketide synthases (PKS's); multifunctional enzymes related to fatty acid synthases, which catalyze the biosynthesis of polyketides through repeated reactions between acylthioesters to produce the polyketide chain. The entire biosynthetic gene cluster from *S. erythraea* has been mapped and sequenced by Donadio et al. in Industrial Microorganisms: Basic and Applied Molecular Genetics (1993) R. H. Baltz, G. D. Hegeman, and P. L. Skatrud (eds.) (Amer. Soc. Microbiol.) and the entire PKS is a modular assembly of three multifunctional proteins encoded by three separate genes. U.S. Pat. No. 5,672,491 discloses the use of cells transformed with recombinant vectors encoding a variety of PKS gene clusters, which can be used to produce a variety of active polyketides. The vectors can include native or hybrid combinations of PKS subunits, or mutants thereof, to produce a variety of polyketide compounds. Cell-free systems which effect the production of polyketides employing modular polyketide synthases are reported in WO 97/02358.

Using these techniques, production of erythromycin analogues in which C-13 bears a substitution other than the natural ethyl group have been reported, for example in WO 98/01571, WO 99/35157, WO 99/03986, and WO 97/02358. WO 98/0156 describes a hybrid modular PKS gene for varying the nature of the starter and extender units to synthesize novel polyketides, including erythromycin analogues. U.S. Pat. Nos. 5,824,513 and 6,004,787 further describe methods to produce polyketide structures by introducing specific genetic alterations to genes encoding PKS in the EryA sequence of *S. erythraea*.

The present invention is concerned with novel chemical derivatives of unnatural erythromycin analogues prepared by manipulation of the modular PKS gene clusters.

SUMMARY OF THE INVENTION

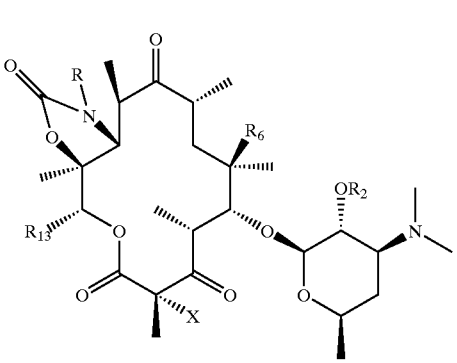

This invention is concerned with new compounds of the formula I:
wherein:
X is H, F, Cl, Br, or I;
$R_2$ is selected from H, —$COCH_3$ and —COPhenyl;
$R_6$ is selected from H and —O—$R_a$ where $R_a$ is substituted or unsubstituted alkyl ($C_1$–$C_{10}$), substituted or unsubstituted alkenyl ($C_2$–$C_{10}$), or substituted or unsubstituted alkynyl($C_2$–$C_{10}$);
$R_{13}$ is selected from H, ($C_1$–$C_8$) alkyl, 1-alkenyl ($C_2$–$C_8$), 1-alkynyl ($C_2$–$C_8$), substituted ($C_1$–$C_8$)alkyl, and —$CH_2$—R" where R" is selected from H, ($C_1$–$C_8$) alkyl, substituted ($C_1$–$C_8$)alkyl, cycloalkyl, alkenyl ($C_2$–$C_8$), alkynyl ($C_2$–$C_8$), aryl, substituted-aryl, ($C_1$–$C_8$) alkylaryl, heterocyclo, and substituted heterocyclo; provided that $R_{13}$ can not be ethyl;
R is selected from H, aryl, substituted-aryl, heterocyclo, substituted-heterocyclo, cycloalkyl, $C_{1-8}$-alkyl and $C_1$–$C_8$-alkenyl optionally substituted with one or more substituents selected from the group of aryl, substituted-aryl, heterocyclo, substituted-heterocyclo, hydroxy, $C_1$–$C_6$-alkoxy;
and the pharmaceutically acceptable salts, esters and prodrug forms thereof.

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of the specified number of carbon atoms.

The term "substituted alkyl" refers to an alkyl group substituted by, for example, one to four substituents, such as, halo, trifluoromethyl, trifluoromethoxy, hydroxy, alkoxy, cycloalkyloxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamine, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$) substituted carbamyl (e.g.CONH alkyl, CONH aryl, CONH aralkyl or cases where there are two substituents on the nitrogen selected from alkyl, aryl or aralkyl), alkoxycarbonyl, aryl, substituted aryl, guanidino and heterocycles, such as indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, napthyl, and biphenyl groups, each of which may be substituted.

The term "alkylaryl" or "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "cycloalkyl" refers to optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substitutents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thizaolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridinyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, to triazinyl, and triazinyl, and the like. Preferred heterocyclo groups include pyridinyl, pyrazinyl, pyrimidinyl, pyrroyl, pyrazolyl, imidazolyl, thiazolyl, oxazolyl, isoxazolyl, thiadiazolyl, oxadiazolyl, thienyl, furanyl, quinolinyl, isoquinolinyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridinyl, furopyridinyl (such as furo[2,3-c]pyridinyl, furo[3,2-b]pyridinyl), or furo[2,3-b]pyridinyl), imidazopyridinyl (such as imidazo[4,5-b] pyridinyl or imidazo[4,5-c]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

"Substituted heterocyclo" refers to heterocycle substituted by one to four substituents. Exemplary substituents include one or more alkyl groups as described above or one or more groups described above as alkyl substituents. Substituted-heterocyclo may be substituted with a mono-oxo to give for example a 4-oxo-1H-quinoline. Substituted-heterocyclo may also be substituted with a substituted-aryl or a second substituted-heterocyclo to give for example a 4-phenylimidazol-1-yl or a 4-(pyridin-3-yl)-imidazol-1-yl.

The following substituted heterocyclo groups are particularly preferred

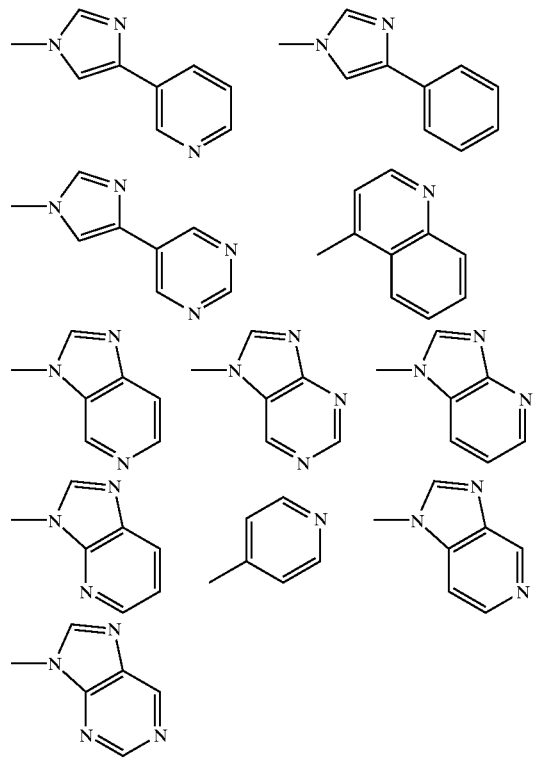

The compounds of the invention are those of formula I as set forth above, as well as any stereoisomeric forms of these compounds as shown. The particular stereoisomers depicted are those resulting from the preferred method of synthesis set forth above and exemplified herein; however, by modifying the expression system for the PKS, or by altering the chirality of the diketide, or by synthetic chemical conversion, other stereoisomers may also be prepared. Additional chiral centers may be present in the substituents, such as $R_a$ and $R_{13}$. The stereoisomers may be administered as mixtures, or individual stereoisomers may be separated and utilized as is known in the art.

The compounds are expected to possess antibacterial activity against Gram positive, Gram negative, and anaerobic bacteria due to their novel structure, and are expected to be useful as broad spectrum antibacterial agents for the treatment of bacterial infections in humans and animals. These compounds are particularly expected to have antimicrobial activity against S. aureus, S. epidermidis, S. pneumoniae, S. pyogenes, enterococci, Moraxella catarrhalis and H. influenzae. These compounds are particularly expected to be useful in the treatment of communityacquired pneumonia, upper and lower respiratory tract infections, skin and soft tissue infections, meningitis, hospital-acquired lung infections, and bone and joint infections.

Also included in the present invention are compounds useful as intermediates or producing the compounds of the present invention. Such intermediate compounds include those of the formula:

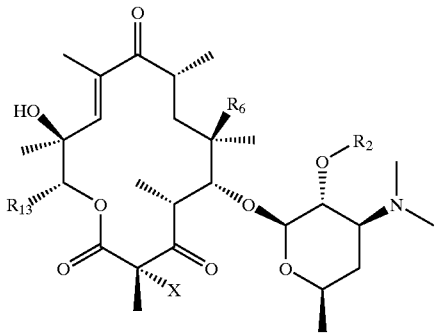

2

Wherein X, $R_6$ and $R_{13}$ are as described above, and $R_2$ is hydrogen or a hydroxyl protecting group, such as acetyl, benzoyl, or trimethylsilyl. Other intermediates included within the scope of this invention are those of the formula:

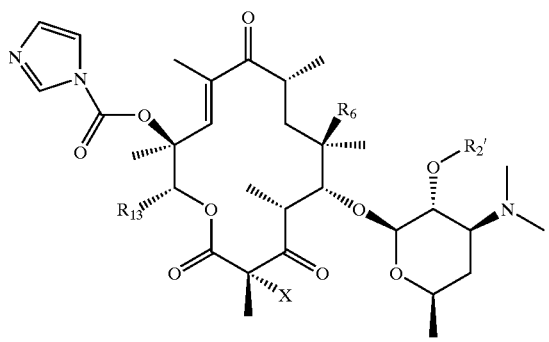

3

Wherein X, $R_6$ and $R_{13}$ are as described above, and $R_2$ is hydrogen or a hydroxyl protecting group, such as acetyl, benzoyl, or trimethylsilyl.

DETAILED DESCRIPTION

Preferred compounds are those of Formula I wherein:
X is H or F;
$R_2$ is as described above,
$R_6$ is selected from H and $(C_1-C_8)$ alkoxy;
$R_{13}$ is selected from H, $(C_1-C_4)$ alkyl, 1-alkenyl $(C_2-C_8)$ (particularly vinyl), 1-alkynyl $(C_2-C_8)$, haloalkyl, and —$CH_2$—R" where R" is selected from H, $(C_1-C_8)$ alkyl, haloalkyl, 1-alkenyl $(C_2-C_8)$, 1-alkynyl $(C_2-C_8)$, phenyl, and $(C_1-C_8)$ alkylphenyl (such as benzyl and phenethyl);
provided that $R_{13}$ can not be ethyl;
R is selected from H, aryl, substituted-aryl, heterocyclo, substituted-heterocyclo, cycloalkyl, $C_1-C_8$-alkyl and $C_1-C_8$-alkenyl optionally substituted with one or more substituents selected from the group of aryl, substituted-aryl, heterocyclo, substituted-heterocyclo, hydroxy, $C_1-C_6$-alkoxy;
and the pharmaceutically acceptable salts, esters and pro-drug forms thereof.

Particularly preferred groups for R include H, phenyl, $C_1-C_8$-alkyl or $C_1-C_8$-alkenyl optionally substituted with one or more substituents selected from the group of phenyl, hydroxy, and the following substituted heterocyclo groups.

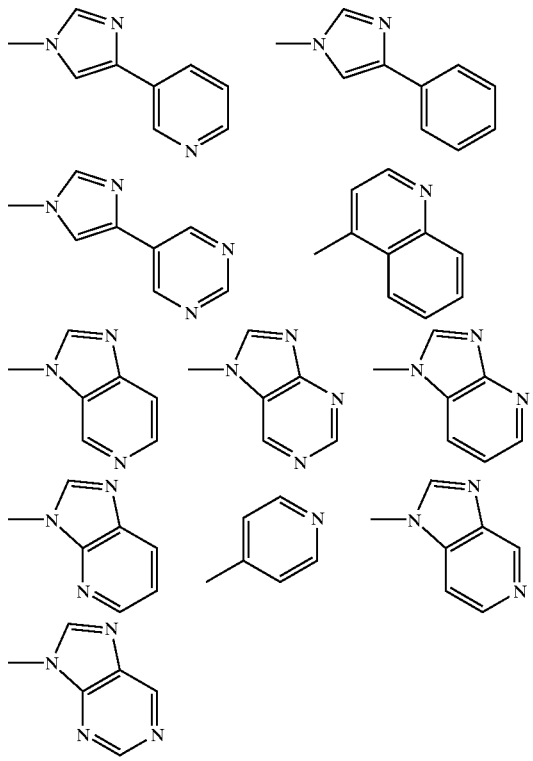

Another group of preferred compounds are those of the formula I wherein:
X is H or F;
$R_2$ is as described above,
$R_6$ is O—$R_a$ where $R_a$ is substituted or unsubstituted alkyl $(C_1-C_{10})$, substituted or unsubstituted alkenyl $(C_2-C_{10})$, or substituted or unsubstituted alkynyl $(C_2-C_{10})$;
$R_{13}$ is selected from H, $(C_1-C_8)$ alkyl, 1-alkenyl $(C_2-C_8)$ (particularly vinyl), 1-alkynyl $(C_2-C_8)$, haloalkyl, and —$CH_2$—R" where R" is selected from H, $(C_1-C_8)$ alkyl, haloalkyl, 1-alkenyl $(C_2-C_8)$, 1-alkynyl $(C_2-C_8)$, phenyl, and $(C_1-C_8)$ alkylphenyl (such as benzyl and phenethyl);
provided that $R_{13}$ can not be ethyl;
R is H;
and the pharmaceutically acceptable salts, esters and pro-drug forms thereof.

Particularly preferred groups for include optionally substituted 3-(quinolin-3-yl)prop-2-enyl, optionally substituted 3-(quinolin-3-yl)prop-2-ynyl, optionally substituted 3-(quinolin-6-yl)prop-2-enyl, optionally substituted 3-(quinolin-6-yl)prop-2-ynyl, optionally substituted 3-(quinolin-7-yl)prop-2-enyl, optionally substituted 3-phenylprop-2-enyl, optionally substituted 3-(naphth-1-yl)prop-2-enyl, optionally substituted 3-(naphth-1-yl)prop-2-ynyl, optionally substituted 3-(naphth-2-yl)prop-2-enyl, optionally substituted 3-(naphth-2-yl)prop-2-ynyl, optionally substituted 5-phenylpent-4-en-2-ynyl, optionally substituted 3-(fur-2-yl)prop-2-ynyl, optionally substituted 3-(thien-2-yl)prop-2-ynyl, optionally substituted 3-(carbazol-3-yl)prop-2-enyl, and optionally substituted 3-(quinoxalin-6-yl)prop-2-enyl.

The preferred compounds of this invention may be prepared according to the following reaction schemes:

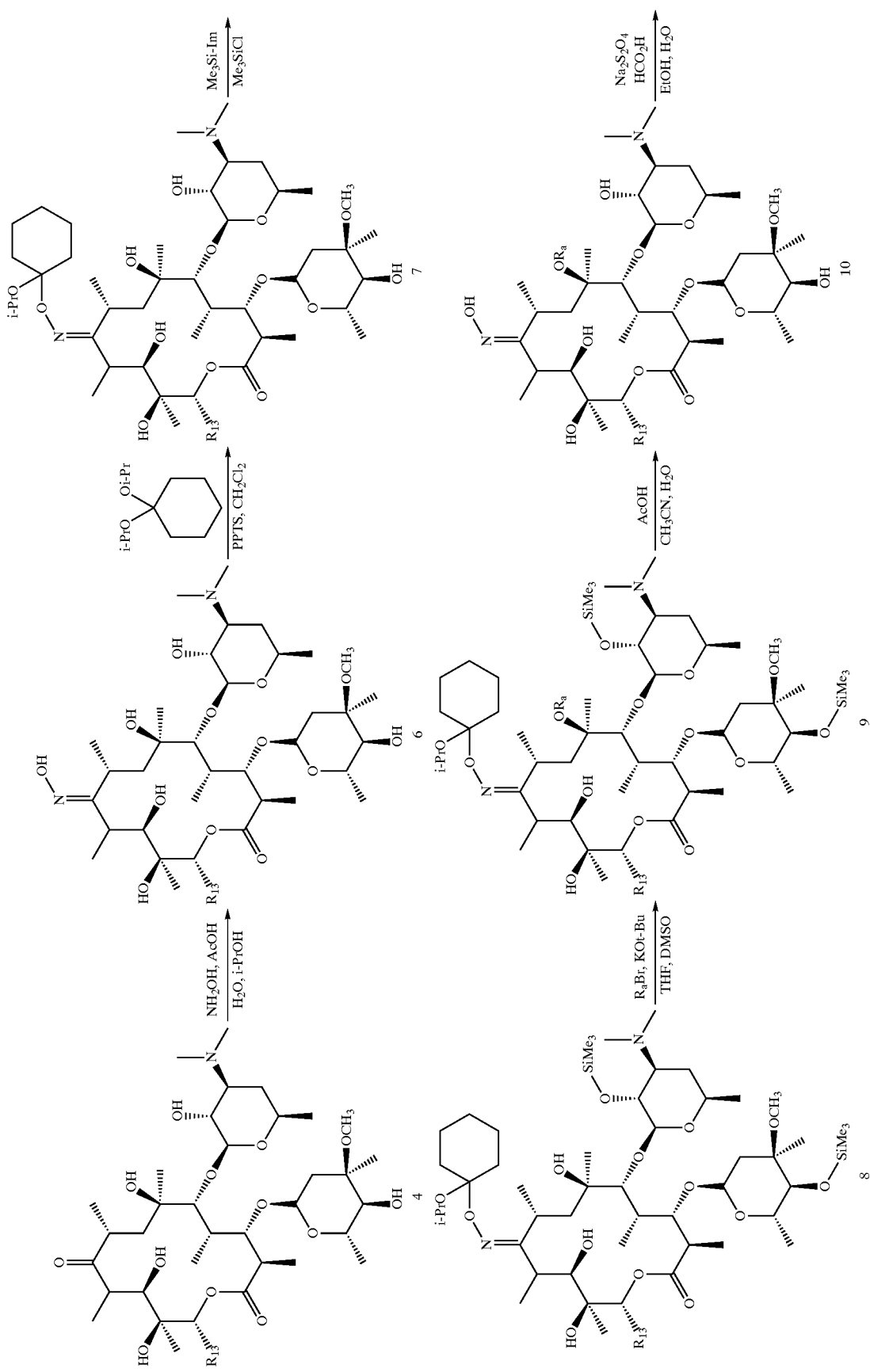

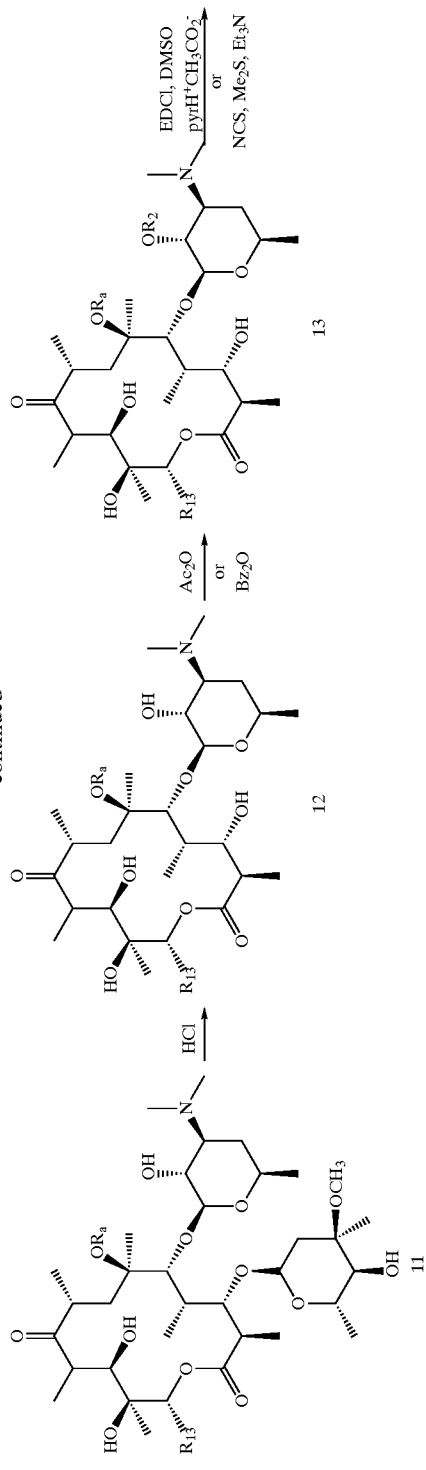
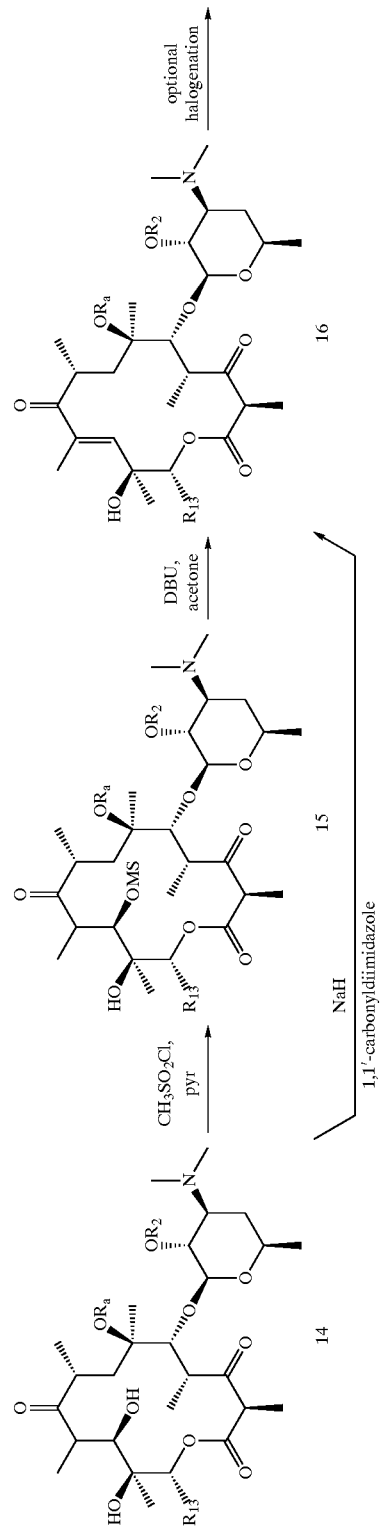
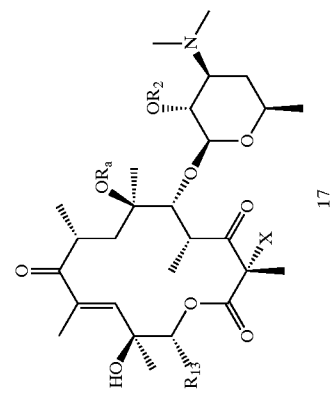

Scheme 2:
Synthesis of preferred compounds of the invention wherein $OR_a = (C_1-C_8)$ alkoxy
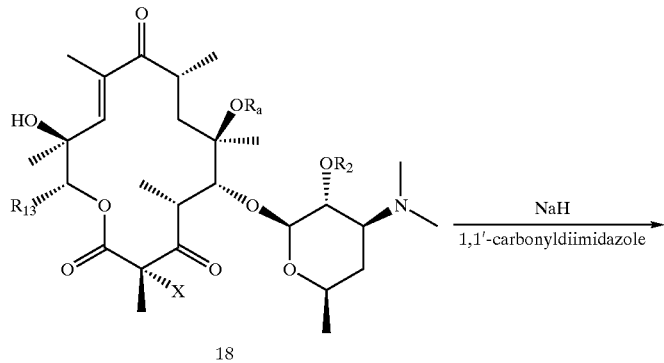
18
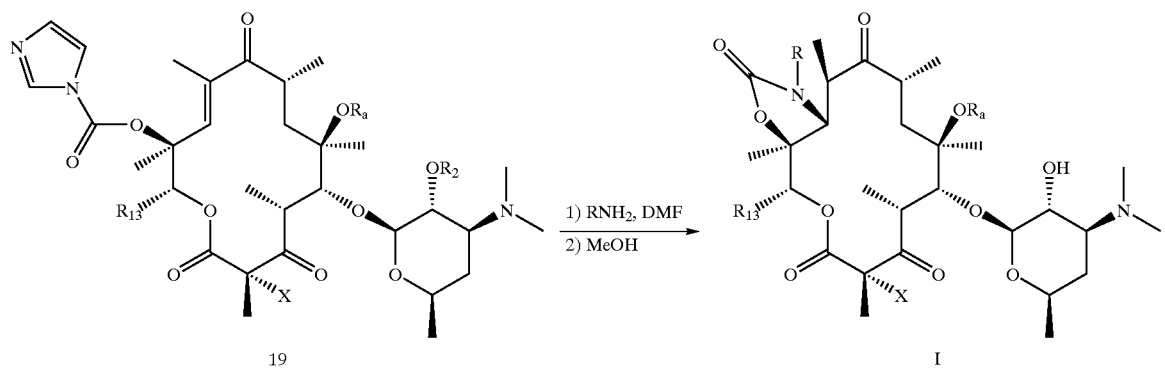
19            I
Scheme 3:
Synthesis of the preferred compounds of the invention wherein $R_a =$ substituted or unsubstituted alkyl $(C_1-C_{10})$, substituted or unsubstituted alkenyl $(C_2-C_{10})$, or substituted or unsubstituted alkynyl $(C_2-C_{10})$
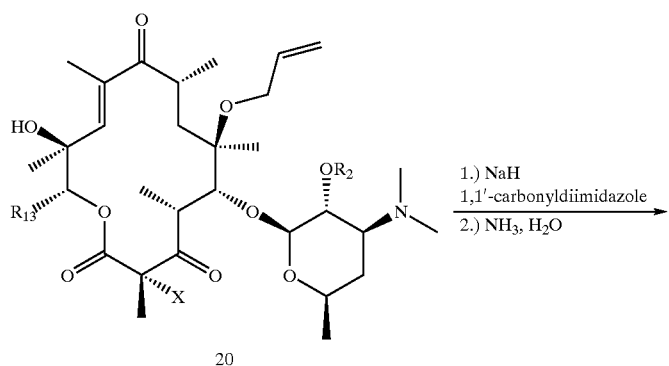
20

-continued
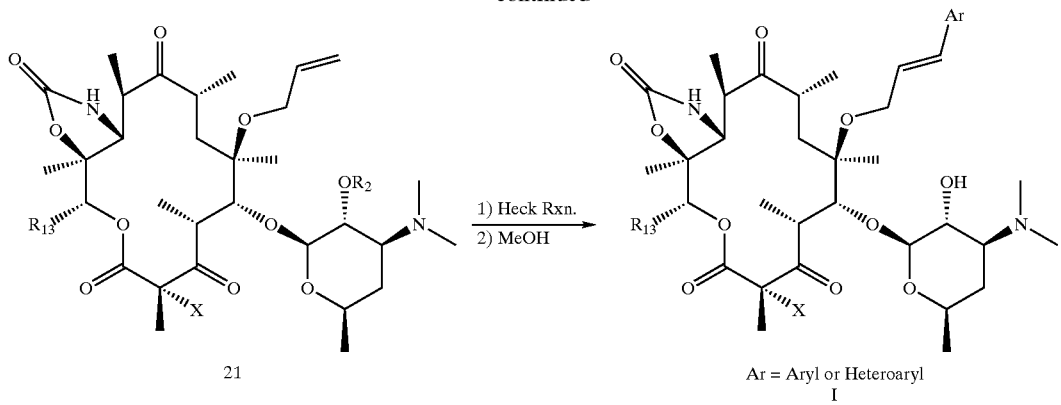
Ar = Aryl or Heteroaryl
I
The preferred compounds of the invention wherein $R_6$ is hydrogen may be prepared according to the following reaction scheme:
Scheme 4
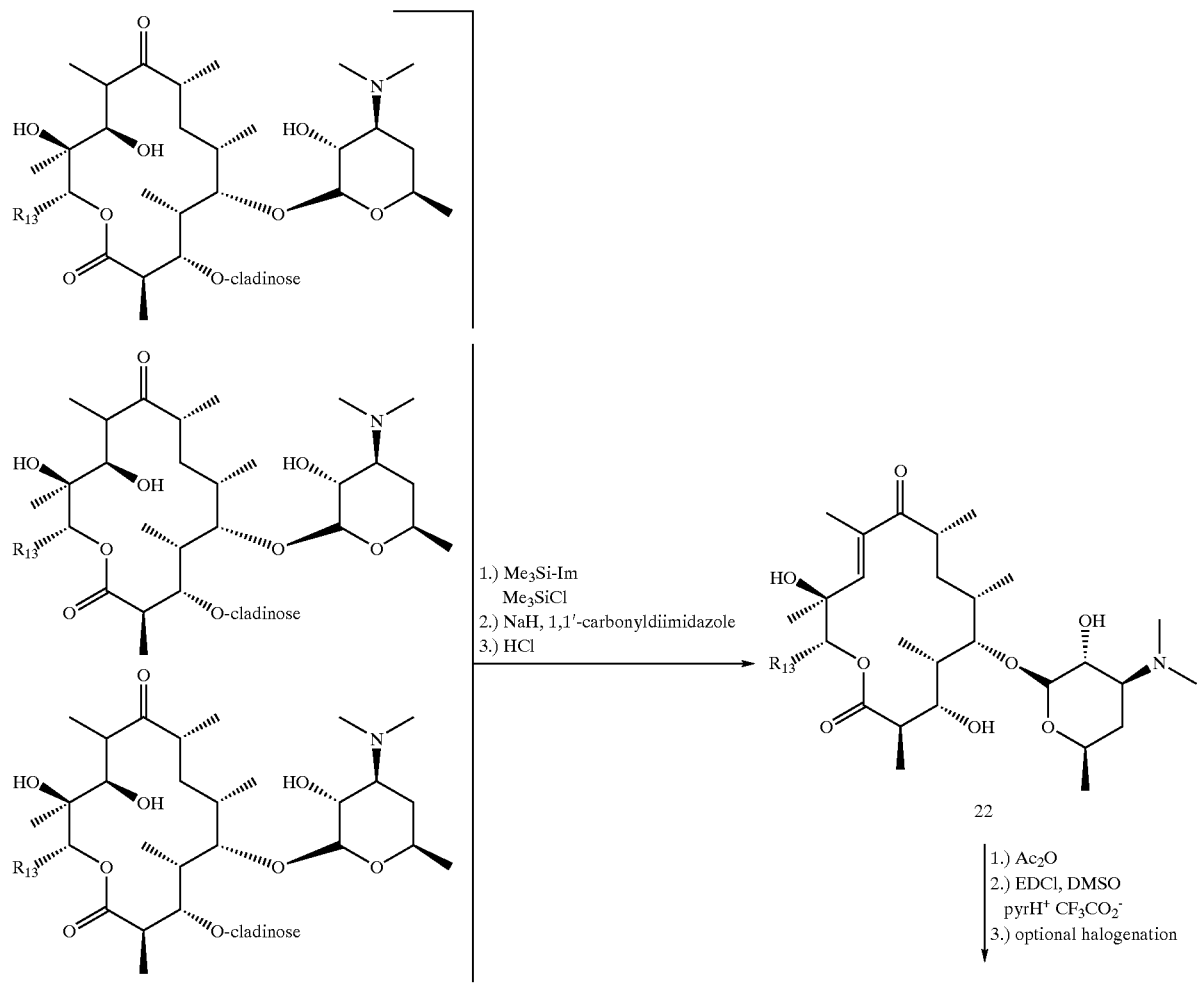

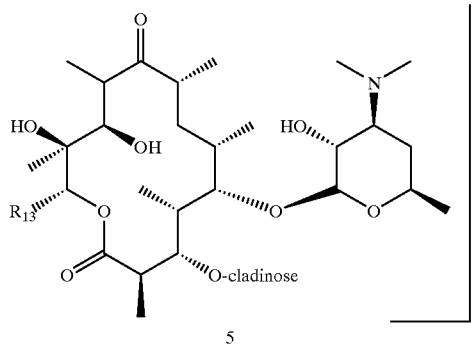

5

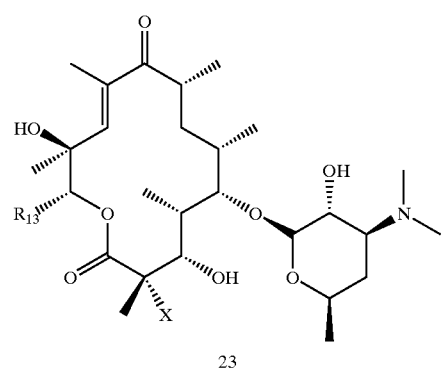

23

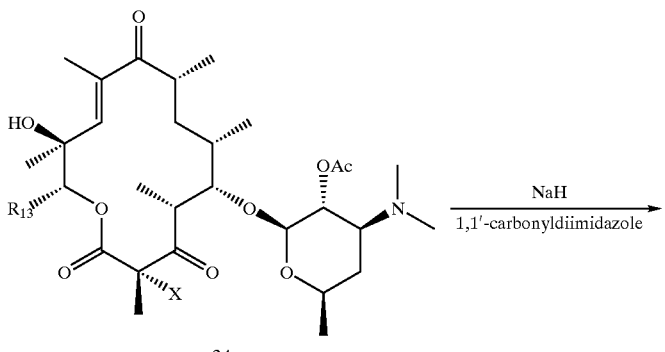

24

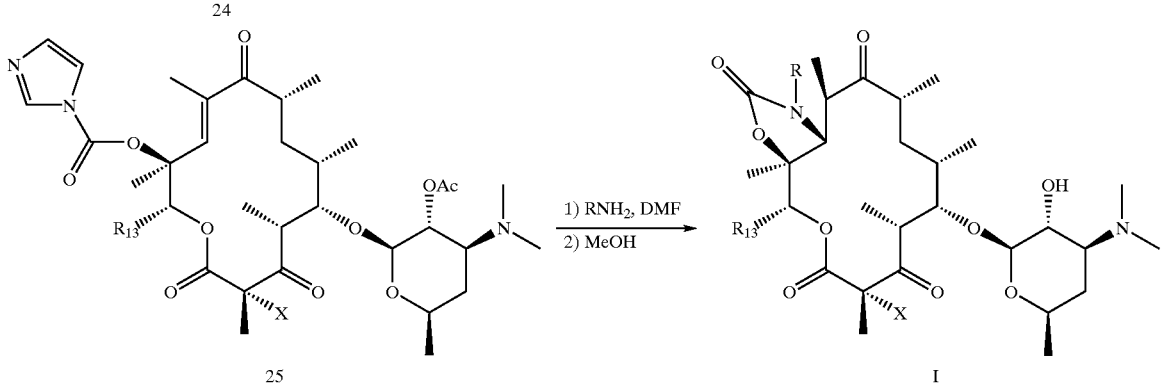

25                                             I

The starting macrolide intermediates, 4 and 5, may be prepared by methods described in U.S. Pat. No. 5,672,491, hereby incorporated by reference into the present application. In one embodiment, modified erythromycin intermediates, 4 and 5, may be prepared by a method in which an appropriate thioester diketide substrate is provided to 6-deoxyerythronolide B synthase (DEBS) that is unable to act on its natural substrate (propionyl CoA) due to a mutation in the ketosynthase domain of module 1 of DEBS. This recombinant DEBS can be expressed in the organism that natively produces erythromycin, *Saccharopolyspora erythraea*, or the entire gene cluster can be inserted by plasmid in a suitable host such as *S. coelicolor* (Jacobsen et al, Science 277:367–369 (1997)) or *S. lividans*, preferably an *S. coelicolor* or *S. lividans* which has been modified to delete its endogeneous actinorhodin polyketide synthesis mechanism. A suitable host would be *S. coelicolor* CH999/pJRJ2, which expresses a mutant 6-DEB synthase having an inactivated module 1 ketosynthase.

A cell free system as described in WO 97/02358 may also be employed by producing the relevant PKS proteins recombinantly and effecting their secretion or lysing the cells containing them. A typical cell-free system would include the appropriate PKS, NADPH and an appropriate buffer and substrates required for the catalytic synthesis of polyketides.

Further, the appropriate thioester diketide substrate can be provided to PKS enzymes other than the 6-DEB synthase of *Saccharopolyspora erythraea*. Other PKS enzymes include the 6-DEB synthase of *Micromonospora megalomicea* and its KS1° derivative described in U.S. Ser. No. 60/158305, the oleandolide PKS and its KS1° derivative described in PCT application No. US 99/24478, and the narbonolide PKS and its KS1° derivative described in PCT publication No. WO 99/61599, all incorporated by reference herein.

For those macrolide intermediates, 4 and 5, where $R_{13}$ is methyl, no diketide feeding is required because the desired aglycone may be produced by the recombinant host cell *Streptomyces coelicolor* CH999/pCK7, as further described herein.

The resulting aglycones thus prepared are then added to the fermentation broth of *Saccharopolyspora erythraea* strains which chemically glycosylate at the 3 and 5 positions, hydroxylate at C-12, and optionally hydroxylate at the 6 position, depending on the strain employed.

The modified erythromycins of the invention, in addition to modification at C-13, contain an —OH group at position 6 unless —OH is replaced by H or $OR_a$ as described above.

To construct, ultimately, the compounds of formula I where position 6 is $OR_a$, the compound of formula (4) is provided with protecting groups on the hydroxyl groups of the two glycose residues (Scheme 1). Such protection is effected using suitable protecting reagents such as acetic anhydride, benzoic anhydride, benzyl chloroformate, hexamethyldisilazane, or a trialkylsilyl chloride in an aprotic solvent. Aprotic solvents include, for example, dichloromethane, chloroform, tetrahydrofuran, N-methyl pyrrolidone, dimethyl sulfoxide (DMSO), dimethyl formamide (DMF) and the like. Mixtures may also be used. Protection of both sugar hydroxyls in formula (4) may be done simultaneously or sequentially.

In addition to protecting the 2' and 4" hydroxyl groups of the two glycose residues, the keto group at position 9 of the macrolide ring must also be protected. Typically, this is effected by converting the keto group to a derivatized oxime. Particularly preferred embodiments for R in the formula =NOR include unsubstituted or substituted alkyl (1–12C), substituted or unsubstituted aryl (6–10C), alkyl (1–12C), substituted or unsubstituted heteroaryl (6–10C), alkyl (1–12C), and heteroalkyl (such as substituents of the formula $CR'_2OR$ wherein each R', in addition to being independently embodied as R as set forth above, may, together with the other, form a cycloalkyl ring (3–12C)). A preferred derivatized oxime is of the formula =NOR wherein R is isopropoxycyclohexyl.

With the 9-keto group and the 2' and 4" hydroxyls protected, it is then possible to alkylate the 6-hydroxy group in the compound of formula (8) by reaction with an alkylating agent in the presence of base. Alkylating agents include alkyl halides and sulfonates. For example, the alkylating agents may include methyl tosylate, 2-fluoroethyl bromide, cinnamyl bromide, crotonyl bromide, allyl bromide, propargyl bromide, and the like. The alkylation is conducted in the presence of base, such as potassium hydroxide, sodium hydride, potassium isopropoxide, potassium t-butoxide, and an aprotic solvent.

The choice of alkylating agent will depend on the nature of the substituents $R_a$ to be included. As set forth above, $R_a$ can be substituted or unsubstituted alkyl (1–10C), substituted or unsubstituted alkenyl (2–10C), or substituted or unsubstituted alkynyl (2–10C). Particularly preferred are unsubstituted alkyl, alkenyl, or alkynyl, or substituted forms of these wherein the substituents include one or more halogen, hydroxy, alkoxy (1–6C), oxo, $SO_2R$ (1–6C), $N_3$, CN, and $NR_2$ wherein R is H, substituted or unsubstituted alkyl (including cycloalkyl) (1–12C), substituted or unsubstituted alkenyl (including cycloalkenyl) (2–12C), alkynyl (including cycloalkynyl) (2–12C), substituted or unsubstituted aryl (6–10C), including the hetero forms of the above.

Especially preferred are methyl, allyl and ethyl.

Once the alkylation of the 6-hydroxyl is completed, the sugar residues and the macrolide ring may be deprotected. Deprotection of the glycoside moieties is conducted as described by Green, T. W., et al., in *Protective Groups in Organic Synthesis*, infra. Similar conditions result in converting the derivatized oxime to =NOH. If formation of the underivatized oxime is not concurrent with deprotection, the conversion to the oxime is conducted separately.

The oxime can then be removed and converted to a keto group by standard methods known in the art. Deoximating agents include inorganic sulfur oxide compounds such as sodium hydrogen sulfite, sodium pyrosulfate, sodium thiosulfate, and the like. In this case, protic solvents are used, such as water, methanol, ethanol, isopropanol, trimethyl silanol and mixtures of these. In general, the deoximation reaction is conducted in the presence of an organic acid.

At this point in the process, or later, the group introduced at the 6-hydroxyl can further be manipulated. Conveniently, the initial substitution may provide a 6-O-allyl, i.e., $O-CH_2CH=CH_2$, which can further be derivatized by reduction to give the 6-O propyl compound, or be treated with osmium tetroxide to provide the 2,3-dihydroxypropyl compound, which can further be esterified at each oxygen atom. The O-allyl derivative can also be oxidized with m-chloroperoxybenzoic acid in an aprotic solvent to provide the epoxy compound which can be opened with amines or N-containing heteroaryl compounds to provide compounds with N-containing side-chains, or can be oxidized under Wacker conditions to provide the substituent $O-CH_2-C(O)-CH_3$, or can be ozonized to provide the aldehyde. The aldehyde can then be converted to the oxime or reacted with a suitable amine and reduced in the presence of a borohydride reducing agent to provide an amine. The oxime can also be converted to a nitrile by reaction with a dehydration agent in an aprotic solvent. The O-allyl derivative can also be reacted with an aryl halide under Heck conditions (Pd(II) or Pd(O), phosphine and amine or inorganic base) to provide a 3-aryl prop-2-enyl derivative (Scheme 3). This derivative can then be reduced with hydrogen and palladium on carbon to provide a 3-arylpropyl derivative. If the initial substituent $R_a$ is a 2-propyne, similar reactions can be employed to provide alterations in the side-chain, including arylation.

In order to convert the compound of formula (11) into the compound of formula (12), by first removing the cladinose moiety, the compound of formula (11) is treated with mild aqueous acid or with a deglycosylating enzyme (Scheme 1). Suitable acids include hydrochloric, sulfuric, chloroacetic, trifluoroacetic and the like, in the presence of alcohol. Reaction times are typically 0.5–24 hours at a temperature of –10–35° C. Following protection of the 2' hydroxyl of the remaining sugar as set forth above, the resulting hydroxyl group at the 3-position of the macrolide ring is then oxidized to the ketone using a modified Swern oxidation procedure. In this procedure, an oxidizing agent such as N-chlorosuccinimide-dimethyl sulfide or a carbodiimide-dimethylsuloxide is used. Typically, a compound of formula (13) is added to a pre-formed N-chlorosuccinimide and dimethyl sulfide complex in a chlorinated solvent such as methylene chloride at –10–25° C. After being stirred for 0.5–4 hours, a tertiary amine such as triethylamine is added to produce the corresponding ketone.

Intermediate (16) can then be prepared from intermediate (14) in a two-step procedure as illustrated in Scheme 1. First the 11-hydroxyl group is preferentially converted to a leaving group, such as methanesulfonate, by reaction with an alkyl or arylsulfonyl chloride, such as methanesulfonyl chloride, in the presence of an organic base, like pyridine. In the next step, the leaving group is eliminated to afford the 10–11 double bond by treatment with diazabicycloundecane in a suitable solvent like acetone.

In order to halogenate the macrolide at position 2 (converting X=H to halogen), the compound of formula (16), is treated with a base and an electrophilic halogenating reagent such as pyridinium perbromide or N-fluorobenzene sulfonic acid.

In accordance with Scheme 2, intermediate (18) is reacted with sodium hydride and 1,1'-carbonyldiimidazole to yield the imidazole intermediate (19). Intermediate (19) is then reacted with the appropriate substituted amine in dimethylformamide at about 25° to 130° and then the hydroxy protecting group is removed by treatment with methanol to yield the final compound I.

In a similar fashion (Scheme 3), intermediate (20) can be converted to the unsubstituted 11,12-cyclic carbamate intermediate (21) by reaction of the analogous imidazole intermediate with aqueous ammonia. As mentioned earlier, the 6-position substituent can be manipulated late in the synthetic sequence, and this is illustrated in Scheme 3, where the 6-O-allyl derivative is reacted with an aryl halide under Heck conditions (Pd(II) or Pd(O), phosphine and amine or inorganic base) to provide a 3-aryl prop-2-enyl derivative. Subsequent deprotection of the 2' hydroxyl group affords the final compound I.

It will also be noted that compounds of the invention wherein $R_6$ is hydrogen can be readily obtained from a mixture of 6-deoxy-13-substituted-erythromycins A, B, C, and D derived from fermentation. A similar series of reactions as described above can be used to effect this conversion (Scheme 4).

This invention further provides a method of treating bacterial infections, or enhancing the activity of other antibacterial agents, in warm-blooded animals, which comprises administering to the animals a compound of the invention alone or in admixture with a diluent or in the form of a medicament according to the invention.

When the compounds are employed for the above utility, they may be combined with one or more pharmaceutically acceptable carriers, e.g., solvents, diluents, and the like, and may be administered orally in such forms as tablets, capsules, dispersible powders, granules, or suspensions containing for example, from about 0.5% to 5% of suspending agent, syrups containing, for example, from about 10% to 50% of sugar, and elixirs containing, for example, from about 20% to 50% ethanol, and the like, or parenterally in the form of sterile injectable solutions or suspensions containing from about 0.5% to 5% suspending agent in an isotonic medium. These pharmaceutical preparations may contain, for example, from about 0.5% up to about 90% of the active ingredient in combination with the carrier, more usually between 5% and 60% by weight.

Compositions for topical application may take the form of liquids, creams or gels, containing a therapeutically effective concentration of a compound of the invention admixed with a dermatologically acceptable carrier.

In preparing the compositions in oral dosage form, any of the usual pharmaceutical media may be employed. Solid carriers include starch, lactose, dicalcium phosphate, microcrystalline cellulose, sucrose and kaolin, while liquid carriers include sterile water, polyethylene glycols, non-ionic surfactants and edible oils such as corn, peanut and sesame oils, as are appropriate to the nature of the active ingredient and the particular form of administration desired. Adjuvants customarily employed in the preparation of pharmaceutical compositions may be advantageously included, such as flavoring agents, coloring agents, preserving agents, and antioxidants, for example, vitamin E, ascorbic acid, BHT and BHA.

The preferred pharmaceutical compositions from the standpoint of ease of preparation and administration are solid compositions, particularly tablets and hard-filled or liquid-filled capsules. Oral administration of the compounds is preferred.

These active compounds may also be administered parenterally or intraperitoneally. Solutions or suspensions of these active compounds as a free base or pharmacologically acceptable salt can be prepared in water suitably mixed with a surfactant such as hydroxypropyl-cellulose. Dispersions can also be prepared in glycerol, liquid polyethylene glycols and mixtures thereof in oils. Under ordinary conditions of storage and use, these preparations may contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The effective dosage of active ingredient employed may vary depending on the particular compound employed, the mode of administration and the severity of the condition being treated. However, in general, satisfactory results are obtained when the compounds of the invention are administered at a daily dosage of from about 0.1 mg/kg to about 400 mg/kg of animal body weight, preferably given once a day, or in divided doses two to four times a day, or in sustained release form. For most large mammals the total daily dosage is from about 0.07 g to 7.0 g, preferably from about 100 mg to 1000 mg Dosage forms suitable for internal use comprise from about 100 mg to 500 mg of the active compound in intimate admixture with a solid or liquid pharmaceutically acceptable carrier. This dosage regimen may be adjusted to provide the optimal therapeutic response. For example, several divided doses may be administered daily or the dose may be proportionally reduced as indicated by the exigencies of the therapeutic situation.

The production of the above-mentioned pharmaceutical compositions and medicaments is carried out by any method known in the art, for example, by mixing the active ingredients(s) with the diluent(s) to form a pharmaceutical composition (e.g. a granulate) and then forming the composition into the medicament (e.g. tablets).

EXAMPLES

The compounds of the invention can be prepared using intermediates produced by a chemobiosynthetic procedure involving recombinant host cells and organic chemistry methodology. The steps of this chemobiosynthetic procedure are described generally below, followed by a detailed description of each step in the enumerated Examples.

In the first general step of the method, a 6-deoxyerythronolide B (6-dEB) derivative compound is prepared by fermentation of a recombinant Streptomyces host cell.

The fermentation to produce 15-methyl-6-deoxyerythronolide B and 14,15-dehydro-6-deoxyerythronolide B requires a synthetic diketide intermediate to be fed to the fermenting cells. The preparation of these synthetic diketides is described in Example 1. These synthetic diketides are substrates for a 6-deoxyerythronolide B synthase (DEBS) that is unable to act on its natural substrate (propionyl CoA) due to a mutation in the ketosynthase domain of module 1 of DEBS. This recombinant DEBS is provided by plasmid pJRJ2 in *Streptomyces coelicolor* CH999. *S. coelicolor* CH999 is described in U.S. Pat. No. 5,672,491, incorporated herein by reference. A derivative of *S. coelicolor* CH999, *S. coelicolor* K39–02, that has been genetically modified to include a ptpA gene, is described in U.S. patent application Ser. No. 09/181,833, incorporated herein by reference can also be employed for this purpose. Plasmid pJRJ2 encodes the eryAI, eryAII, and eryAIII genes; the eryAI gene contained in the plasmid contains the KS1 null mutation. The KS1 null mutation prevents formation of the 6-deoxyerythronolide B produced by the wild-type gene unless exogenous substrate is provided. Plasmid pJRJ2 and a process for using the plasmid to prepare novel 13-substituted erythromycins are described in PCT publication Nos. 99/03986 and 97/02358 and in U.S. patent application Ser. Nos. 08/675,817, filed Jul. 5, 1996; Ser. No. 08/896,323, filed Jul. 17, 1997; and 09/311,756, filed May 14, 1999, each of which is incorporated herein by reference. The exogenous substrates provided can be prepared by the methods and include the compounds described in PCT patent application No. PCT/US00/02397 and U.S. patent application Ser. No. 09/492,733, both filed Jan. 27, 2000, by inventors G. Ashley et al., and both of which claim priority to U.S. patent application Ser. No. 60/117,384, filed Jan. 27, 1999, each of which is incorporated herein by refernce. PKS genes other than the ery genes can also be employed; suitable genes include the KS1 null mutation containing oleandolide and megalomicin PKS genes described in U.S. patent application Ser. Nos. 60/158,305, filed Oct. 8, 1999 and Ser. No. 09/428,517, filed Oct. 28, 1999, and PCT application No. US99/24478, filed Oct. 22, 1999, each of which is incorporated herein by reference.

The fermentation to produce 14-nor-6-deoxyerythronolide B does not require diketide feeding, because the desired compound is produced by the recombinant host cell Streptomyces coelicolor CH999/pCK7. Plasmid pCK7 is described in U.S. Pat. No. 5,672,491 and comprises the DEBS genes. A derivative of plasmid pCK7, pKOS011-26, can also be used. The host cell comprising pKOS011-26 and a recombinant ptpA gene is called *S. coelicolor* 27-26/pKOS011-26. These host cells produce both 6-deoxyerythronolide B and 14-nor-6-deoxyerythronolide, due to the incorporation of propionyl CoA and acetyl CoA, both of which serve as substrates for DEBS.

The fermentation of *Streptomyces coelicolor* CH999/pJRJ2 and *S. coelicolor* CH999/pCK7 is described in Example 2. The isolation of the 6-deoxyerythronolide products resulting from this fermentation is also described in Example 2.

The isolated products are then added to the fermentation broth of *Saccharopolyspora erythraea* strains to make other useful intermediate compounds of the invention. The *S. erythraea* strains catalyze the biosynthesis and attachment of sugar residues to the 3 and 5 positions of the 6-dEB derivative compounds. These strains also comprise a functional eryK gene product and so hydroxylate the 6-dEB derivative compounds at the 12 position. The strains differ in regard to whether a functional eryF gene product is produced. If so, then the compounds produced are hydroxylated at the 6 position as well. If not, then a 6-deoxyerythromycin A derivative is produced. These *S. erythraea* fermentations are described in Example 3, together with the isolation of the erythromycin A derivative compounds from the fermentation broth.

The isolated products are then used as intermediates in the chemical synthesis of other intermediate compounds of the invention. For erythromycin A derivative compounds of the invention that comprise a 6-hydroxyl, Examples 4–6, 11, and 16 describe the process for alkylating the compounds to make the 6-O-alkyl, 6-O-allyl, and 6-O-propargyl intermediates of the invention, as depicted in Scheme 1 [Intermediates (8)→(11)].

For erythromycin A derivative compounds of the invention that comprise the 6-O-alkyl groups, Examples 7–9 describe the process for making the 10,11-anhydro compounds of the invention. This reaction sequence is depicted in Scheme 1 [Intermediates (11)→(16)]. Example 10 describes the process for making the 2-halo compounds of the invention. In particular, the compound of formula (26), is treated with a base and an electrophilic halogenating reagent such as pyridinium perbromide or N-fluorobenzenesulfonic acid, as depicted in Scheme 5. Example 12 describes the process for removing the cladinose sugar from erythromycin A derivatives containing the 6-O-allyl group and for oxidation of the resulting 3-hydroxyl group to the ketone [Scheme 1; Intermediates (11)→(14)]. Example 13 illustrates the conversion of the compounds containing the 6-O-allyl group to several useful intermediates in the synthesis of compounds of the invention. Example 14 describes the synthesis of a compound of the invention (I) wherein R=H, $R_2$=H, X=H and $R_6$=O-allyl [Scheme 1; Intermediates (14)→(17) and Scheme 3; Intermediate (20)→(I)]. Example 15 describes the process for conversion of macrolides containing the 6-O-allyl and 11,12-cyclic carbamate functionalities to compounds of the invention (I) via the Heck reaction and subsequent deprotection of the desosamine sugar (Scheme 3; Intermediate (21)→(I)]. In addition to illustrating the alkylation of the compounds to the 6-O-propargyl intermediates, Example 16 further describes the process for conversion of these intermediates to compounds of the invention (I). Example 17 describes the process for conversion of 6-O-propargyl intermediates to another group of compounds of the invention (I) via the Sonogashira reaction. For erythromycin A derivative compounds of the invention that do not comprise a 6-hydroxyl, Examples 18–20 describe the process for making the 10,11-anhydro compounds of the invention. These reaction sequences are depicted in Schemes 4 and 6. Example 21 describes the process for the synthesis of 1H-imidazo[4,5-b]pyridine-1-(4-amino-2-butene), an amine used in the synthesis of compounds of the invention wherein R=

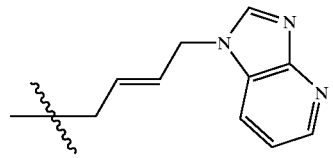

This sequence of reactions is depicted in Scheme 7. The process for conversion of the 10,11-anhydro compounds into the carbamate derivative compounds of the invention is described in Examples 22 and 23 [Scheme 3; Intermediate (18)→(I)]. The amines used in the synthesis of the carbamate derivative compounds of the invention (I) are either commercially available or can be readily prepared as described in Denis et al, Bioorg. Med. Chem. Lett. 9:3075–3080 (1999).

Example 1

Preparation of Diketide Thioesters

The processes used to prepare the N-acetylcysteaminethioesters (NACS) used to feed the recombinant Streptomyces host cells to make the 15-methyl and 14,15-dehydro-6-deoxyerythronolide B intermediate compounds are described in this Example. The synthesis protocols described below are also described in U.S. provisional patent application Ser. No. 09/492,733; inventors G. Ashley, M. Burlingame, and I. Chan-Kai, incorporated herein by reference.

Thus, (2S,3R)-2-methyl-3-hydroxyhexanoate NACS (Preparation E), which is used to prepare the 15-methyl-6-deoxyerythronolide B intermediate, is prepared from reacting (4S)-N-[(2S,3R)-2-methyl-3-hydroxyhexanoyl]-4-benzyl-2-oxazolidinone (Preparation D) with N-acetylcysteamine (Preparation B). N-acetylcysteamine is, in turn, prepared from N,S-diacetylcysteamine (Preparation A). (4S)-N-[(2S,3R)-2-methyl-3-hydroxyhexanoyl]-4-benzyl-2-oxazolidinone (Preparation D) is prepared from (4S)-N-Propionyl-4-benzyl-2-oxazolidinone (Propionyl-Nox; Preparation C).

In similar fashion, (2S,3R)-2-methyl-3-hydroxy-4-pentenoate NACS (Preparation G), which is used to prepare the 14,15-dehydro-6-deoxyerythronolide B intermediate, is prepared from reacting (4S)-N-[(2S,3R)-2-methyl-3-hydroxy-4-pentenoyl]-4-benzyl-2-oxazolidinone (Preparation F) with N-acetylcysteamine (Preparation B). (4S)-N-[(2S,3R)-2-methyl-3-hydroxy-4-pentenoyl]-4-benzyl-2-oxazolidinone (Preparation F) is prepared from (4S)-N-Propionyl-4-benzyl-2-oxazolidinone (Propionyl-Nox; Preparation C).

Preparation A: Preparation of N,S-Diacetylcysteamine

Cysteamine hydrochloride (50.0 g) is added to a 1 L 3-neck round bottom flask fitted with a magnetic stir bar, 2 addition funnels, and a pH electrode. Water (300 mL) is added, and the stirred solution is cooled on ice. The pH is adjusted to 8.0 by addition of 8 N KOH. Acetic anhydride (125 mL) is placed in one addition funnel, and 8N KOH (350 mL) is placed in the other addition funnel. The acetic anhydride is added dropwise to the cysteamine solution, with 8 N KOH being added so as to keep the reaction pH at 8 +/−1. After addition of acetic anhydride is complete, the pH was adjusted to 7.0 using 1 N HCl and the mixture is allowed to stir for 75 min. on ice. Solid NaCl is added to saturation, and the solution is extracted 4 times using 400 mL portions of $CH_2Cl_2$. The organic extracts are combined, dried over $MgSO_4$, filtered, and concentrated under reduced pressure to yield 68.9 g (97% yield) of a pale yellow oil, which crystallizes upon standing at 4° C.

Preparation B: Preparation of N-Acetylicysteamine

N,S-diacetylcysteamine (42.64 g) is placed in a 2 L round bottom flask fitted with a magnetic stirrer, and dissolved in 1400 mL of water. The flask is purged with $N_2$, and the mixture is chilled in an ice bath. Potassium hydroxide (49.42 g) is added, and the mixture is stirred for 2 hr. on ice under inert atmosphere. The pH is adjusted to 7 using 6 N HCl, and solid NaCl is added to saturation. The mixture is extracted 7 times with 500 mL portions of $CH_2Cl_2$. The organic extracts are combined, dried over $MgSO_4$, filtered, and concentrated under reduced pressure to yield 30.2 g (96% yield) of product. This material is distilled immediately prior to use, bp 138–140° C./7 mm Hg.

Preparation C: Preparation of (4S)-N-Propionyl-4-benzyl-2-oxazolidinone (Propionyl-Nox)

A dry, 1 L three-necked round bottomed flask equipped with a 500 mL addition funnel and a stir bar was charged with 20 g of (4S)-4-benzyl-2-oxazolidinone, capped with septa and flushed with nitrogen. Anhydrous THF (300 mL) was added by cannula and the resulting solution was cooled with a −78° C. bath of dry ice/isopropanol. The addition funnel was charged with 78 mL of n-butyllithium (1.6 M in hexane) by cannula, which was added in a slow stream to the reaction. Distilled propionyl chloride (bp 77–79° C.), 8.0 mL, was added rapidly via syringe.

The reaction was allowed to stir for 30 min. in the dry ice/isopropanol bath.

The reaction was removed from the cold bath, allowed to warm to >0° C., and quenched with 50 mL of saturated aqueous $NH_4Cl$. The mixture was concentrated to a slurry on a rotary evaporator. The slurry was extracted three times with 250 mL portions of ethyl ether. The organic extracts were combined and washed with 50 mL each of saturated aqueous $NaHCO_3$ and brine, dried with $MgSO_4$, filtered, and concentrated to give a yellow oil. The material crystallized upon sitting. The crystals were triturated once with cold (−20° C.) hexanes to give 21.0 g (80% yield) of white crystalline material, m.p. 41–43° C. APCI-MS: m/z=234 (MH+), 178, 117. 1H-NMR (360 MHz, $CDCl_3$): 7.2–7.4 (5H, m); 4.67 (1H, m, H4); 4.14–4.22 (2H, m, H5); 3.30 (1H, dd, J=3,13 Hz, benzylic); 2.89–3.03 (2H, m, H2'); 2.77 (1H, dd, J=9,13,benzylic); 1.20 (3H, t, J=7 Hz, H2').

Preparation D: Preparation of (4S)-N-[(2S,3R)-2-Methyl-3-hydroxyhexanoyl]-4-benzyl-2-oxazolidinone

A dry, 2 L three-necked round bottomed flask equipped with a 500 mL addition funnel, a low-temperature thermometer, and a stir bar was charged with 19.84 g of N-propionyl-oxazolidinone, capped with septa and flushed with nitrogen. Anhydrous dichloromethane (100 mL) was added by cannula, and the resulting solution was cooled to −65° C. in a bath of dry ice/isopropanol. The addition funnel was charged by cannula with 100 mL of dibutylboron triflate (1.0 M in dichloromethane), which was added in a slow stream to the reaction. Triethylamine (15.6 mL) was added dropwise by syringe, keeping the reaction temperature below −10° C. The reaction was then transferred to an ice bath and allowed to stir at 0° C. for 30 min. After that period, the reaction was placed back into the dry ice/isopropanol bath and allowed to cool to −65° C. Butyraldehyde (8.6 mL) was added rapidly by syringe, and the reaction was allowed to stir for 30 min.

The reaction was transferred to an ice bath and the addition funnel was charged with 100 mL of a 1 M aqueous phosphate solution, pH 7.0 (the phosphate solution is comprised of equal molar amounts of mono- and dibasic potassium phosphate). The phosphate solution was added as quickly as possible while keeping the reaction temperature below 10° C. The addition funnel was then charged with 300 mL methanol which was added as quickly as possible while keeping the reaction temperature below 10° C. Finally, the addition funnel was charged with 300 mL of 2:1 methanol:30% hydrogen peroxide. This was added dropwise to ensure that the temperature was kept below 10° C. The reaction was stirred for one hr. after completion of addition. The solvent was then removed on a rotary evaporator until a slurry remained. The slurry was extracted 4 times with 500 mL portions of ethyl ether. The combined organic extracts were washed with 250 mL each of saturated aqueous sodium bicarbonate and brine. The extract was then dried with $MgSO_4$, filtered, and concentrated to give a slightly yellow oil. The material was then chromatographed on $SiO_2$ using 2:1 hexanes:ethyl acetate (product Rf=0.4) resulting in 22.0 g (85% yield) of title compound as a colorless oil.

APCI-MS: m/z 306 (MH+); 1H-NMR (360 MHz, $CDCl_3$): 7.2–7.4 (5H, m, phenyl); 4.71 (1H, m, H4); 4.17–4.25 (2H, m, H5); 3.96 (1H, m, H3'); 3.77 (1H, dq, J=2.5,7 Hz, H2'); 3.26 (1H, dd, J=4,13 Hz, benzylic); 2.79 (1H, dd, J=9,13 Hz, benzylic); 1.5–1.6 (2H, m, H4'); 1.3–1.5 (2H, m, H5'); 1.27 (3H, d, J=7 Hz, 2'-Me); 0.94 (3H, t, J=7 Hz, H6').

Preparation E: Preparation of (2S,3R)-2-Methyl-3-hydroxyhexanoate N-Acetylcysteamine Thioester

N-acetylcysteamine was distilled at 130° C./7 mm Hg to give a colorless liquid at room temperature. A dry, 1 L three-necked round bottomed flask equipped with a 500 mL addition funnel and a stir bar was capped with septa and flushed with nitrogen. The flask was then charged with 10.7 mL of N-acetylcysteamine by syringe and with 400 mL of anhydrous THF by cannula. The mixture was cooled with a MeOH/ice bath. Butyllithium (64 mL of 1.6 M in hexanes) was added dropwise by syringe, resulting in formation of a white precipitate. After stirring for 30min., trimethylaluminum (51 mL of 2.0 M in hexanes) was added dropwise by syringe. The reaction became clear after addition of trimethylaluminum and was allowed to stir an additional 30 min. During this period, 20.5 g (0.068 mol) of (4S)-N-[(2S,3R)-2-methyl-3-hydroxylhexanoyl]-4-benzyl-2-oxazolidinone was put under a blanket of nitrogen and dissolved in 100 mL of anhydrous THF; this solution was then transferred in a slow stream by cannula into the reaction, The resulting reaction mixture turned a yellow-green color and was allowed to stir for 1 hr. The reaction was finished when the starting material could no longer be seen by thin-layer chromatographic analysis (ca. 1 hr.).

The reaction was treated with enough saturated oxalic acid to give a neutral reaction with pH paper (approximately 90 mL). The solvents were then removed on a rotary evaporator to give a white slurry. The slurry was extracted six times with 250 mL portions of ethyl ether, The organic extracts were combined and washed with brine, dried with $MgSO_4$, filtered, and concentrated to give a slightly yellow oil. The thioester product was purified by flash chromatography on $SiO_2$ using 1:1 hexanes:EtOAc until the elution of 4-benzyl-2-oxazolidinone. At that point, the solvent system was switched to 100% EtOAc to give pure fractions of diketide thioester. The product fractions were combined and concentrated to give 14.9 g (89% yield) of title compound. This compound is referred to as the propyl diketide thioester in Example 2.

APCI-MS: m/z 248 (MH+); 1H-NMR (360 MHz, CDCl$_3$): 5.8 (br s, 1H); 3.94 (dt, 1H), 3.46 (m,2H), 3.03 (dt,2H), 2.71 (dq, 1H), 1.97 (s, 3H), 1.50 (m, 2H), 1.37 (m,2H), 1.21 (d,3H), 0.94 (t,3H).

Preparation F: Preparation of (4S)-N-[(2S,3R)-2-Methyl-3-hydroxy-4-pentenoyl]-4-benzyl-2-oxazolidinone A dry, 2 L three-necked round bottomed flask equipped with a 500 mL addition funnel, a low-temperature thermometer, and a stir bar was charged with 20.0 g of propionyl oxazolidinone A, capped with septa and flushed with nitrogen. Anhydrous dichloromethane (100 ml) was added and the resulting solution was cooled to −15° C. in a bath of methanol/ice. Dibutylboron triflate (100 mL of 1.0 M in dichloromethane) was added in a slow stream via the addition funnel at such a rate as to keep the reaction temperature below 3° C. Diisopropylethylamine (17.9 mL) was added dropwise by syringe, again keeping the internal temperature below 3° C. The reaction was then cooled to −65° C. using a dry ice/isopropanol bath. Acrolein was added over 5 min. by syringe. The reaction was allowed to stir for 30 min. after completion of addition.

The reaction was then transferred to an ice bath and the addition funnel was charged with 120 mL (0.1 mol) of a 1 M aqueous phosphate solution, pH 7.0 (the phosphate solution is comprised of equal molar amounts of mono- and dibasic phosphate). The phosphate solution was added as quickly as possible while keeping the reaction temperature below 10° C. The addition funnel was then charged with 400 mL of methanol that were added as quickly as possible while keeping the reaction temperature below 10° C. Finally, the addition funnel was charged with 400 mL of 2:1 methanol:30% hydrogen peroxide by initial dropwise addition to keep the temperature below 10° C. The reaction was stirred for one hour. The solvent was removed using a rotary evaporator, leaving a slurry. The slurry was extracted 4 times with 500 mL portions of ethyl ether. The organic extracts were combined and washed with 250 mL each of saturated sodium bicarbonate and brine, then dried with MgSO$_4$, filtered, and concentrated to give a slightly yellow oil. Trituration with hexane induced crystallization. Recrystallization from ether by addition of hexane resulted in 13.67 g (55% yield) of product.

1H-NMR (360 MHz, CDCl$_3$): 7.2–7.4 (m, 5H); 5.86 (ddd, 1H), 5.35 (dt, 1H), 5.22 (dt, 1H), 4.71 (m, 1H), 4.51 (m, 1H), 4.21 (m, 2H), 3.89 (dq, 1H), 3.26 (dd, 1H), 2.80 (dd, 1H), 1.25 (d, 3H).

Preparation G: Preparation of (2S, 3R)-2-Methyl-3-hydroxy-4-pentenoate N-Acetylcysteamine Thioester N-acetylcysteamine was distilled at 130° C./7 mm Hg to give a colorless liquid at room temperature. A dry, 1 L three-necked round bottomed flask equipped with a 500 mL addition funnel and a stir bar was capped with septa and flushed with nitrogen. The flask was then charged with 7.5 mL of N-acetylcysteamine by syringe and with 500 mL of anhydrous THF by cannula. The reaction was then cooled with a MeOH/ice bath. Butyllithium (44 mL of 1.6 M in hexane) was added dropwise by syringe. A white precipitate formed as the n-BuLi was added. After stirring for 30 min., 35.5 mL (0.071 mol) of trimethylaluminum (2.0 M in hexane) were added drop-wise by syringe. The reaction became clear after addition of trimethylaluminum and was allowed to stir an additional 30 min. (4S)-N-[(2S, 3R)-2-methyl-3-hydroxy-4-pentenoyl]-4-benzyl-2-oxazolidinone from Preparation F (13.6 g) was put under a blanket of nitrogen, dissolved in 50 mL of anhydrous THF, and this solution was then transferred in a slow stream by cannula into the reaction. The resulting reaction mixture turned a yellow-green color and was allowed to stir for 1 hr. The reaction was judged to be finished when starting material could no longer be seen by thin-layer chromatography (ca. 30 min.).

Enough saturated oxalic acid was added to give a neutral reaction with pH paper (approximately 60 mL). The solvents were then removed by rotary evaporator to give a white slurry. The slurry was extracted six times with 250 mL portions of ethyl ether. The organic extracts were combined, washed with brine, dried with MgSO$_4$, filtered, and concentrated to give a slightly yellow oil. The thioester was then purified by flash chromatography on SiO$_2$. The column was run with 1:1 hexanes:ethyl acetate until the elution of oxazolidinone. At that point, the eluent was switched to 100% ethyl acetate to give pure fractions of product. The fractions were combined and concentrated to give 7.7 g (71% yield) of title compound product. This product is referred to as the vinyl diketide thioester in Example 2.

1H-NMR (360 MHz, CDCl$_3$): 5.82 (ddd, 1H), 5.78 (br s, 1H), 5.32 (dt, 1H), 5.21 (dt, 1H), 4.47 (m, 1H), 3.45 (m, 2H), 3.04 (m, 2H), 2.81 (dq, 1H), 1.96 (s, 3H), 1.22 (d, 3H).

Example 2

Preparation of Erythronolides

Preparation A: Preparation of 14,15-Dehydro-6-deoxyerythronolide B

Streptomyces coelicolor CH999/pJRJ2 is described in U.S. patent application Ser. Nos. 08/896,323, filed Jul. 17, 1997, and 08/675,817, filed Jul. 5, 1996, each of which is incorporated herein by reference. Plasmid pJRJ2 encodes a mutated form of DEBS in which the ketosynthase domain of module 1 (KS1) has been inactivated via mutagenesis (KS10). S. coelicolor strains comprising this plasmid that are fed the vinyl diketide thioester prepared in accordance with Example 1 produce 14,15-dehydro-6-deoxyerythronolide B.

Twenty isolates of S. coelicolor CH999/pJRJ2 were tested for their ability to convert the vinyl diketide thioester into 14,15-dehydro-6-deoxyerythronolide B. A frozen spore stock was diluted, plated on R2YE agar plates containing 50 mg/L thiostrepton, and grown at 30° C. for 5 days to obtain single colonies. Each liter of R2YE medium contains 103 g sucrose, 10 g glucose, 10.12 g MgCl$_2$.6H$_2$O, 0.25 g K$_2$SO$_4$, 0.1 g casamino acids, 5 g yeast extract, 5.73 g TES (N-tris[hydroxymethyl]methyl-2-aminoethane sulfonic acid, from Sigma) buffer, 22 g agar (when included), and 2 mL trace elements solution. After autoclaving, 10 mL 5 g/L (0.5%) KH$_2$PO$_4$, 8 mL 2.5 M CaCl$_2$.2H$_2$O, 15 mL 200 g/L (20%) L-proline, and 7 mL 1 N NaOH were added. Each liter of trace elements solution contains 1 mg ZnSO$_4$, 1 mg FeSO$_4$, 1 mg MnCl$_2$, and 1 mg CaCl$_2$. TES was omitted from R2YE media when cultures were grown in pH-controlled bioreactors.

The colonies were patched onto secondary plates for amplification, then spread on fresh R2YE agar plates containing 50 mg/L thiostrepton to create mycelial lawns. Diketide feeding of Streptomyces coelicolor CH999/pJRJ2 to these lawns was performed as previously described (see the patent applications cited supra). The 14,15-dehydro-6-deoxyerythronolide B produced in these cultures was isolated by homogenization and ethyl acetate extraction of the agar on which the culture was grown. Reversed phase HPLC/MS analysis of these extracts was performed using a Beckman 127s solvent module equipped with a Beckman Ultrasphere ODS column (4.6 mm×150 mm) and a gradient of water to acetonitrile as the mobile phase. The 14,15-dehydro-6-deoxyerythronolide B was identified by mass spectrometry (PESciex API100LC) and quantitated using an evaporative light scattering detector (Alltech 500ELSD). High-producing isolates propagated on plates and as frozen spore suspensions were retested to determine their stability during storage.

Of the twenty isolates of Streptomyces coelicolor CH999/pJRJ2 tested for ability to convert the vinyl diketide thioester into 14,15-dehydro-6-deoxyerythronolide B, five isolates were non-producers, and one isolate produced >6 mg/L of product. The high-producing isolate was propagated both on agar medium (restreaking every ~10 days) and as a frozen spore stock. Reisolation of the strain resulted in considerable isolate-to-isolate variation when the strain was stored as a frozen spore stock. When the strain was stored at room temperature on R2YE agar this variability was not observed. Segregation of the production ability of a strain during storage as a frozen spore suspension has been previously observed, although the mechanism by which it occurs is unknown.

Propagation of the strain on agar media and as a frozen mycelial suspension retain an isolate's production capability. Consequently, a cell bank was prepared by inoculating approximately 10 mm$^2$ mycelial patches into 50 mL of R2YE containing 50 $\mu$g/mL thiostrepton and shaken (series 25 New Brunswick coffin shaker) at 200–250 rpm/28–30° C. in a 250 mL baffled flask for 48 hr. The cells were microscopically examined, 25 mL of 90% glycerol was mixed into the culture, and 1 mL aliquots were frozen in liquid nitrogen and stored at −80° C. This procedure was used for storage of both Streptomyces coelicolor and Saccharopolyspora erythraea strains.

14,15-dehydro-6-deoxyerythronolide B can be produced in shake flasks. A seed culture of Streptomyces coelicolor CH999/pJRJ2 was made by adding 1 mL of frozen stock to 50 mL of R2YE containing 50 $\mu$g/mL thiostrepton and ~1 mL/L antifoam B (Baker). Seed cultures of S. coelicolor K39-02/pJRJ2 optionally may contain 50 $\mu$g/mL apramycin. The culture was shaken at 200–250 rpm at 28–30° C. for ~48 hr (Series 25 New Brunswick coffin shaker). A production culture was made by inoculating 10 mL of the seed culture into 500 mL of SO1 medium (optionally, one may use R6 medium with no buffer) containing 50 $\mu$g/mL thiostrepton. Each liter of SO1 medium contained 51.5 g sucrose, 0.25 g K$_2$SO$_4$, 0.1 g casamino acids, 5 g yeast extract, 5.73 g TES buffer, 0.96 g sodium propionate, and 2 mL trace elements solution. After autoclaving, 10 mL 0.5% (5 g/L) KH$_2$PO$_4$, 8 mL 2.5 M CaCl$_2$.6H$_2$O, 7.5 mL 20% (200 g/L) L-proline, and 7 mL 1 N NaOH were added. TES was omitted from SO1 media when cultures were grown in pH-controlled bioreactors.

R6 medium was also used for production cultures. Each liter of R6 medium contained 103 g sucrose, 0.25 g K$_2$SO$_4$, 10.12 g MgCl$_2$.6H$_2$O, 0.1 g casamino acids, 5 g yeast extract, 5.73g TES buffer, 0.96 g sodium propionate, and 2 mL trace elements solution. After autoclaving, 10 mL 0.5% KH$_2$PO$_4$, 8 mL 2.5 M CaCl$_2$.2H$_2$O, 15 mL 20% L-proline, and 7 mL 1 N NaOH were added. TES was omitted from R6 media when cultures were grown in pH-controlled bioreactors.

The culture was grown for 36–48 hr. at 200–250 rpm/28–30° C. The culture was then supplemented with 4-pentynoic acid (Fluka, 25 mg/L) and 1 mM vinyl diketide thioester (3 mL of 4.67 mg/mL diketide in 10% DMSO (Sigma)), and grown for 4 additional days. For diketide feeding in R6 medium, diketide was typically added 24–48 hrs. after inoculation, when the glucose level dropped to 0.5 g/L or lower; glucose concentration can be analyzed to time the feeding more exactly. 14,15-dehydro-6-deoxyerythronolide B was recovered from the culture by solid phase extraction with XAD resin and elution with ethanol.

For large-scale preparation of 14,15-dehydro-6-deoxyerythronolide B, a seed culture of Streptomyces coelicolor K39-02/pJRJ2 was made by inoculating 1 mL of frozen mycelium into a 2.8 L baffled flask containing 500 mL of R2YE, optionally 50 $\mu$g/mL apramycin, 50 $\mu$g/mL thiostrepton, and 1 mL/L antifoam B, and shaking at 150–200 rpm/28–30° C. for about 2 days (Innova floor shaker). A 10 L stirred tank bioreactor (B. Braun A-10) was prepared, filled with 10 L of R6 medium, autoclaved at 121° C. for 30 min., allowed to cool, and then inoculated with 500 mL (2%) of seed culture.

Temperature was maintained at 30° C. with agitation provided by 3 rushton impellers at 500–750 rpm, aeration at 0.5–2 L/min., and pH controlled at 7.00 via automatic addition of 1 N NaOH or 1 N H$_2$SO$_4$. Glucose consumption, dissolved oxygen, pH, and cell mass were monitored. When the glucose concentration dropped below 0.1 g/L, the culture was supplemented with 4-pentynoic acid (25–50 $\mu$g/mL) and 2.5 g of the vinyl diketide thioester in 50 mL of DMSO. Controlled feeding of glucose maintained a glucose concentration of 0–2 g/L (target of 0.5 g/L). Titers of 14,15-dehydro-6-deoxyerythronolide B were monitored by HPLC/MS, and the culture was harvested by centrifugation when a maximum titer was reached. The procedure was scaled to 100 L using a BioLafitte 150 L bioreactor.

The 14,15-dehydro-6-deoxyerythronolide B was purified by solid phase extraction. The fermentation broth was chilled to 4–15° C., and ethanol was added (0.1 L/L broth). The broth was clarified by centrifugation and loaded onto an XAD-16 resin (Rohm and Haas) column (1 kg XAD/1 g 14,15-dehydro-6-deoxyerythronolide B) at a flow rate of 2–4 mL/cm$^2$-min. The loaded resin was washed with 2 column volumes of 15% (v/v) ethanol in water and the 14,15-dehydro-6-deoxyerythronolide B was eluted from the resin with acetone and collected in ½ column volume fractions. The fractions containing 14,15-dehydro-6-deoxyerythronolide B were identified by thin-layer chromatography (ethyl acetate:hexanes 1:1) and HPLC/MS.

The acetone fractions containing 14,15-dehydro-6-deoxyerythronolide B were pooled, and the volatiles were removed under reduced pressure. The resulting aqueous mixture is extracted with ethyl acetate. The ethyl acetate extract was washed with saturated NaHCO$_3$ and brine solutions, dried over sodium or magnesium sulfate, filtered, and concentrated to dryness under reduced pressure. The crude material was purified by chromatography on silica gel using a gradient of hexanes and ethyl acetate. Fractions containing the product were pooled and concentrated to a yellow oil that spontaneously crystallized. Recrystallization from ether-hexane gave pure 14,15-dehydro-6-deoxyerythronolide B. Mass spectrometry shows [M+H]= 385. 13C-NMR (CDCl$_3$, 100 MHz): 213.67 (C9), 177.51 (C1), 134.80 (C14), 116.58 (C15), 79.40 (C3), 76.47 (C5), 74.11 (C13), 70.84 (C11), 43.80 (C2), 43.16 (C10), 41.48 (C12), 39.58 (C8), 37.61 (C7), 37.42 (C4), 35.56 (C6), 16.60 (6Me), 14.55 (2Me), (8Me), 9.20 (12Me), 6.91 (4Me), 6.30 (10Me).

Preparation B: Preparation of 15-Methyl-6-deoxyerythronolide B

A high-producing isolate of Streptomyces coelicolor K39-02/pJRJ2 was used to produce 15-methyl-6-deoxyerythronolide B in shake flasks. A seed culture of Streptomyces coelicolor K39-02/pJRJ2 was made by adding 1 mL of frozen stock to 50 mL of R2YE containing 50 $\mu$g/mL thiostrepton (and, optionally, apramycin). The culture was shaken at 200–250 rpm at 28–30° C. for 36–48 hr. A production culture was made by inoculating 1 mL of the seed culture into 50 mL of SO1 or R6 medium containing 50 $\mu$g mL thiostrepton (and, optionally, apramycin). Antifoam was added at 1 mL/L. The culture was grown for 36–48 hr. at 200–250 rpm/28–30° C. The culture was supplemented with 4-pentynoic acid (Fluka, 25–50 mg/L) and 1 mM propyl diketide thioester (3 mL of 4.67 mg/mL diketide in 10% DMSO (Sigma)), and grown for 4–7 additional days. 15-methyl-6-deoxyerythronolide B was recovered from the culture by extraction with ethyl acetate when maximum titer was reached.

For large-scale preparation of 15-methyl-6-deoxyerythronolide B, a seed culture of Streptomyces coelicolor K39-02/pJRJ2 was made by inoculating 1 mL of frozen mycelium into a 2.8 L baffled flask containing 500 mL of R2YE and shaking at 150–200 rpm/28–30° C. for 2 days. A 10 L stirred tank bioreactor was prepared, filled with 10 L of SO1 or R6 medium, autoclaved at 121° C. for 30 min., allowed to cool, and then inoculated with 400–500 mL of seed culture.

Temperature was maintained at 28–30° C. with agitation provided by 3 rushton impellers at 500–750 rpm, aeration at ~1 L/min., and pH controlled at 7.00 via automatic addition of 1 N NaOH or 1 N $H_2SO_4$. Glucose consumption, dissolved oxygen, pH, and cell mass were monitored. When the glucose concentration dropped below 0.1 g/L, the culture was supplemented with 4-pentynoic acid (25 μg/mL) and 2.5 g of the propyl diketide thioester in 50 mL of DMSO. Controlled feeding of glucose maintained a glucose concentration of ~0.5 g/L. Titers of 15-methyl-6-deoxyerythronolide B were monitored by HPLC/MS, and the culture was harvested by centrifugation when a maximum titer was reached. The procedure was scaled to 100 L using a BioLafitte 150 L bioreactor.

The 15-methyl-6-deoxyerythronolide B was purified by solid phase extraction. Fermentation broth was cooled to 4–15° C., and ethanol was added (0.1 L/L broth). The broth was clarified by centrifugation and loaded onto an XAD-16 resin (Rohm and Haas) column (1 kg XAD/1 g 15-methyl-6-deoxyerythronolide B) at a flow rate of 2–4 mL/cm²-min. The loaded resin was washed with 2 column volumes of 15% (v/v) ethanol in water and the 15-methyl-6-deoxyerythronolide B was eluted from the resin with acetone and collected in +e,fra 2+ee column volume fractions. The fractions containing 15-methyl-6-deoxyerythronolide B were identified by thin-layer chromatography (ethyl acetate:hexanes 1:1) and HPLC/MS.

The acetone fractions containing 15-methyl-6-deoxyerythronolide B were pooled, and the volatiles were removed under reduced pressure. The resulting aqueous mixture is extracted with ethyl acetate. The ethyl acetate extract was washed with saturated $NaH_2CO_3$ and brine solutions, dried over sodium or magnesium sulfate, filtered, and concentrated to dryness under reduced pressure. The crude material was purified by chromatography on silica gel using a gradient of hexanes and ethyl acetate. Fractions containing the product were pooled and concentrated to a yellow oil that spontaneously crystallized. Recrystallization from ether-hexane gave pure 15-methyl-6-deoxyerythronolide B. Mass spectrometry shows [M+H]=401.

Preparation C: Preparation of 14-nor-6-Deoxyerythronolide B

U.S. Pat. No. 5,712,146, incorporated herein by reference, describes the preparation of a recombinant host cell, *Streptomyces coelicolor* CH999/pCK7. The patent reports that, when the recombinant strain is grown on R2YE medium, the strain produces a mixture of 6-deoxyerythronolide B and 14-nor-6-deoxyerythronolide B (also known as 8,8a-deoxyoleandolide). A related strain, *S. coelicolor* 27-26/pKOS011-26 contains a modified pCK7 plasmid and a recombinant ptpA gene.

A high-producing isolate of *Streptomyces coelicolor* 27-26/pKOS011-26 was used to produce 14-nor-6-deoxyerythronolide B in shake flasks. A seed culture of *Streptomyces coelicolor* 27-26/pKOS011-26 was made by adding 1 mL of frozen stock to 50 mL of R2YE containing 50 μg/mL of thiostrepton (and, optionally, apramycin). The culture was shaken at 200–250 rpm at 28–30° C. for 36–48 hr. A production culture was made by inoculating 1 mL of the seed culture into 50 mL of SO1 medium containing 50 μg/mL thiostrepton (and, optionally, apramycin). The culture was grown for 36–48 hr. at 200–250 rpm/28–30° C. The culture was supplemented with 4-pentynoic acid (Fluka, 25–50 mg/L) and grown for 4 additional days. 14-nor-6-deoxyerythronolide B was recovered from the culture by extraction with ethyl acetate.

For large-scale preparation of 14-nor-6-deoxyerythronolide B, a seed culture of *Streptomyces coelicolor* 27-26/pKOS011-26 was made by inoculating 1 mL of frozen mycelium into a 2.8 L baffled flask containing 500 mL of R2YE and shaking at 150–200 rpm/28–30° C. for 36–48 hr. A 10 L stirred tank bioreactor was prepared, filled with 10 L of R2YE medium without glucose, autoclaved at 121° C. for 30 min., allowed to cool, and then inoculated with 400–500 mL of seed culture. Antifoam was added at 1 mL/L.

Temperature was maintained at 28–30° C. with agitation provided by 3 rushton impellers at 500–750 rpm, aeration at ~1 L/min., and pH controlled at 7.00 via automatic addition of 1 N NaOH or 1 N $H_2SO_4$. Glucose consumption, dissolved oxygen, pH, and cell mass were monitored. Controlled feeding of glucose maintained a glucose concentration of ~0.5 g/L. Titers of 14-nor-6-deoxyerythronolide B were monitored by HPLC/MS, and the culture was harvested by centrifugation when a maximum titer was reached. The procedure was scaled to 100 L using a BioLafitte 150 L bioreactor.

The 14-nor-6-deoxyerythronolide B was purified by solid phase extraction. Fermentation broth was chilled to 4–15° C., and ethanol was added (0.1 L/L broth). The broth was clarified by centrifugation and loaded onto an XAD-16 resin (Rohm and Haas) column (1 kg XAD/1 g 14-nor-6-deoxyerythronolide B) at a flow rate of 2–4 mL/cm²-min. The loaded resin was washed with 2 column volumes of 15% (v/v) ethanol in water and the 14-nor-6-deoxyerythronolide B was eluted from the resin with acetone and collected in ½ column volume fractions. The fractions containing 14-nor-6-deoxyerythronolide B were identified by thin-layer chromatography (ethyl acetate:hexanes 1:1) and HPLC/MS.

The acetone fractions containing 14-nor-6-deoxyerythronolide B were pooled, and the volatiles were removed under reduced pressure. The resulting aqueous mixture is extracted with ethyl acetate. The ethyl acetate extract was washed with saturated $NaH_2CO_3$ and brine solutions, dried over sodium or magnesium sulfate, filtered, and concentrated to dryness under reduced pressure. The crude material was purified by flash chromatography using $SiO_2$ columns developed with ethyl acetate/hexanes. Recrystallization from ether-hexane gave pure 15-methyl-6-deoxyerythronolide B. Mass spectrometry shows [M+H]=373.

Example 3

Preparation of Erythromycins

The 6-dEB derivative compounds produced in Example 2, Preparations A–C are converted to erythromycin derivatives using a recombinant strain of *Saccharopolyspora erythraea*. For production of erythromycins having both the 6 and 12 hydroxyl groups, the *S. erythraea* strain used was K40-67. This strain was created by transforming an *S. erythraea* strain capable of producing high levels of erythromycin A with a pWHM3-derived plasmid comprising a mutated eryA1 sequence encoding an inactivated KS1 domain. By homologous recombination, the resulting transformants were rendered incapable of producing 6-deoxyerythronolide B. For production of erythromycin derivatives having only the 12-hydroxyl group, the *S. erythraea* strain used was K39-07. This strain was constructed from strain K40-67 by disruption of the eryF hydroxylase gene. Both strains were fermented under substantially similar conditions, as described below.

Fermentations were conducted in 10 L (and 150 L) bioreactors. A 1 mL aliquot of frozen *S. erythraea* K40-67 mycelium was used to inoculate a seed culture in 500 mL of R2YE medium. The culture was shaken at 150–200 rpm/28–30° C. in a 2.8 L baffled Fembach flask for ~48 hr. A 10

L stirred tank bioreactor was prepared, filled with 10 L of R2YE medium (70 L for the 150 L fermentation), autoclaved at 121° C. for 45 min., allowed to cool, and then inoculated with 200 mL (1.4 L for the 150 L fermentation) of seed culture. Temperature was maintained at 28–30° C. with agitation provided by 2 rushton impellers at 500–700 rpm, aeration at 1 L/min., and pH controlled at 7.20 via automatic addition of 1 N NaOH or 1 N $H_2SO_4$. Foam was suppressed by addition of antifoam at 1 mL/L. The pH was controlled to avoid potential product degradation into enol ether and spiroketal. Sucrose consumption, glucose evolution, dissolved oxygen, pH, and absorbance at 600 nm (cell mass) were monitored. After 24–36 hr., the culture was fed 300 mg (1.62 g for the 150 L fermentation) of a 6-dEB derivative compound prepared in accordance with Preparations A–C of this Example dissolved in 3 mL (15 mL for the 150 L fermentation) of 100% ethanol. Fermentation continued for ~68–85 additional hr., and the fermentation broth was harvested by centrifigation. Titers of erythromycin A, B, C, and D analogs during the course of the fermentation were determined by electrospray MS analysis.

The compounds produced were purified by solid phase extraction. Fermentation broth was brought to pH 8.0 by addition of NaOH and chilled to 4–15° C., and ethanol was added (0.1 L/L broth). The broth was clarified by centrifugation and loaded onto an XAD-16 resin (Rohm and Haas) column (1 kg XAD/1 g erythromycin derivative) at a flow rate of 2–4 mL/cm²-min. The loaded resin was washed with 2 column volumes of 15% (v/v) ethanol in water and the erythromycin derivative was eluted from the resin with acetone and collected in ½ column volume fractions. The fractions containing the erythromycin derivative were identified by thin-layer chromatography and HPLC/MS.

The acetone fractions containing the erythromycin derivative were pooled, and the volatiles were removed under reduced pressure. The resulting aqueous mixture was extracted with ethyl acetate. The ethyl acetate extract was washed with saturated $NaH_2CO_3$ and brine solutions, dried over sodium or magnesium sulfate, filtered, and concentrated to dryness under reduced pressure. The crude material was purified by flash chromatography (methylene chloride/methanol/triethylamine). This material served as starting material for the chemical derivatization procedures described in the following examples. Pure products may be obtained through the use of centrifugal countercurrent distribution (e.g., using an Ito Coil Planet Centrifuge as described in WO 91/16334, incorporated herein by reference).

The compounds produced by this methodology were: (1) 14-nor erythromycin A; (ii) 14,15-dehydro-erythromycin A; (iii) 15-methyl-erythromycin A; (iv) 14-nor-6-deoxy-erythromycin A; (v) 14,15-dehydro-6-deoxy-erythromycin A; and (vi) 15-methyl-6-deoxy-erythromycin A. When used to make 3-descladinose-3-oxo-derivatives, the erythromycin A derivatives were not separated from the erythromycin C derivatives; instead, mixtures of the A and C compounds were used as starting materials for chemical derivatization.

Example 4

Preparation A: 14-Norerythromycin A 9-Oxime

A solution of 14-norerythromycin A (0.621 g, 80% pure), hydroxylamine (0.5 ml of 50% aqueous solution) and acetic acid (0.2 ml) in isopropanol (2 ml) was kept at 50° C. for 22 hours. It was extracted with chloroform/ethanol (3/2), washed with sodium bicarbonate, brine, and dried over $MgSO_4$. Filtration and evaporation in vacuo yielded a crude product (0.65 g) as a white solid which was used directly for next transformation.

Preparation B: 14-Norerythromycin A 9-[O-(1-Isopropoxycyclohexyl)]oxime

To a solution of above crude 14-noreythromycin A 9-oxime (0.65 g) and 1,1-diisopropoxy-cyclohexanone (0.95 ml) in methylene chloride (2 ml) was added pyridinium p-toluenesulfonate (PPTS) (0.333 g) in methylene chloride (2 ml). After stirring overnight, the mixture was extracted (chloroform/ethanol 3:2), washed ($NaHCO_3$—$H_2O$, brine), and dried ($MgSO_4$). After filtration and evaporation in vacuo, the crude product was repeatedly driven with toluene and isopropanol to yield 0.74 g of product, which was used directly for next reaction.

Preparation C: 2',4"-bis(O-Trimethylsilyl)-14-norerythromycin A 9-[O-(1-Isopropoxy-cyclohexyl)]oxime To a solution of 14-norerythromycin A 9-[O-(1-isopropoxycyclohexyl)]oxime (0.74 g) in methylene chloride (6 ml) was added a solution of trimethylsilyl imidazole (0.33 ml) and trimethylsilyl chloride (0.18 ml) in methylene chloride (2 ml) at 0° C. After 5 minute stirring, ethyl acetate was added, washed ($NaHCO_3$—$H_2O$, brine), and dried ($MgSO_4$). Flash chromatography on silica gel (10:1 hexanes:acetone, 1% triethylamine) afforded pure product as a white solid (0.50 g). Mass spectrometry reveals [M+H⁺]= 1020.

Preparation D: 2',4"-bis-(O-Trimethylsilyl)-6-O-methyl-14-norerythromycin A 9-[O-(1-Isopropoxycyclohexyl)]oxime A solution of 2',4"-bis-O-trimethylsilyl-14-norerythromycin A 9-[O-(1-isopropoxy-cyclohexyl)]oxime (0.3 g, 0.29 mmol) in 1:1 methylsulfoxide/tetrahydrofuran (DMSO/THF) (1.4 ml) was treated with 0.3 ml of a 2 M solution of methyl bromide in ether and cooled to 10° C. A mixture of 1 M solution of potassium tert-butoxide in THF (0.6 ml) and DMSO (0.6 ml) was added over 6 hours using a syringe pump. The reaction was then diluted with ethyl acetate, washed with saturated $NaHCO_3$, brine, and dried over $MgSO_4$. Filtration and evaporation in vacuo yielded the product (0.29 g) as a white solid. Mass spectrometry reveals [M+H⁺]=1034.

Preparation E: 6-O-Methyl-14-norerythromycin A 9-Oxime

A mixture of 6-O-methyl-2',4"-bis-O-trimethylsilyl-14-norerythromycin A 9-[O-(1-isopropoxycyclohexyl)]oxime (0.29 g), acetic acid (3.6 ml), acetonitrile (6 ml) and water (3 ml) was stirred at ambient temperature for 4.5 hours. The mixture was driven to dryness using toluene to give a crude product as white solid (0.24 g), which was used directly for next step without further purification.

Preparation F: 6-O-Methyl-14-norerythromycin A

A mixture of 6-O-methyl-14-norerythromycin A 9-oxime (0.24 g), sodium hydrosulfite (0.45 g, 85% pure), water (3 ml), ethanol (3 ml) and formic acid (0.07 ml) was kept at 85° C. for 8 hours. The reaction was brought to pH 8 with 1 N NaOH and extracted with ethyl acetate. The organic extract was washed with brine, dried over $MgSO_4$, filtered, and concentrated to yield a crude product as a white solid (0.2 g). Mass spectrometry reveals [M+H⁺]=735.

Example 5

Preparation A: 14,15-Dehydroerythromycin A 9-Oxime

A suspension of 14,15-dehydroerythromycin A (1.984 g, 47% purity, 1.2 mmol) in 6 mL of 2-propanol was treated with 1.97 mL of 50% aqueous hydroxylamine and stirred until dissolved. Acetic acid (0.62 mL) was added and the mixture was stirred for 25 hours at 50 ° C. Upon cooling to ambient temperature, saturated $NaHCO_3$ was added and the mixture was concentrated en vacuo to remove isopropanol. The resulting aqueous mixture was extracted three times with 250-mL portions of $CHCl_3$. The organic extracts were combined, washed with saturated $NaHCO_3$, water, and brine, then dried over $MgSO_4$, filtered, and concentrated to yield 0.92 g of product.

Preparation B: 14,15-Dehydroerythromycin A 9-[O-(1-Isopropoxycyclohexyl)]oxime

The oxime from (A) (0.92 g) was dissolved in 6.2 mL of $CH_2Cl_2$ and treated with 1,1-diisopropoxycyclohexane (1.23 g) and pyridinium p-toluenesulfonate (0.464 gm) for 15 hours at ambient temperature. The mixture was diluted with 160 mL of CH$_2$Cl$_2$, then washed sequentially with saturated NaHCO$_3$, water, and brine. The organic phase was dried with MgSO$_4$, filtered, and evaporated to yield a brown syrup. Chromatography on silica gel (gradient from toluene to 1:1 toluene/acetone +1% Et$_3$N) yielded 0.998 g of product.

Preparation C: 2',4"-bis(O-Trimethylsilyl)-14,15-dehydroerythromycin A 9-[O-(1-Isopropoxycyclohexyl)]oxime A solution of 14,15-dehydroerythromycin A 9-[O-(1-isopropoxycyclohexyl)]oxime (998 mg, 9.96) in 11.25 mL of CH$_2$Cl$_2$ was cooled on ice under inert atmosphere and treated with a solution of chlorotrimethylsilane (0.24 mL) and 1-trimethylsilylimidazole (0.44 mL). After 30 minutes, the reaction was diluted with 250 mL of ethyl acetate and washed sequentially with saturated NaHCO$_3$, water, and brine. The organic phase was dried with MgSO$_4$, filtered, and evaporated to yield 1.002 g of product.

Preparation D: 2',4"-bis(O-Trimethylsilyl)-6-O-methyl-14,15-dehydroerythromycin A 9-[O-(1-Isopropoxycyclohexyl)]oxime A solution of 2',4"-bis-O-trimethylsilyl-14,15-dehydroerythromycin A 9-[O-(1-isopropoxycyclohexyl)]oxime (1.00 g, 20.7 mmol) in 9.69 mL of 1:1 tetrahydrofuran/methylsulfoxide was cooled to 10 °C. and treated with 0.97 mL of 2.0 M methyl bromide in ether under inert atmosphere. A mixture of methylsulfoxide (1.94 mL) and 1.0 M potassium tert-butoxide in tetrahydrofuran (1.94 mL) was added slowly. The reaction was monitored by thin-layer chromatography (silica gel, 10:1 toluene/acetone), and was judged complete after addition of 1.6 molar equivalents of base. The reaction was diluted with 200 mL of ethyl acetate and 70 mL of saturated NaHCO$_3$. The mixture was transferred to a separatory funnel, diluted with 850 mL of ethyl acetate and 280 mL of saturated NaHCO$_3$, then washed sequentially with water and brine. The organic phase was dried with MgSO$_4$, filtered through Celite, and evaporated to yield 21.2 g of crude 6-O-methyl-2',4"-bis-O-trimethylsilyl-14,15-dehydroerythromycin A 9-[O-(1-isopropoxycyclohexyl)]oxime. This was carried on without further purification.

Preparation E: 6-O-Methyl-14,15-dehydroerythromycin A 9-Oxime

A solution of 6-O-methyl-2', 4"-bis-O-trimethylsilyl-14,15-dehydroerythromycin A 9-[O-(1-isopropoxycyclohexyl)]oxime (1.0 g) in 9.8 mL of 2:1 acetonitrile/water was treated with 5.3 mL of acetic acid, and stirred for 8 hours at ambient temperature. The mixture was concentrated en vacuo, then repeatedly concentrated after addition of toluene to yield 0.797 g of crude 6-O-methyl-14,15-dehydroerythromycin A 9-oxime.

Preparation F: 6-O-Methyl-14,15-dehydroerythromycin A

A solution of 6-O-methyl-14,15-dehydroerythromycin A 9-oxime (0.797 g) and sodium hydrosulfite (85%, 1.02 g) in 7.5 mL of 1:1 ethanol/water was placed under inert atmosphere. Formic acid (0.186 mL) was added dropwise, and the mixture was stirred at 80° C. for 3 hours. After cooling to ambient temperature, the reaction was adjusted to pH 10 with 6 N NaOH and extracted three times with 150-mL portions of ethyl acetate. The organic extracts were combined and washed sequentially with saturated NaHCO$_3$, water, and brine. The organic phase was dried with MgSO$_4$, filtered, and evaporated to yield 0.68 g of 6-O-methyl-14,15-dehydroerythromycin A suitable for further conversion.

Example 6

Preparation A: 15-Methylerythromycin A 9-Oxime

A suspension of 15-methylerythromycin A (20.0 g, 85% purity, 22.6 mmol) in 40 mL of 2-propanol was treated with 20.5 mL of 50% aqueous hydroxylamine and stirred until dissolved. Acetic acid (6.41 mL) was added and the mixture was stirred for 15 hours at 50° C. Upon cooling to ambient temperature, saturated NaHCO$_3$ was added and the mixture was concentrated en vacuo to remove isopropanol. The resulting aqueous mixture was extracted three times with 250-mL portions of CHCl$_3$. The organic extracts were combined, washed with saturated NaHCO$_3$, water, and brine, then dried over MgSO$_4$, filtered, and concentrated to yield 20.5 g of crude product. Analysis by LC/MS revealed a 94:6 mixture of E and Z oximes, [M+H]$^+$=764.

Preparation B: 15-Methylerythromycin A 9-[O-(1-Isonropoxycyclohexyl)]oxime

The crude oxime from above (20.5 g) was dissolved in 55 mL of CH$_2$Cl$_2$ and treated with 1,1-diisopropoxycyclohexane (27.3 mL) and pyridinium p-toluenesulfonate (9.8 gm) for 15 hours at ambient temperature. The mixture was diluted with 160 mL of CH$_2$Cl$_2$, then washed sequentially with saturated NaHCO$_3$, water, and brine. The organic phase was dried with MgSO$_4$, filtered, and evaporated to yield a brown syrup. Chromatography on silica gel (gradient from 2:1 to 3:2 hexanes/acetone+1% Et$_3$N) yielded 18.0 g of product.

Preparation C: 2',4"-bis-O-Trimethylsilyl-15-methylerythromycin A 9-[O-(1-Isopropoxycyclohexyl)]oxime A solution of 15-Methylerythromycin A 9-[O-(1-isopropoxycyclohexyl)]oxime (9.00 g, 9.96 mmol) in 25 mL of CH$_2$Cl$_2$ was cooled on ice under inert atmosphere and treated with a solution of chlorotrimethylsilane (1.89 mL) and 1-trimethylsilylimidazole (3.65 mL) in 8 mL of CH$_2$Cl$_2$. After 30 minutes, the reaction was diluted with 250 mL of ethyl acetate and washed sequentially with saturated NaHCO$_3$, water, and brine. The organic phase was dried with MgSO$_4$, filtered, and evaporated. The crude product was purified by silica gel chromatography (gradient from hexanes to 10:1 hexanes/acetone+1% Et$_3$N), yielding 7.8 g of product.

Preparation D: 2',4"-bis-O-Trimethylsilyl-6-O-methyl-15-methylerythromycin A 9-[O-(1-Isopropoxycyclohexyl)]oxime A solution of 2',4"-bis-O-trimethylsilyl-15-methylerythromycin A 9-[O-(1-isopropoxycyclohexyl)]oxime (21.7 g, 20.7 mmol) in 41.4 mL of tetrahydrofuran was cooled to 10 °C. and treated with 41.4 mL of methylsulfoxide and 20.7 mL of 2.0 M methyl bromide in ether under inert atmosphere. A mixture of methylsulfoxide (41.4 mL) and 1.0 M potassium tert-butoxide in tetrahydrofuran (41.4 mL) was added at a rate of ca. 20 mL per hour. The reaction was monitored by thin-layer chromatography (silica gel, 10:1 toluene/acetone), and was judged complete after addition of 1.6 molar equivalents of base. The reaction was diluted with 200 mL of ethyl acetate and 70 mL of saturated NaHCO$_3$. The mixture was transferred to a separatory funnel, diluted with 850 mL of ethyl acetate and 280 mL of saturated NaHCO$_3$, then washed sequentially with water and brine. The organic phase was dried with MgSO$_4$, filtered through Celite, and evaporated to yield 21.2 g of crude 6-O-methyl- 2',4"-bis-O-trimethylsilyl-15-methylerythromycin A 9-[O-(1-isopropoxycyclohexyl)]oxime. This was carried on without further purification.

Preparation E: 6-O-Methyl-15-methylerythromycin A 9-Oxime

A solution of 6-O-methyl-2',4"-bis-O-trimethylsilyl-15-methylerythromycin A 9-[O-(1-isopropoxycyclohexyl)]oxime (21.2 g) in 110 mL of acetonitrile was treated with 55 mL of water and 67 mL of acetic acid, and stirred for 8 hours at ambient temperature. The mixture was concentrated en vacuo, then repeatedly concentrated after addition of toluene to yield 19.7 g of 6-O-methyl-15-methylerythromycin A 9-oxime.

Preparation F: 6-O-Methyl-15-methylerythromycin A

A solution of 6-O-methyl-15-methylerythromycin A 9-oxime (19.7 g) and sodium hydrosulfite (85%, 23.1 g) in 280 mL of 1:1 ethanol/water was placed under inert atmosphere. Formic acid (3.75 mL) was added dropwise, and the mixture was stirred at 80° C. for 4.5 hours. After cooling to ambient temperature, the reaction was treated with saturated NaHCO$_3$ and extracted three times with 400-mL portions of ethyl acetate. The organic extracts were combined and washed sequentially with saturated NaHCO$_3$, water, and brine. The organic phase was dried with MgSO$_4$, filtered, and evaporated to yield 15.1 g of 6-O-methyl-15-methylerythromycin A suitable for further conversion.

Example 7

Preparation A: 6-O-Methyl-3-descladinosyl-14-norerythromycin A

A mixture of 6-O-methyl-14-norerythromycin A (77 mg), 0.073 ml of 12 N HCl and water (2 ml) was stirred at ambient temperature for 3 hours. The mixture was brought to pH 8 with 8 N KOH, and extracted with ethyl acetate. The organic extract was washed with brine, dried with MgSO$_4$, filtered, and evaporated. The residue was chromatographed on silica gel (3:1/hexanes:acetone, 1% triethylamine) to give pure product as a white solid (42 mg). Mass spectrometry reveals [M+H$^+$]=576.

Preparation B: 2'-O-Acetyl-6-O-methyl-3-descladinosyl-14-norerythromycin A

A mixture of 6-O-methyl-3-descladinosyl-14-norerythromycin A (73 mg), potassium carbonate (20 mg), acetic anhydride (14 μl) and acetone (1 ml) was stirred at ambient temperature for 18 hours. Ethyl acetate was added, washed with water and brine, dried over MgSO$_4$, filtered, and evaporated. The residue was chromatographed on silica gel (3:1/hexanes:acetone, 1% triethylamine) to yield the pure product (71 mg) as a white solid. Mass spectrometry reveals [M+H$^+$]=618.

Preparation C: 2'-O-Acetyl-6-O-methyl-3-descladinosyl-3-oxo-14-norerythromycin A A solution of 2'-O-acetyl-6-O-methyl-3-descladinosyl-14-norerythromycin A (99 mg) and 1-(3-dimethylaminopropyl)-3-ethylcarbodiimide(EDC) hydrochloride (206 mg) in dichloromethane (2 ml) was treated with DMSO (0.21 ml) and cooled to 5° C. A solution of pyridinium trifluoroacetate (208 mg) in dichloromethane (2 ml) was added via a syringe pump in 4 hours. Ethyl acetate was then added, washed with saturated NaHCO$_3$, water, brine, and dried over MgSO$_4$, filtered, and evaporated. The residue was chromatographed on silica gel (3:1/hexanes:acetone, 1% triethylamine) to yield the pure product (94 mg) as a white solid. Mass spectrometry reveals [M+H$^+$]=616.

Preparation D: 2'-O-Acetyl-6-O-methyl-3-descladinosyl-3-oxo-11-O-methanesulfonyl-14-norerythromycin A To a solution of 2'-O-Acetyl-6-O-methyl-3-descladinosyl-3-oxo-14-norerythromycin A(93 mg) in dry pyridine (1 ml) was added methanesulfonyl chloride (0.057 ml) at 5° C. After 3 hours at 5° C., the reaction was warmed to ambient temperature and kept for an additional 15 hours. The mixture was diluted with ethyl acetate, washed with saturated NaHCO$_3$(2×), water (3×), brine, and dried over MgSO$_4$, filtered, and evaporated. The residue was chromatographed on silica gel (2:1/hexanes:acetone, 1% triethylamine) to yield the pure product (72 mg) as a white solid. Mass spectrometry reveals [M+H$^+$]=695.

Preparation E: 2'-O-Acetyl-6-O-methyl-3-descladinosyl-3-oxo-10,11-anhydro-14-norerythromycin A A solution of 2'-O-acetyl-6-O-methyl-3-descladinosyl-3-oxo-11-O-methanesulfonyl-14-norerythromycin A (73 mg) in acetone (1 ml) was treated with diazabicycloundecene (32 μl) at ambient temperature for 18 hours. The mixture was diluted with ethyl acetate, washed with saturated NaHCO$_3$, water, brine, and dried over MgSO$_4$, filtered, and evaporated. The residue was chromatographed on silica gel (2:1/hexanes:acetone, 1% triethylamine) to yield the pure product (50 mg) as a white solid. Mass spectrometry reveals [M+H$^+$]=598. $^{13}$C-NMR (CDCl$_3$, 100 MHz): δ 207.02, 204.50, 169.63, 168.72, 142.52, 139.40, 101.87, 80.61, 80.02, 77.14, 72.66, 71.48, 69.09, 63.56, 51.35, 50.56, 47.12, 40.61, 39.73, 37.36, 30.36, 21.32, 21.06, 20.96, 20.67, 18.45, 14.34, 13.89, 13.55, 13.45.

Example 8

Preparation A: 2'-O-Benzoyl-6-O-methyl-14,15-dehydroerythromycin A

A solution of 6-O-methyl-14,15-dehydroerythromycin A (668 mg), benzoic anhydride (385 mg), and triethylamine (0.25 mL) in 3.6 mL of CH$_2$Cl$_2$ was stirred for 2 days. After addition of saturated NaHCO$_3$, the mixture was extracted three times with CH$_2$Cl$_2$. The organic extracts were combined and evaporated to dryness, and the product was purified by silica chromatography (90:9:1 toluene/acetone/Et$_3$N) to give 477 mg of product; LC–MS shows [M+H]$^+$=850.6.

Preparation B: 2'-O-Benzoyl-6-O-methyl-4",11-bis(O-methanesulfonyl)-14,15-dehydroerythromycin A A solution of 2'-O-benzoyl-6-O-methyl- 14,15-dehydroerythromycin A (549 mg) and methanesulfonyl chloride (0.50 mL) in 2.39 mL of pyridine was stirred for 24 hours, then diluted with CH$_2$Cl$_2$ and saturated NaHCO$_3$. The mixture was extracted three times with CH$_2$Cl$_2$. The organic extracts were combined and evaporated to dryness, and the product was purified by silica chromatography (90:9:1 toluene/acetone/Et$_3$N) to give 530 mg of product; LC–MS shows [M+H]$^+$=1006.5.

Preparation C: 2'-O-Benzoyl-6-O-methyl-4"-O-methanesulfonyl-10,11-anhydro-14,15-dehydroerythromycin A A mixture of 2'-O-benzoyl-6-O-methyl-4",11-bis(O-methanesulfonyl)14,15-dehydroerythromycin A (59 mg) and diazabicycloundecene (0.018 mL) in 0.195 mL of acetone was stirred for 24 hours, then dried in vacuo. The product was purified by silica chromatography (90:9:1 toluene/acetone/Et$_3$N) to give 50 mg of product; LC–MS shows [M+H]$^+$=910.5.

Preparation D: 2'-O-Benzoyl-6-O-methyl-3-descladinosyl-10,11-anhydro- 14,15-dehydroerythromycin A A mixture of 2'-O-benzoyl-6-O-methyl-4"-O-methanesulfonyl-10,11-anhydro-14,15-dehydroerythromycin A (337 mg), 1.5 mL of acetonitrile, and 6.9 mL of 3 N HCl was stirred for 22 hours. The acetonitrile was removed in vacuo, the pH of the aqueous residue was adjusted to 12 by addition of NaOH, and the product was extracted using 4 portions of CH$_2$Cl$_2$. The combined extracts were dried and evaporated. The product was purified by silica chromatography (gradient from 96:4 CH$_2$Cl$_2$/MeOH to 95:4:1 CH$_2$Cl$_2$/MeOH/Et$_3$N) to give 197 mg, [M+H]$^+$=674.4.

Preparation E: 2'-O-Benzoyl-6-O-methyl-3-descladinosyl-3-oxo-10,11-anhydro-14,15-dehydroerythromycin A A suspension of 2'-O-benzoyl-6-O-methyl-3-descladinosyl-10,11-anhydro-14,15-dehydroerythromycin A (226 mg) and the Dess-Martin periodinane (427 mg) in 14.6 mL of CH$_2$Cl$_2$ (14.6 mL) was stirred for 1 hour. The mixture was diluted with CH$_2$Cl$_2$ and saturated NaHCO$_3$. The product was extracted using 3 portions of CH$_2$Cl$_2$, and the extracts were combined, dried, and evaporated. Silica gel chromatography (90:9:1 toluene/acetone/Et$_3$N) yielded the product, 168 mg. [M+H]$^+$=672.4. $^{13}$C-NMR (CDCl$_3$, 100 MHz): δ 206.78, 203 (br), 168.19, 165.08, 141.36, 139.58, 132.74, 131.51, 130.46, 129.79, 128.25, 120.18, 102.09, 80.79, 80.40, 78.70, 72.52, 71.91, 69.19, 63.76, 51.10, 50.54, 47.08, 40.73, 39.87, 37.77, 31.23, 22.13, 20.98, 18.52, 14.28, 14.15, 13.55.

Preparation A: 6-O-Methyl-3-descladinosyl-15-methylerythromycin A

A mixture of 6-O-methyl-15-methylerythromycin A (15.1 g) and 280 mL of 0.5 N HCl was stirred at ambient temperature for 3 hours. The pH was adjusted to 9 by addition of 6 N NaOH, and the resulting precipitate was collected by vacuum filtration, washed with water, and dried. The filtrate was extracted three times with 400-mL portions of ethyl acetate. The organic extracts were combined, washed sequentially with saturated $NaHCO_3$, water, and brine, then dried over $MgSO_4$, filtered, and evaporated to provide further product. The combined crude products were chromatographed on silica gel to yield 9.35 g of pure 6-O-methyl-3-descladinosyl-15-methylerythromycin A. ES-LC/MS shows $[M+H]^-=605$.

Preparation B: 2'-O-Acetyl-6-O-methyl-3-descladinosyl-15-methylerythromycin A

A solution of acetic anhydride (2.92 mL) in 35 mL of ethyl acetate was added dropwise to a solution of 6-O-methyl-3-descladinosyl-15-methylerythromycin A (9.35 g) in 40 mL of ethyl acetate. The mixture was stirred for 30 minutes after completion of addition, then concentrated. Chromatography on silica gel (2:1 hexanes/acetone) gave 8.35 g of 2'-O-acetyl-6-O-methyl-3-descladinosyl-15-methylerythromycin A. ES–LC/MS shows $[M+H]^-=647$.

Preparation C: 2'-O-Acetyl-6-O-methyl-3-descladinosyl-3-oxo-15-methylerythromycin A A solution of 2'-O-acetyl-6-O-methyl-3-descladinosyl-15-methylerythromycin A (8.3 g) and 1-ethyl-3-(dimethylaminopropyl)carbodiimide hydrochloride (16.51 g) in 64 mL of dichloromethane and 15.47 mL of methylsulfoxide was placed under inert atmosphere and cooled on ice. A solution of pyridinium trifluoroacetate (16.63 g) in 64 mL of dichloromethane was added at a rate such that addition would be complete in 4 hours, and the reaction was monitored by thin-layer chromatography. Complete reaction was observed after addition of 73% of the solution, and so the reaction was then quenched by addition of 600 mL of ethyl acetate and 200 mL of saturated $NaHCO_3$. The organic layer was collected and washed sequentially with saturated $NaHCO_3$, water, and brine, then dried over $MgSO_4$, filtered, and evaporated to yield 8.4 g of crude product. Chromatography on silica gel (3:1 hexanes/acetone) gave 6.75 g of 2'-O-acetyl-6-O-methyl-3-descladinosyl-3-oxo-15-methylerythromycin A. ES–LC MS shows $[M+H]^-=645$.

Preparation D: 2'-O-Acetyl-6-O-methyl-3-descladinosyl-3-oxo-11-methanesulfonyl-15-methylerythromycin A Methanesulfonylchloride (5.68 mL) was added dropwise to a solution of 2'-O-acetyl-6-O-methyl-3-descladinosyl-3-oxo-15-methylerythromycin A (6.73 g) in 35 mL of pyridine at 0° C. The mixture was brought to ambient temperature and quenched by addition of 700 mL of ethyl acetate and 200 mL of saturated $NaHCO_3$. The organic layer was collected and washed sequentially with saturated $NaHCO_3$, water, and brine, then dried over $MgSO_4$, filtered, and evaporated to yield 8.2 g of crude product. Chromatography on silica gel (5:2 hexanes/acetone) gave 5.04 g of 2'-O-acetyl-6-O-methyl-3-descladinosyl-3-oxo-11-O-methanesulfonyl-15-methylerythromycin A. ES–LC/MS shows $[M+H]^-=723$.

Preparation E: 2'-O-Acetyl-6-O-methyl-3-descladinosyl-3-oxo-10,11-anhydro-15-methylerythromycin A 1,8-Diazabicyclo[5.4.0]undec-7-ene (5.22 mL) was added dropwise to a solution of 2'-O-acetyl-6-O-methyl-3-descladinosyl-3-oxo-11-O-methanesulfonyl-15-methylerythromycin A (5.03 g) in 23 mL of acetone. The solution was concentrated after 4.5 hours, and the residue was chromatographed on silica gel (5:2 hexanes/acetone) to give 3.72 g of 2'-O-acetyl-6-O-methyl-3-descladinosyl-3-oxo-10,11-anhydro- 15-methylerythromycin A. ES–LC/MS shows $[M+H]^-=627$.

Example 10

Synthesis of 2'-O-Acetyl-6-O-methyl-3-descladinosyl-3-oxo-10,11-anhydro-2-fluoro-15-methyl-erythromycin A A solution of 2'-O-acetyl-6-O-methyl-3-descladinosyl-3-oxo-10,11-anhydro-15-methyl-erythromycin A (198 mg, 0.316 mmol) in 2.1 mL of tetrahydrofuran under inert atmosphere was cooled to −78° C. and treated with 0.931 mL of 1.0 M potassium tert-butoxide in tetrahydrofuran. The mixture was stirred for 5 minutes, and a solution of N-fluorobenzenesulfonimide (230 mg) in 0.5 mL of tetrahydrofuran was added in three portions over 2 hours. After addition, the reaction was allowed to warm to ambient temperature and kept for an additional 5 hours. Aqueous $K_2CO_3$ was added, and the mixture was extracted with three 50-mL portions of $CH_2Cl_2$. The organic extracts were combined, dried over $MgSO_4$, filtered, and evaporated. Chromatography on silica gel (90:9:1 toluene/acetone/$Et_3N$) gave 95 mg of product as a white solid. ES–LC/MS: $[M+H]^+=645$. $^{13}C$-NMR ($CDCl_3$, 100 MHz): δ 206.95, 203.02 (br), 169.77, 166.08 (d, JCF=23 Hz), 141.71, 138.43, 101.63, 98.02 (d, JCF=203 Hz), 80.09 (br), 79.71, 78.27, 73.26, 71.52, 69.08, 63.33, 49.18, 40.61, 40.32, 41.79, 40.61, 40.32, 31.56, 31.47, 30.50, 24.37 (d, JCF=23 Hz), 23.19, 22.63, 20.95, 20.68, 19.80, 19.47, 14.10, 14.00, 13.55.

Example 11

Preparation A: Conversion of Formula (8) to Formula (11) where X=H, $R_{13}$=propyl and $R_a$=allyl.

Step 1: A solution of 2',4"-bis-O-trimethylsilyl-15-methylerythromycin A 9-[O-(1-isoprofoxycyclohexyl)] oxime (7.8 g, 7.44 mmol) in 30 mL of tetrahydrofuran was cooled on ice and treated with 30 mL of methylsulfoxide and 2.58 mL of freshly distilled allyl bromide under inert atmosphere. A mixture of methylsulfoxide (29.8 mL) and 1.0 M potassium tert-butoxide in tetrahydrofuran (29.8 mL) was added at a rate of 1.33 molar equivalents of base per hour. The reaction was monitored by thin-layer chromatography (silica gel, 10:1 toluene/acetone), and was judged complete after addition of 3.6 molar equivalents of base. The reaction was diluted with 700 mL of ethyl acetate and washed sequentially with saturated $NaHCO_3$, water, and brine. The organic phase was dried with $MgSO_4$, filtered, and evaporated to yield 8.08 g of crude 6-O-allyl-2',4"-bis-O-trimethylsilyl-15-methylerythromycin A 9-[O-(1-isopropoxycyclohexyl)] oxime. This was carried on without further purification.

Step 2: A solution of 6-O-allyl-2',4"-bis-O-trimethylsilyl-15-methylerythromycin A 9-[O-(1-isopropoxycyclohexyl)] oxime (8.08 g) in 42 mL of acetonitrile was treated with 21 mL of water and 24 mL of acetic acid, and stirred for 18 hours at ambient temperature. The mixture was concentrated after addition of 2-propanol, then repeatedly after addition of toluene to yield 7.7 g of crude product. Chromatography on silica gel (gradient from 2:1 to 1:1 hexanes/acetone +1% $Et_3N$) gave 3.75 g of 6-O-allyl-15-methylerythromycin A 9-oxime.

Step 3: A solution of 6-O-allyl-15-methylerythromycin A 9-oxime (3.75 g) and sodium hydrosulfite (85%, 5.37 g) in 66 mL of 1:1 ethanol/water was placed under inert atmosphere. Formic acid (0.845 mL) was added dropwise, and the mixture was stirred at 80° C. for 3.5 hours. After cooling to ambient temperature, the reaction was adjusted to pH 10 with 6 N NaOH and extracted three times with 150-mL portions of ethyl acetate. The organic extracts were combined and washed sequentially with saturated $NaHCO_3$, water, and brine. The organic phase was dried with $MgSO_4$, filtered, and evaporated to yield 3.42 g of 6-O-allyl-15-methylerythromycin A suitable for further conversion.

Preparation B: Conversion of Formula (8) to Formula (11) where X=H, $R_{13}$=methyl and $R_a$=allyl.

Step 1: A solution of 2',4"-bis-O-trimethylsilyl-14-norerythromycin A 9-[O-(1-isopropoxycyclohexyl)] oxime (202 mg) in tetrahydrofuran (0.4 mL), DMSO (0.4 mL), and ether (0.04 mL) was cooled to 10 ° C. and treated with 0.035 mL of freshly distilled allyl bromide under inert atmosphere. A mixture of methylsulfoxide (0.4mL) and 1.0 M potassium tert-butoxide in tetrahydrofuran (0.4 mL) was added at a rate 0.22 mL/hour. The reaction was monitored by thin-layer chromatography (silica gel, 5:1 toluene/acetone. The reaction was diluted with ethyl acetate and washed sequentially with saturated $NaHCO_3$, water, and brine. The organic phase was dried with $MgSO_4$, filtered, and evaporated to yield 222 mg of crude 6-O-allyl-2',4"-bis-O-trimethylsilyl-14-norerythromycin A 9-[O-(1-isopropoxycyclohexyl)] oxime. This was carried on without further purification.

Step 2: A solution of 6-O-allyl-2',4"-bis-0-trimethylsilyl-14-norerythromycin A 9-[O-(1-isopropoxycyclohexyl)] oxime (222 mg) in 4 mL of acetonitrile was treated with 2 mL of water and 2.4 mL of acetic acid, and stirred for 18 hours at ambient temperature. The mixture was concentrated after addition of 2-propanol, then repeatedly after addition of toluene to yield 220 mg of crude 6-O-allyl-14-norerythromycin A 9-oxime.

Step 3: A solution of 6-O-allyl-14-norerythromycin A 9-oxime (220 mg) and sodium hydrosulfite (85%, 322 mg) in 4 mL of 1:1 ethanol/water was placed under inert atmosphere. Formic acid (0.050 mL) was added dropwise, and the mixture was stirred at 80 ° C. for 15 hours. After cooling to ambient temperature, the reaction was adjusted to pH 10 with 6 N NaOH and extracted three times with 150-mL portions of ethyl acetate. The organic extracts were combined and washed sequentially with saturated $NaHCO_3$, water, and brine. The organic phase was dried with $MgSO_4$, filtered, and evaporated to yield 156 mg of 6-O-allyl-14-norerythromycin A suitable for further conversion.

Other embodiments: In a similar manner, compounds of formula (11) wherein Ra is allyl, are prepared from an intermediate where R13 is butyl, benzyl, vinyl, or 3-hydroxybutyl.

Scheme 5

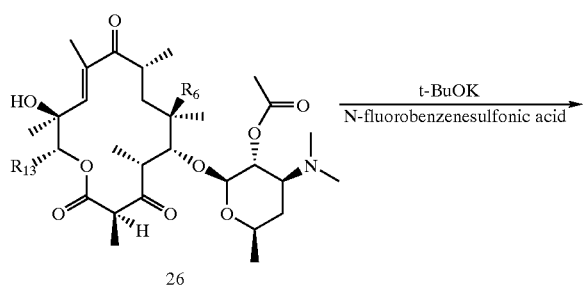

26

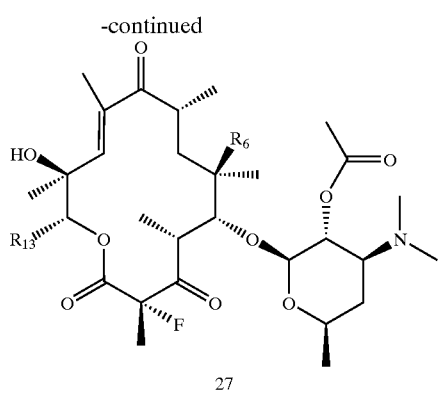

27

Example 12

Conversion of Formula (11) to Formula (14)
(Scheme 1)

Step 1. A mixture of the compound prepared in Example 11 (77 mg, crude), 0.073 ml of 12 N HCl and water (2 ml) was stirred at ambient temperature for 3 hours. The mixture was brought to pH 8 with 8 N KOH, and extracted with ethyl acetate. The organic extract was washed with brine, dried with $MgSO_4$, filtered, and evaporated. The residue was chromatographed on silica gel (3:1/hexanes:acetone, 1% triethylamine) to give pure product as a white solid (42 mg).

Step 2. To protect the 2' OH, a mixture the above compound (73 mg), potassium carbonate (20 mg), acetic anhydride (14µl) and acetone (1 ml) was stirred at ambient temperature for 18 hours. Ethyl acetate was added, washed with water and brine, dried over $MgSO_4$, filtered, and evaporated. The residue was chromatographed on silica gel (3:1 hexanes:acetone, 1% triethylamine) to yield the pure product (71 mg) as a white solid.

Step 3. A solution of the compound resulting from step 2 (99 mg) and 1-(3-dimethylaminopropyl)-3-ethylcarbodiidmide (EDC) hydrochloride (206 mg) in dichloromethane (2 ml) was treated with DMSO (0.21 ml) and cooled to 5° C. A solution of pyridinium trifluoroacetate (208 mg) in dichloromethane (2 ml) was added via a syringe pump in 4 hours. Ethyl acetate was then added, washed with saturated $NaHCO_3$, water, brine, and dried over $MgSO_4$, filtered, and evaporated. The residue was chromatographed on silica gel (3:1/hexanes:acetone, 1% triethylamine) to yield the pure compound of formula (14) (94 mg, $R_a$ is allyl, $R_2$ is acetate and $R_{13}$ is $CH_3$).

Step 4. To deprotect 2' OH, a solution of the compound resulting from step 3 (94 mg) in 5 mL methanol was stirred at room temperature for 24 hours. The solvent was removed in vacuo to give the desired compound of formula (14) ($R_a$ is allyl, $R_2$ is H, and $R_{13}$ is $CH_3$).

Other embodiments: In a similar manner, compounds of formula (14) wherein $R_a$ is allyl, $R_2$ is H, and $R_{13}$ is propyl, butyl, benzyl, vinyl, or 3-hydroxybutyl is prepared.

Example 13

Conversions at —OR$_a$

A. Allyl→Propyl

A solution of either of the compounds from steps 3 or 4 of Example 12 (0.2 mmol) in ethanol is flushed with nitrogen and 10% palladium on carbon (20 mg) added. The mixture is then flushed with hydrogen and the reaction mixture stirred overnight under positive hydrogen pressure. The reaction mixture is filtered and concentrated in vacuo to give a glass. Chromatography on silica gel (95:5:0.5 dichloromethane-methanol-ammonia) gives the propyl compounds as white solids.

B. Allyl→—CH$_2$CHO

Ozone is passed through a −78° C. solution in dichloromethane (100 mL) of either of the compounds from steps 3 or 4 of Example 12 (4.0 mmol) for 45 minutes. The reaction mixture is then flushed with nitrogen for 10 minutes. Dimethyl sulfide (1.46 mL, 20 mmol) is added at −78° C. and the reaction mixture stirred for 30 minutes at 0° C. The reaction mixture is concentrated in vacuo to give a white foam which is used without further purification by heating a solution of the compound in THF (40 mL, 4.0 mmol) and triphenylphosphine (2.62 g, 10.0 mmol) at 55° C. for 2.5 hours. The reaction mixture is concentrated in vacuo to give a white foam. Chromatography on silica gel (1:1 acetone-hexane, then 75:25:0.5 acetone-hexane-triethylamine) gives the desired compound as a white solid.

C. Allyl→—CH$_2$CH=NOH

To a solution in methanol (5 mL) of the compound prepared in B wherein R$_a$ is —CH$_2$CHO, (0.08 mmol) is added triethylamine (31 L, 0.225 mmol) and hydroxylamine hydrochloride (7.7 mg, 0.112 mmol) and the reaction mixture stirred for 6 hours at ambient temperature. The reaction mixture is taken up in ethyl acetate and washed with aqueous 5% sodium bicarbonate and brine, dried over sodium sulfate, and concentrated in vacuo to give a clear glass. Chromatography on silica gel (95:5:0.5 dichloromethane-methanol-ammonia) gives the compound as a white solid.

D. —CH$_2$CH=NOH→—CH$_2$CN

To a solution under nitrogen of the compound prepared in C (0.267 mmol) in THF (5 mL) is added diisopropylcarbodiimide (83 μL, 0.534 mmol) and CuCl (2.7 mg, 0.027 mmol) and the reaction mixture is stirred overnight at ambient temperature. The reaction mixture is taken up in ethyl acetate and washed with aqueous 5% sodium bicarbonate and brine, dried over sodium sulfate, and concentrated in vacuo to give a clear glass. Chromatography on silica gel (95:5:0.5 dichloromethane-methanol-ammonia) gives the desired compound as a white solid.

E. —CH$_2$CHO→—CH$_2$CH$_2$NH$_2$

To a solution in methanol (10 mL) of the compound prepared in B (0.276 mmol) is added ammonium acetate (212 mg, 2.76 mmol) and the mixture is cooled to 0° C. Sodium cyanoborohydride (34 mg, 0.553 mmol) is added and the reaction mixture stirred for 30 hours at 0° C. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (90:10:0.5 dichloromethane-methanol-ammonia) gives the desired compound as a white solid.

F. —CH$_2$CHO→—CH$_2$CH$_2$NHCH$_2$-Phenyl

To a 0° C. solution in methanol (10 mL) of the compound prepared in B (0.200 mmol) is added acetic acid (114 μL, 2.00 mmol) and benzylamine (218 μL, 2.00 mmol) and the mixture is stirred for 10 minutes. Sodium cyanoborohydride (24.8 mg, 0.400 mmol) is added and the reaction mixture stirred for 16 hours. Additional sodium cyanoborohydride (24.8 mg, 0.400 mmol) is then added and stirring continued for 5 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (95:5:0.5 dichloromethane-methanol-ammonia) followed by a second chromatography (50:50:0.5 acetone-hexanes-triethylamine) gives the desired compound as a white foam.

G. —CH$_2$CHO→—CH$_2$CH$_2$NHCH$_2$CH$_2$-Phenyl

To a 0° C. solution in methanol (10 mL) of the compound prepared in B (0.200 mmol) is added acetic acid (114 μL, 2.00 mmol) and phenethylamine (218 L, 2.00 mmol) and the mixture stirred for 10 minutes. Sodium cyanoborohydride (24.8 mg, 0.400 mmol) is added and the reaction mixture stirred for 16 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (90:10:0.5 dichloromethane-methanol-ammonia) gives the desired compound.

H. —CH$_2$CHO→—CH$_2$CH$_2$NHCH(CO$_2$CH$_3$)CH$_2$-Phenyl

To a 0° C. solution in methanol (10 mL) of the compound prepared in B (0.200 mmol) is added L-phenylalanine methyl ester hydrochloride (129 mg, 0.600 mmol) and the mixture stirred for 10 minutes. Sodium cyanoborohydride 924.8 mg, 0.400 mmol) is added and the reaction mixture stirred for 22 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (95:5:0.5 dichloromethane-methanol-ammonia) gives the desired compound.

I. —CH$_2$CHO→—CH$_2$CH$_2$NHCH$_2$-(4-pyridyl)

The desired compound is prepared according to the method in G, except substituting 4-aminomethylpyridine for phenethylamine.

J. —CH$_2$CH$_2$NH$_2$→—CH$_2$CH$_2$NHCH$_2$-(4-quinolyl)

To a solution of the compound prepared in E (0.15 mmol) in methanol (2 mL) is added 4-quinolinecarboxaldehyde (23 mg, 0.15 mmol), acetic acid (8.6 L, 0.15 mmol), and sodium cyanoborohydride (9.4 mg, 0.15 mmol) and the reaction mixture is stirred for 15 hours. The reaction mixture is taken up in ethyl acetate and washed with aqueous 5% sodium carbonate, aqueous 2% tris(hydroxymethyl)aminomethane, and brine, dried over sodium sulfate, filtered, and concentrated in vacuo. Chromatography on silica gel (95:10:0.5 dichloromethane-methanol-ammonia) gives the desired compound.

K. Allyl→—CH$_2$CH=CH-Phenyl

To a solution under nitrogen of the 2' protected compound prepared in Example 12 (1.00 mmol), palladium(II)acetate (22 mg, 0.100 mmol), and triphenylphosphine (52 mg, 0.200 mmol) in acetonitrile (5 mL) was added iodobenzene (220 μL, 2.00 mmol) and triethylamine (280 μL, 2.00 mmol) and the mixture is cooled to −78° C, degassed, and sealed. The reaction mixture is then warmed to 60° C. for 0.5 hours and stirred at 80° C. for 12 hours, taken up in ethyl acetate and washed twice with aqueous 5% sodium bicarbonate, once with aqueous 2% tris(hydroxymethyl)aminomethane, and once with brine, dried over sodium sulfate, filtered, and concentrated in vacuo. Chromatography on silica gel (95:5:0.5 dichloromethane-methanol-ammonia) gives the desired compound.

Deprotection is accomplished by heating in methanol.

Other embodiments of formula (14) where $R_2$ is H and $R_{13}$ is propyl, butyl, benzyl, vinyl, or 3-hydroxybutyl are those wherein $R_a$ is:

| | |
|---|---|
| —CH$_2$CH$_2$CH$_2$-phenyl; | —CH$_2$CH=CH-(4-methoxyphenyl); |
| —CH$_2$CH=CH-(4-chlorophenyl); | —CH$_2$CH=CH-(3-quinolyl); |
| —CH$_2$CH$_2$CH$_2$OH; | —CH$_2$C(O)OH; |
| —CH$_2$CH$_2$NHCH$_3$; | —CH$_2$CH$_2$NHCH$_2$OH; |
| —CH$_2$CH$_2$N(CH$_3$)$_2$; | —CH$_2$CH$_2$(1-morpholinyl); |
| —CH$_2$C(O)NH$_2$; | —CH$_2$NHC(O)NH$_2$; |
| —CH$_2$NHC(O)CH$_3$; | —CH$_2$F; |
| —CH$_2$CH$_2$OCH$_3$; | —CH$_2$CH$_3$; |
| —CH$_2$CH=CH(CH$_3$)$_2$; | —CH$_2$CH$_2$CH(CH$_3$)CH$_3$; |
| —CH$_2$CH$_2$OCH$_2$CH$_2$OCH$_3$; | —CH$_2$SCH$_3$; |
| -cyclopropyl; | —CH$_2$OCH$_3$; |
| —CH$_2$CH$_2$F; | —CH$_2$-cyclopropyl; |
| —CH$_2$CH$_2$CHO; | —C(O)CH$_2$CH$_2$CH$_3$; |
| —CH$_2$-(4-nitrophenyl); | —CH$_2$-(4-chlorophenyl); |
| —CH$_2$-(4-methoxyphenyl); | —CH$_2$-(4-cyanophenyl); |
| —CH$_2$CH=CHC(O)OCH$_3$; | —CH$_2$CH=C HC(O)OCH$_2$CH$_3$; |
| —CH$_2$CH=CHCH$_3$; | —CH$_2$CH=CHCH$_2$CH$_3$; |
| —CH$_2$CH=CHCH$_2$CH$_2$CH$_3$; | —CH$_2$CHSO$_2$-phenyl; |
| —CH$_2$CCSi(CH$_3$)$_3$ | —CH$_2$CCCH$_2$CH$_2$CH$_2$CH$_2$CH$_3$; |
| —CH$_2$C CCH$_3$; | —CH$_2$-(2-pyridyl); |
| —CH$_2$-(3-pyridyl); | —CH$_2$-(4-pyridyl); |
| —CH$_2$-(4-quinolyl); | —CH$_2$NO$_2$; |
| —CH$_2$C(O)OCH$_3$; | —CH$_2$C(O)-phenyl; |
| —CH$_2$C(O)CH$_2$CH$_3$; | —CH$_2$Cl; |
| —CH$_2$S(O)$_2$-phenyl; | —CH$_2$CH=CHBr; |
| —CH$_2$CH=CH-(4-quinolyl); | —CH$_2$CH$_2$CH$_2$-(4-quinolyl); |
| —CH$_2$CH=CH-(5-quinolyl); | —CH$_2$CH$_2$CH$_2$-(5-quinolyl); |
| —CH$_2$CH=CH-(4-benzoxazolyl); | —CH$_2$CH=CH-(7-benzimidazolyl). |
| or | |

Example 14

Preparation of Compound of Formula (I) where R= H, $R_2$=H, X=H, $R_6$=—$OR_a$, $R_a$ is —CH$_2$CH=CH$_2$ (Scheme 3)

Step 1: Preparation to Form 10,11-Anhydro Form of Intermediate Compound (20):, $R_a$ is —CH$_2$CH=CH$_2$, $R_2$ is Benzoyl.

A. 6-O-Allyl-3-descladinosyl-15-methyl-erythromycin A

A mixture of 6-O-allyl-15-methylerythromycin A (6.58 g) and 125 mL of 0.5 N HCl was stirred at ambient temperature for 20 hours. The pH was adjusted to 10 by addition of 6 N NaOH, and the mixture was extracted three times with 225-mL portions of ethyl acetate. The organic extracts were combined, washed sequentially with saturated NaHCO$_3$, water, and brine, then dried over MgSO$_4$, filtered, and evaporated. The crude product was chromatographed on silica gel (3:2 toluene/acetone +1% Et$_3$N) to yield 3.04 g of pure 6-O-allyl-3-descladinosyl-15-methylerythromycin A. ES–LC/MS shows [M+H]$^-$=617.

B. 2'-O-Benzoyl-6-O-allyl-3-descladinosyl-15-methyl-erythromycin A

6-O-Allyl-3-descladinosyl-15-methylerythromycin A (2.43 g, 3.86 mmol, 1.00 eq) and benzoic anhydride (1.78 g, 7.72 mmol, 2.00 eq) were placed in a round-bottomed flask and flushed with N$_2$. Ethyl acetate (17.5 mL) was added. The solution was stirred for 3.5 h and then diluted with 400 mL of EtOAc and washed twice with 150 mL of saturated aqueous NaHCO$_3$ and once each with 150 mL of water and brine. The organic phase was dried over MgSO$_4$, filtered, and concentrated. Purification by flash chromatography over silica gel (3:1 hexanes:acetone +1% Et$_3$N) gave 1.94 g (68.1%) of the desired product as a white solid. ES–LC/MS shows [M+H]$^-$=721. $^{13}$C NMR (100.6 MHz, CDCl$_3$) δ 219.4, 174.3, 165.4, 135.3, 132.6, 130.8, 129.7, 128.2, 117.2, 99.7, 80.7, 79.0, 77.9, 77.7, 75.1, 74.3, 72.3, 69.0, 64.7, 63.3, 45.6, 43.9, 40.7, 37.9, 37.7, 35.7, 32.1, 30.8, 21.1, 20.2, 19.3, 18.1, 16.3, 15.1, 14.0, 12.4, 7.7.

C. 2'-O-Benzoyl-6-O-allyl-3-descladinosyl-3-oxo-15-methyl-erythromycin A

N-Chlorosuccinimide (0.510 g, 3.82 mmol, 1.50 eq) was dissolved in 13 mL of anhydrous CH$_2$Cl$_2$ and cooled to −10° C. under N$_2$. Methyl sulfide (0.328 mL, 4.46 mmol, 1.75 eq) was added, and the reaction was stirred for 15 min. A solution of 2'-O-benzoyl-6-O-allyl-3-descladinosyl-15-methylerythromycin A (1.87 g, 2.55 mmol, 1.00 eq) in 13 mL of anhydrous CH$_2$Cl$_2$ was added dropwise. After 30 min, freshly distilled Et$_3$N (0.355 mL, 2.55 mmol, 1.00 eq) was added; and the reaction was brought up to 0° C. over 30 min. The reaction mixture was diluted with 400 mL EtOAc and washed successively with 100 mL each of saturated aqueous NaHCO$_3$, water, and brine. The organic layer was dried over MgSO$_4$, filtered, concentrated, and purified by flash chromatography (9:1 hexanes:acetone +1% Et$_3$N) to give 0.931 g (49.9%) of the desired product as a white solid. ES–LC/MS shows [M+H]$^-$=719. $^{13}$C NMR (100.6 MHz, CDCl$_3$) δ 219.1, 206.1, 169.5, 165.3, 135.3, 132.7, 129.0, 129.7, 128.3, 117.4, 100.7, 78.5, 76.6, 75.3, 74.2, 72.1, 69.2, 69.0, 64.5, 63.7, 50.6, 45.3, 44.8, 40.7, 38.3, 37.8, 31.7, 31.0, 21.1, 20.2, 19.5, 18.1, 16.5, 14.5, 14.0, 12.6, 12.2.

D. 2'-O-Benzoyl-6-O-allyl-3-descladinosyl-3-oxo-11-O-methanesulfonyl-15-methyl-erythromycin A 2'-O-Benzoyl-6-O-Allyl-3-descladinosyl-3-oxo-15-methylerythromycin A (904 mg, 1.24 mmol, 1.00 eq) was dissolved in freshly distilled pyridine (4 mL) and cooled to 0° C. Methanesulfonyl chloride (0.478 mL, 6.17 mmol, 5.00 eq) was added dropwise. The reaction was allowed to come to ambient temperature and stirred overnight. The mixture was diluted with 350 mL of EtOAc and quenched with 100 mL of saturated aqueous NaHCO$_3$. The layers were separated, and the organic phase was washed successively with 100 mL each of water and brine. The organic phase was dried over MgSO$_4$, filtered, and concentrated. Flash chromatography over silica gel (4:1 hexanes:acetone +1% Et$_3$N) gave 741 mg (74.1%) of the desired compound as a white solid. $^{13}$C NMR (100.6 MHz, CDCl$_3$) δ 203.0, 168.9, 165.0, 137.6, 133.1, 130.3, 129.8, 128.5, 114.4, 108.8, 102.2, 91.1, 84.4, 81.6, 78.8, 72.2, 69.2, 64.3, 63.9, 52.1, 46.6, 45.8, 40.7, 38.8, 38.2, 35.9, 31.8, 30.9, 29.7, 24.8, 21.0, 19.6, 18.2, 15.5, 15.4, 13.8, 13.5.

E. 2'-O-Benzoyl-6-O-allyl-3-descladinosyl-3-oxo-10,11-anhydro-15-methyl-erythromycin A 2'-O-Benzoyl-6-O-allyl-3-descladinosyl-3-oxo-11-methanesulfonyl-15-methyl-erythromycin A (705 mg, 0.870 mmol, 1.00 eq) was dissolved in acetone (3 mL), and 1,8-diazabicyclo[5.4.0]undec-7-ene (0.651 mL, 4.35 mmol, 5.00 eq) was added dropwise. The reaction was stirred at ambient temperature for 6 h and then concentrated. Flash chromatography over silica gel (4:1 hexanes:acetone +1% Et$_3$N) gave 486 mg (78.0%) of the desired compound as a white solid. $^{13}$C NMR (100.6 MHz, CDCl$_3$) δ 210.1, 208.4, 170.2, 165.2, 141.0, 140.2,136.3, 132.7,130.4, 129.8, 128.2, 115.5, 100.6, 81.0, 78.7, 77.2, 73.8, 72.0, 69.1, 64.6, 63.3, 51.0, 47.4, 40.8, 39.4, 36.2, 31.9, 31.3, 23.6, 21.2, 21.1, 21.0, 19.4, 14.1, 13.9, 13.7, 13.1.

Step 2: Derivatization of Position 12 Hydroxyl of Compound (18) From Illustrative Scheme 3: $R_a$ is —CH$_2$CH=CH$_2$, $R_2$ is Benzoyl.

2'-O-Benzoyl-6-O-allyl-10,11-anhydro-3-descladinosyl-3-oxo-15-methyl-erythromycin A (227 mg, 0.317 mmol, 1.00 eq) was dissolved in 1.3 mL of freshly distilled THF and cooled to −15° C. under N$_2$. Sodium hydride (25 mg of a 60% dispersion in mineral oil, 0.634 mmol, 2.00 eq) was added, and the reaction was stirred for 15 min. A solution of 1,1-carbonyldiimidazole (140 mg, 0.866 mmol, 3.00 eq) in 1.3 mL of freshly distilled THF was added dropwise. After stirring for 30 min, the reaction was allowed to warm to ambient temperature over 1.5 h. The mixture was diluted with 100 mL of EtOAc and washed successively with 30 mL each of saturated aqueous NaHCO$_3$, water, and brine. The organic phase was dried over MgSO$_4$, filtered, and concentrated to give 275 mg of crude product (100%) which was dissolved in 2 mL of ACN and 0.2 mL of anhydrous THF. Saturated aqueous ammonium hydroxide (2 mL) was added. The reaction was sealed and stirred for 2 d. Volatiles were removed under reduced pressure, and the residue was re-dissolved in 100 mL of EtOAc. The solution was washed successively with 30 mL each of saturated aqueous NaHCO$_3$, water, and brine. The organic phase was dried over MgSO$_4$, filtered, and concentrated. Flash chromatography of the crude product (4:1 hexanes:acetone +1% Et$_3$N) yielded 184 mg (76.5%) of the desired product.

Example 15

Preparation A: Formula (I): X=H, R$_a$ is —CH$_2$—CH=CH-(3-Quinolyl)

Step 1: 2'-O-Benzoyl-6-O-allyl-11-amino-3-descladinosyl-11-deoxy-3-oxo-15-methylerythromycin A 11,12-cyclic carbamate (40 mg, 0.0528 mmol, 1.0 eq), tris(dibenzylideneacetone) dipalladium(0)-chloroform adduct (14 mg, 0.014 mmol, 0.5 eq), tri-o-tolylphosphine (17 mg, 0.055 mmol, 1.0 eq), and 3-bromoquinoline (72 μl, 0.53 mmol, 10 eq) were placed in a round-bottom flask which was flushed with N$_2$. Degassed acetonitrile (I mL) and freshly distilled Et$_3$N (0.015 ml, 0.11 mmol, 2.0 eq) were added. The reaction was refluxed for 63 h. The mixture was returned to ambient temperature and diluted with 40 mL of EtOAc. The solution was washed successively with 10 mL each of saturated aqueous NaHCO$_3$, water, and brine. The organic phase was dried over MgSO$_4$, filtered, and concentrated. Flash chromatography of the crude product (gradient from 5:1 to 2:1 hexanes:acetone +1% Et$_3$N) yielded 34 mg of the desired product.

Step 2: The above product (34 mg) was dissolved in 1 mL of methanol, sealed, and refluxed at 80° C. for 16 h. Volatiles were removed under reduced pressure. Flash chromatography (1:1 hexanes:acetone+1% Et$_3$N) gave the desired product as a light yellow solid (25 mg, 61% over two steps). ES–LC/MS: [M+H]$^+$=780.5. $^{13}$C-NMR (CDCl$_3$, 100 MHz): δ 217.44, 205.37, 169.48, 157.69, 149.71, 147.61, 132.51, 129.96, 129.56, 129.15, 129.05, 128.49, 128.05, 126.70, 102.90, 83.42, 78.71, 76.42, 75.91, 70.22, 69.53, 65.83, 64.31, 58.12, 50.81, 46.29, 46.12, 45.05, 40.18 (2 C), 39.05, 37.31, 31.64, 28.19, 21.15, 20.18, 19.43, 18.05, 14.38, 14.11, 13.76, 13.63 (2 C).

Preparation B: formula (I): X=H, R$_a$ is —CH$_2$—CH=CH-(3-(6-Fluoroquinolyl)

This was prepared according to the method of Preparation A using 3-bromo-6-fluoroquinoline in place of 3-bromoquinoline. ES–LC/MS: [M+H]$^+$=798.5. $^{13}$C-NMR (CDCl$_3$,100 MHz): δ 217.49,205.36, 169.54, 160.6 (J$_{CF}$=248 Hz), 157.68, 149.05, 144.69, 131.84, 131.64 (J$_{CF}$=9 Hz), 130.28, 129.63, 129.31, 128.7 (J$_{CF}$=10 Hz), 119.20 (J$_{CF}$=27 Hz), 110.87 (J$_{CF}$=22 Hz), 102.94, 83.42, 78.77, 76.44, 75.91, 70.22, 69.55, 65.84, 64.24, 58.09, 50.83, 46.36, 46.06, 45.05, 40.18 (2 C) 39.04, 37.32, 31.63, 28.19, 21.16, 20.19, 19.46, 18.04, 14.37, 14.18, 13.76, 13.62 (2 C).

Preparation C: Formula (I): X=H, R$_a$ is —CH$_2$—CH=CH-(3-(6-Chloroquinolyl)

This is prepared according to the method of Preparation A using 3-bromo-6-chloroquinoline in place of 3-bromoquinoline. ES–LC/MS: [M+H]$^+$=814.5. $^{13}$C-NMR (CDCl$_3$,100 MHz): δ 217.48, 205.35, 169.55, 157.67, 149.90, 145.92, 132.42, 131.49, 130.80, 130.44, 129.92, 129.49, 129.46, 128.71, 126.57, 102.94, 83.41, 78.78, 76.45, 75.91, 70.22, 69.54, 65.83, 64.23, 58.07, 50.83, 46.39, 45.99, 45.04, 40.17 (2 C), 39.03, 37.32, 31.62, 31.53, 28.18, 21.16, 20.17, 19.49, 18.04, 14.36, 14.21, 13.76, 13.61 (2 C).

Preparation D: Formula (I): X=H, R$_a$ is —CH$_2$—CH=CH-(4-Isoquinolyl)

This was prepared according to the method of Preparation A using 4-bromoisoquinoline in place of 3-bromoquinoline. ES–LC/MS: [M+H]$^+$=781. $^{13}$C-NMR (CDCl$_3$,100 MHz): δ 217.19,205.43, 169.75, 157.39, 152.07, 140.74, 133.61, 130.65, 130.44, 128.07, 127.72, 127.05, 126.89, 122.77, 102.85, 83.28, 78.74, 75.72, 70.22, 69.51, 65.88, 64.45, 58.10, 50.91, 46.07, 45.09, 40.18 (2 C) 38.99, 37.34, 31.48, 29.66, 28.28, 21.18, 20.39, 19.33, 14.53, 14.01, 13.86, 13.66, 13.62.

Preparation E: Formula (I): X=H, R$_a$ is —CH$_2$—CH=CH-(3-Pyridyl)

This was prepared according to the method of Preparation A using 3-bromopyridine in place of 3-bromoquinoline. LC/MS: [M+H]$^+$=731. $^{13}$C-NMR (CDCl$_3$, 100 MHz): δ 217.39, 205.27, 169.50, 157.61, 148.81, 148.68, 132.63, 132.16, 129.65, 128.18, 123.46, 102.91, 83.36, 78.63, 76.35, 75.79, 70.20, 69.52, 65.83, 64.17, 58.06, 50.78, 46.28, 45.03, 40.16 (2 C), 38.96, 37.29, 31.64, 31.52, 28.19, 22.58, 21.14, 20.21, 19.42, 18.04, 1.35, 14.12, 14.05, 13.79, 13.61 (2 C).

Preparation F: Formula (I): X=H, R$_a$ is —CH$_2$—CH=CH-(3-(6-Methylquinolyl)

This was prepared according to the method of Preparation A using 3-bromo-6-methylquinoline in place of 3-bromoquinoline. ES–LC/MS: [M+H]$^+$=795. $^{13}$C-NMR (CDCl$_3$, 100 MHz): δ 217.37, 205.35, 169.47, 157.65, 148.82, 146.23, 136.45, 131.87, 131.37, 130.09, 129.51, 128.78, 128.22, 128.06, 126.86, 102.87, 83.40, 78.68, 75.91, 70.20, 69.47, 65.83, 64.33, 58.11, 50.81, 46.28, 45.04, 40.15 (2 C), 39.05, 37.31, 31.64, 28.24, 21.52, 21.14, 20.18, 19.45, 18.05, 14.38, 14.11, 13.77, 13.63 (2 C).

Preparation G: Formula (I): X=H, R$_a$ is —CH$_2$—CH=CH-(3-(6-Aminoquinolyl)

This was prepared according to the method of Preparation A using 3-bromo-6-aminoquinoline in place of 3-bromoquinoline. ES–LC/MS: [M+H]$^+$=796.

Preparation H: Formula (I): X=H, R$_a$ is —CH$_2$—CH=CH-(3-(5-Isoxazol-3-yl)thienyl)

This is prepared according to the method of Preparation A, using 5-(isoxazol-3-yl)-2-bromothiophene in place of 3-bromoquinoline.

Preparation I: Formula (I): X=H, R$_a$ is —CH$_2$—CH=CH-(6-Quinolyl)

This is prepared according to the method of Preparation A, using 6-bromoquinoline in place of 3-bromoquinoline.

Preparation J: Formula (I): X=H, R$_a$ is —CH$_2$—CH=CH-(3-Quinolyl-6-yl)

This is prepared according to the method of Preparation A using 6-bromoquinoxaline in place of 3-bromoquinoline.

Preparation K: Formula (I): X=H, R$_a$ is —CH$_2$—CH=CH-(5-(N-(2Pyridyl)-2-furamidyl)

This is prepared according to the method of Preparation A, using N-(2-pyridyl) 5-bromo-2-furamide in place of 3-bromoquinoline.

Preparation AA: Formula (I): X=F, R$_a$ is —CH$_2$—CH=CH-(3-Quinolyl)

This was prepared according to the method of Preparation A using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate. LC/MS: [M+H]$^+$=798.6. $^{19}$F-NMR (CDCl$_3$,376 MHz): 5–163.93. $^{13}$C-NMR (CDCl$_3$,100 MHz): δ 217.97, 204.28 (J$_{CF}$=27 Hz), 165.62 (J$_{CF}$=23 Hz), 157.18, 149.71, 147.70, 132.65, 130.25, 129.53, 129.22, 129.12, 129.06, 128.15, 128.08, 126.78, 104.10, 98.02 (J$_{CF}$=206 Hz), 83.40, 79.59, 79.37, 77.57, 70.41, 69.74, 65.85, 64.36, 58.11, 44.23, 40.83 (J$_{CF}$=1.5 Hz), 40.25 (2 C), 39.04, 37.45, 31.37, 28.16, 25.30

($J_{CF}$=22 Hz), 21.19, 20.86, 19.54, 17.67, 15.46 ($J_{CF}$=1.7 Hz), 13.82, 13.80, 13.29.

Preparation BB: Formula (I): X=F, $R_a$ is —CH$_2$—CH=CH-(3-(6-Fluoroquinolyl)

This is prepared according to the method of Preparation B using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation CC: Formula (I): X=F, $R_a$ is —CH$_2$—CH=CH-(3-(6-Chloroquinolyl)

This is prepared according to the method of Preparation C using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-1 1-amino-3-descladinosyl-11 -deoxy-3-oxo-15-methylerythromycin A 11,12-cyclic carbamate.

Preparation DD: Formula (I): X=F, $R_a$ is —CH$_2$—CH=CH-(4-Isoquinolyl)

This is prepared according to the method of Preparation D using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-1 5-methylerythromycin A 11,12-cyclic carbamate.

Preparation EE: Formula (I): X=F, $R_a$ is —CH$_2$—CH=CH-(3 Pyridyl)

This is prepared according to the method of Preparation E using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation FF: Formula (I): X=F, $R_a$ is —CH$_2$—CH=CH-(3-(6-Methylquinolyl)

This is prepared according to the method of Preparation F using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation GG: Formula (I): X=F, $R_a$ is —CH$_2$—CH=CH-(3-(6-Aminoquinolyl)

This is prepared according to the method of Preparation G using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation HH: Formula (I): X=F, $R_a$ is —CH$_2$—CH=CH-(3-(5-Isoxazol-3-yl)thienyl)

This is prepared according to the method of Preparation H using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation II: Formula (I): X=F, $R_a$ is —CH$_2$—CH=CH-(6-Quinolyl)

This is prepared according to the method of Preparation I using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation JJ: Formula (I): X=F, $R_a$ is —CH$_2$—CH=CH-(3-Quinolyl-6-yl)

This is prepared according to the method of Preparation J using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-I 1-amino-3-descladinosyl-11-deoxy-3-oxo-15-methylerythromycin A 11,12-cyclic carbamate.

Preparation KK: Formula (I): X F, $R_a$ is —CH$_2$—CH=CH-(5-(N-(2-Pyridyl)-2-furamidyl)

This is prepared according to the method of Preparation K using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Example 16

Preparation of Compound of Formula (I): X=H, $R_a$ is —O-Propargyl (Scheme 3)

Step 1: A solution of 2',4"-bis-O-trimethylsilyl-15-methylerythromycin A 9-[O-(1-isopropoxycyclohexyl)] oxime (100 mg) in 0.1 mL of tetrahydrofuran, 0.1 mL of ether, and 0.1 mL of DMSO was cooled to 10° C. and treated with 0.028 mL of 3-bromo-1-(trimethylsilyl)-1-propyne under inert atmosphere. A mixture of methylsulfoxide (0.19 mL) and 1.0 M potassium tert-butoxide in tetrahydrofuran (0.38 mL) was added at a rate of 2.0 molar equivalents of base per hour. Additional equivalents (0.014 mL) of the TMS-propargyl bromide were added after 0.5 and 1 hours. The reaction was monitored by thin-layer chromatography (silica gel, 10:1 toluene/acetone), and was judged complete after addition of 2.3 molar equivalents of base. The reaction was diluted with 100 mL of ethyl acetate amd 30 mL of saturated NaHCO$_3$, and washed sequentially with saturated NaHCO$_3$, water, and brine. The organic phase was dried with MgSO$_4$, filtered, and evaporated. The crude product was chromatographed on silica gel (40:1 hexanes/acetone +1% Et$_3$N) to yield partially purified 6-O-(3-trimethylsilyl) propargyl-2',4"-bis-O-trimethylsilyl-15-methylerythromycin A 9-[O-(1-isopropoxycyclohexyl)] oxime.

Step 2: A solution of the impure 6-O-(3-trimethylsilyl) propargyl-2',4"-bis-O-trimethylsilyl-15-methylerythromycin A 9-[O-(1-isopropoxycyclohexyl)] oxime from above (0.88 g) in 4.4 mL of acetonitrile is treated with 2.2 mL of water and 2.5 mL of acetic acid, and stirred for 24 hours at ambient temperature. The mixture is concentrated after addition of 2-propanol, then repeatedly after addition of toluene. This material is stirred with potassium carbonate and methanol (6 mL) for 2.5 hours. The mixture is diluted with ethyl acetate (200 mL), and washed sequentially with saturated NaHCO$_3$, water, and brine. The organic phase is dried with MgSO$_4$, filtered, and evaporated to yield the product.

Step 3: A solution of the product from (iii) and sodium hydrosulfite (0.59 g) in 7 mL of 1:1 ethanol/water is placed under inert atmosphere. Formic acid (0.096 mL) is added dropwise, and the mixture is stirred at 80° C. for 5 hours. After cooling to ambient temperature, the reaction is adjusted to pH 10 with 6 N NaOH and extracted three times with 150-mL portions of ethyl acetate. The organic extracts are combined and washed sequentially with saturated NaHCO$_3$, water, and brine. The organic phase is dried with MgSO$_4$, filtered, and evaporated to yield 6-O-propargyl-15-methylerythromycin A suitable for further conversion. Pure material can be prepared by chromatography on silica gel.

Step 4: A mixture of 6-O-propargyl-15-methylerythromycin A (0.40 g) and 6 mL of 0.6 N HCl is stirred at ambient temperature for 17 hours. The pH is adjusted to 9 by addition of 6 N NaOH, and 150 mL of ethyl acetate is added. The organic extracts are washed sequentially with saturated NaHCO$_3$, water, and brine, then dried over MgSO$_4$, filtered, and evaporated to provide further product. The crude product is chromatographed on silica gel to give pure 6-O-propargyl-3-descladinosyl-15-methylerythromycin A.

Step 5: A solution of 6-O-propargyl-3-descladinosyl-15-methylerythromycin A (0.16 g) and benzoic anhydride (0.12 g) in 1.3 mL of ethyl acetate is stirred for 17 h, then washed sequentially with saturated NaHCO$_3$, water, and brine. The solution is dried over MgSO$_4$, filtered, and evaporated. The crude product is chromatographed on silica gel to yield 2'-O-benzoyl-6-O-propargyl-3-descladinosyl-15-methylerythromycin A.

Step 6: N-Chlorosuccinimide (0.510 g, 3.82 mmol, 1.50 eq) is dissolved in 13 mL of anhydrous CH$_2$Cl$_2$ and cooled to −10° C. under N$_2$. Methyl sulfide (0.328 mL, 4.46 mmol, 1.75 eq) is added, and the reaction is stirred for 15 min. A solution of 2'-O-benzoyl-6-O-propargyl-3-descladinosyl-15-methylerythromycin A (1.87 g, 2.55 mmol, 1.00 eq) in 13 mL of anhydrous CH$_2$Cl$_2$ is added dropwise. After 30 min, freshly distilled Et$_3$N (0.355 mL, 2.55 mmol, 1.00 eq) is added, and the reaction is brought up to 0° C. over 30 min. The reaction mixture is diluted with 400 mL EtOAc and washed successively with 100 mL each of saturated aqueous NaHCO$_3$, water, and brine. The organic layer is dried over MgSO$_4$, filtered, concentrated, and purified by chromatography.

Step 7: 2'-O-Benzoyl-6-O-propargyl-3-descladinosyl-3-oxo-15-methylerythromycin A (904 mg) is dissolved in freshly distilled pyridine (4 mL) and cooled to 0° C. Methanesulfonyl chloride (0.478 mL, 6.17 mmol, 5.00 eq) is added dropwise. The reaction is allowed to come to ambient temperature and stirred overnight. The mixture is diluted with 350 mL of EtOAc and quenched with 100 mL of saturated aqueous NaHCO$_3$. The layers are separated, and the organic phase is washed successively with 100 mL each of water and brine. The organic phase is dried over MgSO$_4$, filtered, and concentrated. Flash chromatography over silica gel yields the product.

Step 8: 2'-O-Benzoyl-6-O-propargyl-3-descladinosyl-3-oxo-11-methanesulfonyl-15-methyl-erythromycin A (705 mg) is dissolved in acetone (3 mL), and 1,8-diazabicyclo[5.4.0]-undec-7-ene (0.651 mL, 4.35 mmol, 5.00 eq) is added dropwise. The reaction is stirred at ambient temperature for 6 h and then concentrated. Flash chromatography over silica gel yields the product.

Step 9: 2'-O-Benzoyl-6-O-propargyl-10,11-anhydro-3-descladinosyl-3-oxo-15-methylerythromycin A (227 mg) is dissolved in 1.3 mL of freshly distilled THF and cooled to −15° C. under N$_2$. Sodium hydride (25 mg of a 60% dispersion in mineral oil, 0.634 mmol, 2.00 eq) is added, and the reaction was stirred for 15 min. A solution of 1,1-carbonyldiimidazole (140 mg) in 1.3 mL of freshly distilled THF is added dropwise. After stirring for 30 min, the reaction is allowed to warm to ambient temperature over 1.5 h. The mixture is diluted with 100 mL of EtOAc and washed successively with 30 mL each of saturated aqueous NaHCO$_3$, water, and brine. The organic phase is dried over MgSO$_4$, filtered, and concentrated, then the residue is dissolved in 2 mL of ACN and 0.2 mL of anhydrous THF. Saturated aqueous ammonium hydroxide (2 mL) is added. The reaction is sealed and stirred for 2 days. Volatiles are removed under reduced pressure, and the residue is redissolved in 100 mL of EtOAc. The solution is washed successively with 30 mL each of saturated aqueous NaHCO$_3$, water, and brine. The organic phase is dried over MgSO$_4$, filtered, and concentrated. Flash chromatography yields the cyclic carbamate product.

Example 17

Preparation of Compound of Formula (I): X=H, R$_6$=O-3-(Quinolin-3-yl)prop-2-ynyl (Scheme 3)

Preparation A: Formula (I): X=H, R$_a$ is —CH$_2$—CC-(3-Quinolyl)

Step 1: 2'-O-Benzoyl-6-O-propargyl-11-amino-3-descladinosyl-11-deoxy-3-oxo-15-methylerythromycin A 11,12-cyclic carbamate (40 mg), tris(dibenzylideneacetone) dipalladium(0)-chloroform adduct (14 mg), tri-o-tolylphosphine (17 mg), copper iodide, and 3-bromoquinoline (72 μl, 0.53 mmol, 10 eq) are placed in a round-bottom flask which is flushed with N$_2$. Degassed acetonitrile (1 mL) and freshly distilled Et$_3$N (0.015 ml, 0.11 mmol, 2.0 eq) are added. The reaction is refluxed for 63 h. The mixture is returned to ambient temperature and diluted with 40 mL of EtOAc. The solution is washed successively with 10 mL each of saturated aqueous NaHCO$_3$, water, and brine. The organic phase is dried over MgSO$_4$, filtered, and concentrated. Flash chromatography yields the desired product.

Step 2: The above product is dissolved in 1 mL of methanol, sealed, and refluxed at 80° C. for 16 h. Volatiles are removed under reduced pressure. Flash chromatography yields the desired product.

Preparation B: Formula (P): X=H, R$_a$ is —CH$_2$—CC-(3-(6-Fluoroquinolyl)

This is prepared according to the method of Preparation A, using 3-bromo-6-fluoroquinoline in place of 3-bromoquinoline.

Preparation C: Formula (I): X=H, R$_a$ is —CH$_2$—CC-(3-(6-Chloroquinolyl)

This is prepared according to the method of Preparation A, using 3-bromo-6-chloroquinoline in place of 3-bromoquinoline.

Preparation D: Formula (I): X=H, R$_a$ is —CH$_2$—CC-(4-Isoquinolyl)

This is prepared according to the method of Preparation A, using 4-bromoisoquinoline in place of 3-bromoquinoline.

Preparation E: Formula (I): X=H, R$_a$ is —CH$_2$—CC-(3-Pyridyl)

This is prepared according to the method of Preparation A, using 3-pyridine in place of 3-bromoquinoline.

Preparation F: Formula (I): X=H, R$_a$ is —CH$_2$—CC-(3-(6-Methylquinolyl)

This is prepared according to the method of Preparation A, using 3-bromo-6-methylquinoline in place of 3-bromoquinoline.

Preparation G: Formula (I): X=H, R$_a$ is —CH$_2$—CC-(3-(6-Aminoquinolyl)

This is prepared according to the method of Preparation A, using 3-bromo-6-aminoquinoline in place of 3-bromoquinoline.

Preparation H: Formula (I): X=H, R$_a$ is —CH$_2$—CC-(3-(5-Isoxazol-3-yl)thienyl)

This is prepared according to the method of Preparation A, using 5-(isoxazol-3-yl)-2-bromothiophene in place of 3-bromoquinoline.

Preparation I: Formula (1): X=H, R$_a$ is —CH$_2$—CC-(6-Quinolyl)

This is prepared according to the method of Preparation A, using 6-bromoquinoline in place of 3-bromoquinoline.

Preparation J: Formula (I): X=H, R$_a$ is —CH$_2$—CC-(3-Quinoxal-6-yl

This is prepared according to the method of Preparation A using 6-bromoquinoxaline in place of 3-bromoquinoline.

Preparation K: Formula (I): X=H, $R_a$ is —$CH_2$—CC-(5-(N-(2-Pyridyl)-2-furamidyl)

This is prepared according to the method of Preparation A, using N-(2-pyridyl) 5-bromo-2-furamide in place of 3-bromoquinoline.

Preparation AA: Formula (I): X=F, $R_a$ is —$CH_2$—CC-(3-Quinolyl)

This was prepared according to the method of Preparation A using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation BB: Formula (I): X=F, $R_a$ is —$CH_2$—CC-(3-(6-Fluoroquinolyl)

This is prepared according to the method of Preparation B using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation CC: Formula (I): X=F, $R_a$ is —$CH_2$—CC-(3-(6-Chloroquinolyl)

This is prepared according to the method of Preparation C using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-I 1-amino-3-descladinosyl-11-deoxy-3-oxo-15-methylerythromycin A 11,12-cyclic carbamate.

Preparation DD: Formula (I): X=F, $R_a$ —$CH_2$—CC-(4-Isoquinolyl)

This is prepared according to the method of Preparation D using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation EE: Formula (1): X=F, $R_a$ is —$CH_2$—CC-(3-Pyridyl)

This is prepared according to the method of Preparation E using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation FF: Formula (I): X=F, $R_a$ is —$CH_2$—CC-(3-(6-Methylquinolyl)

This is prepared according to the method of Preparation F using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation GG: Formula (I): X=F, $R_a$ is —$CH_2$—CC-(3-(6-Aminoquinolyl)

This is prepared according to the method of Preparation G using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation HH: Formula (I): X=F, $R_a$ is —$CH_2$—CC-(3-(5-Isoxazol-3-yl)thienyl)

This is prepared according to the method of Preparation H using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation II: Formula (I): X=F, $R_a$ is —$CH_2$—CC-(6-Quinolyl)

This is prepared according to the method of Preparation I using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation JJ: Formula (I): X=F, $R_a$ is —$CH_2$—CC-(3-Quinoxal-6-yl)

This is prepared according to the method of Preparation J using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Preparation KK: Formula (I): X=F, $R_a$ is —$CH_2$—CC-(5-(N-(2-Pyridyl)-2-furamidyl)

This is prepared according to the method of Preparation K using 2'-O-benzoyl-6-O-allyl-11-amino-3-descladinosyl-11-deoxy-3-oxo-2-fluoro-15-methylerythromycin A 11,12-cyclic carbamate in place of 2'-O-benzoyl-6-O-allyl-11-amino-3-descladinosyl-11-deoxy-3-oxo-15-methylerythromycin A 11,12-cyclic carbamate.

Example 18

Synthesis of 5-O-(2'-Acetyldesosaminyl)-10,11-anhydro-3,6-dideoxy-3-oxo-14-norerythronolide A Preparation A: 5-O-Desosaminyl-10,11-anhydro-6-deoxy-14-norerythronolide A A mixture of 6-deoxy-14-norerythromycins A, B, C, and D derived from fermentation (0.5 g) is dissolved in dichloromethane (6 mL) and treated with chlorotrimethylsilane (0.144 mL) and 1-trimethylsilylimidazole (0.20 mL). After 10 minutes, the reaction is treated with 1 N NaOH and is extracted three times with dichloromethane. The organic extracts are combined, washed with sat. NaCl, dried over $MgSO_4$, filtered, and evaporated to yield a foamy material. This material is dissolved in tetrahydrofuran (5 mL) and treated with 1,1'-carbonyldiimidazole (0.45 g) and sodium hydride (50 mg of a 60% dispersion in oil, washed with hexanes). The mixture is heated at 70° C. for 1 hour, then cooled and treated with 1 N NaOH and extracted three times with ethyl acetate. The organic extracts are combined, washed with sat. NaCl, dried over $MgSO_4$, filtered, and evaporated to dryness. The resulting product mixture is dissolved in ethanol (0.5 mL) and treated with 2% HCl in water (1 mL) to cleave the 3-O-glycosyl groups. The product is recovered by chromatography. Mass spectrometry reveals $[M+H]^+=559$.

Preparation B: 5-O-(2'-acetyldesosaminyl)-10,11-anhydro-6-deoxy-14-norerythronolide A A solution of 5-O-desosaminyl-10,11-anhydro-6-deoxy-14-norerythronolide A (0.5 g) in acetone (10 mL) is treated with acetic anhydride (0.10 mL) and potassium carbonate (0.15 g) at ambient temperature for 24 hours, filtered, and concentrated to dryness to yield the product. Mass spectrometry reveals $[M+H]^+=601$.

Preparation C: 5-O-(2'-acetyldesosaminyl)-10,11-anhydro-3,6-dideoxy-3-oxo-14-nor-erythronolide A A solution of 5-O-(2'-acetyldesosaminyl)-10,11-anhydro-6-deoxy-14-norerythronolide A (0.5 g) and 1-(3-dimethylaminopropyl)-3-ethylcarbodiimide hydrochloride (1.0 g) in dichloromethane (10 mL) is treated with methylsulfoxide (1.0 mL) and cooled to 5° C. A solution of pyridinium trifluoroacetate (1.0 g) in dichloromethane (10 mL) is added dropwise, and the mixture is stirred at 5° C. for 2 hours. The mixture is diluted with ethyl acetate, washed with water and saturated NaCl then dried over $MgSO_4$, filtered, and evaporated to dryness. The product is purified by chromatography. Mass spectrometry reveals $[M+H]^+$= 599.

Example 19

Synthesis of 5-O-(2'-acetyldesosaminyl)-10,11-anhydro-3,6-dideoxy-3-oxo-14,15-dehydrorerythronolide A Preparation A: 5-O-desosaminyl-10,11-anhydro-6-deoxy-14,15-dehydroerythronolide A A mixture of 6-deoxy-14,15-dehydroerythromycins A, B, C, and D derived from fermentation (0.5 g) is dissolved in dichloromethane (6 mL) and treated with chlorotrimethylsilane (0.144 mL) and 1-trimethylsilylimidazole (0.20 mL). After 10 minutes, the reaction is treated with 1 N NaOH and is extracted three times with dichloromethane. The organic extracts are combined, washed with sat. NaCl, dried over $MgSO_4$, filtered, and evaporated to yield a foamy material. This material is dissolved in tetrahydrofuran (5 mL) and treated with 1,1'-carbonyldiimidazole (0.45 g) and sodium hydride (50 mg of a 60% dispersion in oil, washed with hexanes). The mixture is heated at 70° C. for 1 hour, then cooled and treated with 1 N NaOH and extracted three times with ethyl acetate. The organic extracts are combined, washed with sat. NaCl, dried over $MgSO_4$, filtered, and evaporated to dryness. The resulting product mixture is dissolved in ethanol (0.5 mL) and treated with 2% HCl in water (1 mL) to cleave the 3-O-glycosyl groups. The product is recovered by chromatography.

Preparation B: 5-O-(2'-acetyldesosaminyl)-10,11-anhydro-6-deoxy-14,15-dehydroerythronolide A A solution of 5-O-desosaminyl-10,11-anhydro-6-deoxy-14,15-dehydroerythronolide A (0.5 g) in acetone (10 mL) is treated with acetic anhydride (0.10 mL) and potassium carbonate (0.15 g) at ambient temperature for 24 hours, filtered, and concentrated to dryness to yield the product.

Preparation C: 5-O-(2'-acetyldesosaminyl)-10.11-anhydro-3,6-dideoxy-3-oxo-14,15-dehydroerythronolide A A solution of 5-O-(2'-acetyldesosaminyl)-10,11-anhydro-6-deoxy-14,15-dehydroerythronolide A (0.5 g) and 1-(3-dimethylaminopropyl)-3-ethylcarbodiimide hydrochloride (1.0 g) in dichloromethane (10 mL) is treated with methylsulfoxide (1.0 mL) and cooled to 5° C. A solution of pyridinium trifluoroacetate (1.0 g) in dichloromethane (10 mL) is added dropwise, and the mixture is stirred at 5° C. for 2 hours. The mixture is diluted with ethyl acetate, washed with water and saturated NaCl then dried over $MgSO_4$, filtered, and evaporated to dryness. The product is purified by chromatography.

Example 20

Synthesis of 5-O-(2'-acetyldesosaminyl)-10,11-anhydro-3,6-dideoxy-3-oxo-15-methylerythronolide A The title compound was prepared in accordance with the following scheme:

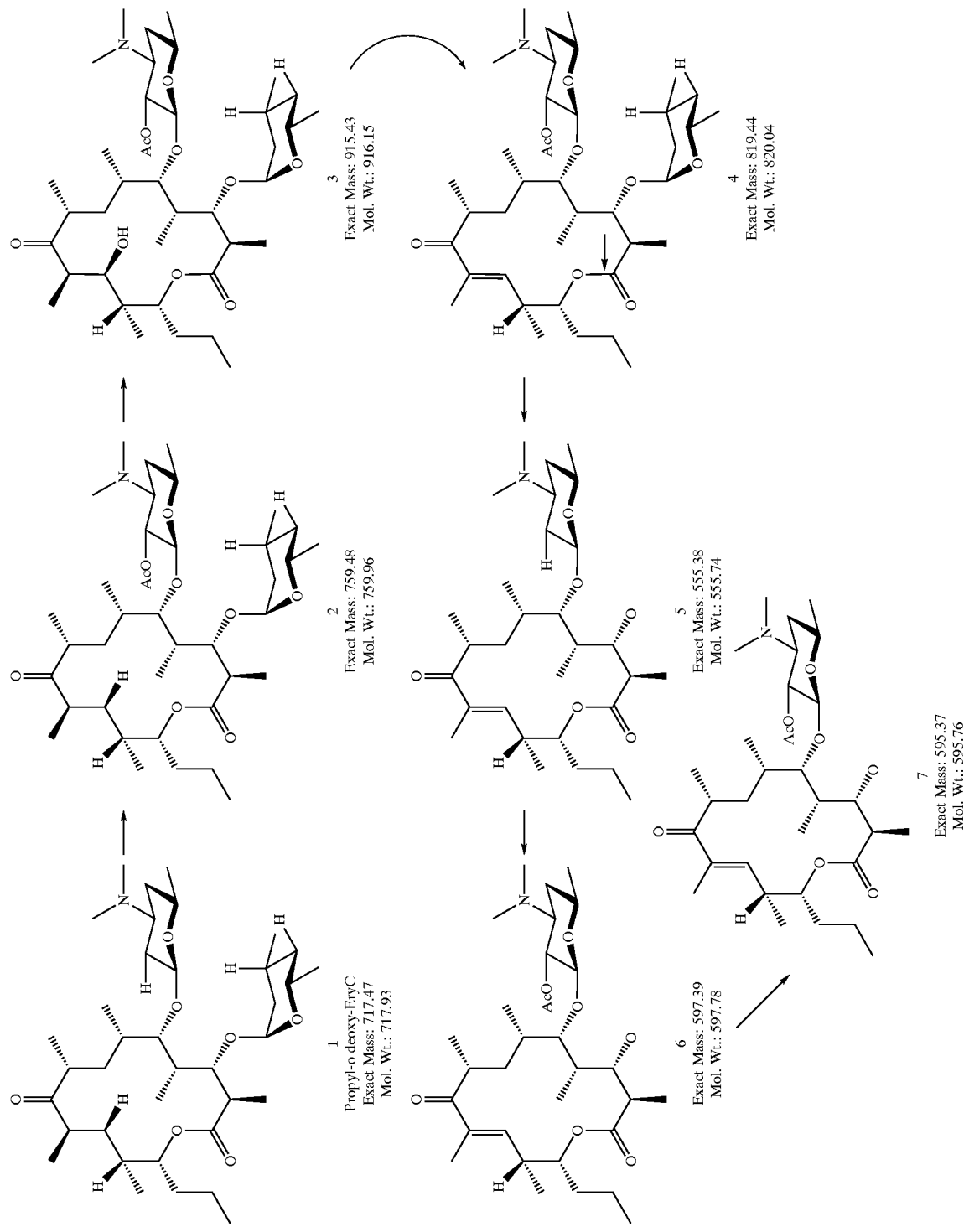
Scheme 6

Reaction 1

To a solution of compound 1 (220mg, 0.307mmol) in dichloromethane (5mL) were added potassium carbonate (50mg) and acetic anhydride (100_L, 0.9 mmol), and the reaction was stirred at room temperature for 16 hours. The solution was filtered, sodium hydroxide (1N, 25 mL) and brine (25 mL) added and the aqueous layer was extracted with ethyl acetate 6 times. The combined organic layers were dried with sodium sulfate, filtered, and the solvent removed in vacuo. The crude product 2 was carried on to the next step.

Reaction 2:

Compound 2 (crude product from reaction 1) was dissolved in pyridine (5 mL) and mesyl chloride (70_L, 0.9 mmol) was added. The reaction was stirred at −20° C. for 2 days, poured on sodium hydroxide (1N, 25 mL) and brine (25 mL) and the aqueous layer was extracted with ethyl acetate 6 times. The combined organic layers were dried with sodium sulfate, filtered, and the solvent removed in vacuo. The residue was purified by chromatography on silica gel (toluene/acetone=3:1, 1% ammonium hydroxide) to yield compound 3 (190 mg, 68% over two steps).

Reaction 3:

Compound 3 (190 mg, 0.21 mmol) was dissolved in acetone (7 mL) and DBU (63_L, 0.42 mmol) was added, and the reaction was stirred at room temperature over night. The mixture was poured on sodium hydroxide (1N, 25 mL) and brine (25 mL) and the aqueous layer was extracted with ethyl acetate 6 times. The combined organic layers were dried with sodium sulfate, filtered, and the solvent removed in vacuo. The crude product 4 was carried on to the next step.

Reaction 4:

To Compound 4 (crude product from step before) was added hydrochloric acid (30 mL, 3N) and ethanol (2 mL) and the mixture was stirred vigorously for 6 hours. Sodium hydroxide (5 mL, 10N) was added and the aqueous layer was extracted with ethyl acetate 6 times. The combined organic layers were dried with sodium sulfate, filtered, and the solvent removed in vacuo. The crude product 5 was carried on to the next step.

Reaction 5:

To Compound 6 (crude product from step before) in dichloromethane (5 mL) was added acetic anhydride (50_L, 0.45 mmol) and potassium carbonate (110 mg) and the mixture was stirred vigorously for 9 hours. The reaction was filtered, sodium hydroxide (20 mL, 1N) and brine (25 mL) were added and the aqueous layer was extracted with ethyl acetate 6 times. The combined organic layers were dried with sodium sulfate, filtered, and the solvent removed in vacuo. The residue was purified by chromatography on silica gel (toluene/acetone=3:1, 1% ammonium hydroxide) to yield compound 6 (110 mg, 89% over three steps).

Reaction 6:

Compound 6 (110 mg, 0.184 mmol) was dissolved in dichloromethane (10 mL) and Dess-Martin reagent (220 mg, 0.53 mmol) was added. The reaction was stirred at room temperature for 45 min. The reaction was quenched with Sodium hydroxide (20 mL, 1N) and brine (25 mL) and the aqueous layer was extracted with ethyl acetate 6 times. The combined organic layers were dried with sodium sulfate, filtered, and the solvent removed in vacuo. The residue was purified by chromatography on silica gel (toluene/acetone, gradient=6:1–3:1, 1% ammonium hydroxide) to yield compound 7 (94 mg, 86%)

Example 21

Synthesis of 1-(4-Amino-2-butenyl)-1H-imidazo[4,5-b]pyridine

Preparation A: (E)-N-(4-Bromo-2-butenyl)phthalimide

A solution of 1,4-dibromo-2-butene (23g, 107.9 mmol) and potassium carbonate (16.39 g, 118.7 mmol) in DMF (50 mL) at room temperature was treated with potassium phthalimide (10 g, 53.9 mmol). After 10 min., the reaction mixture was allowed to stir for 24 h, filtered, and concentrated in vacuo. The resulting oil was diluted with ethyl acetate (200 mL), washed with saturated aqueous sodium monobasic phosphate (2×100 mL), dried (MgSO$_4$), and concentrated in vacuo to afford a reddish oil. Purification by flash chromatography (0–20% ethyl acetate/hexanes) afforded 5.73 g of the title compound; mass (CI) m/z=303 (M+H).

Preparation B: 1-[(E)-4-Phthalimido-2-butenyl]-1H-imidazo[4,5-b]pyridine and 3-[(E)-4-phthalimido-2-butenyl]-3H-imidazo[4,5-b]pyridine A slurry of NaH (1.02 g, 25.4 mmol) in DMF (50 mL) at room temperature was treated with 4-azabenzimidazole (2.90 g, 24.4 mmol). After 10 min., the reaction mixture was treated with a solution of (E)-N-(4-bromo-2-butenyl) phthalimide (5.7 g, 20.3 mmol) in DMF (5 mL) over 30 min. The reaction mixture was allowed to stir for 1 h, then quenched by careful addition of water (5 mL) and the reaction mixture was concentrated in vacuo. The resulting residue was diluted with CH$_2$Cl$_2$ (50 mL), washed with brine (2×25 mL), dried (MgSO$_4$), and concentrated in vacuo to afford an off-white solid. Purification by flash chromatography (ethyl acetate containing 3% NH$_4$OH) afforded 2.08 g of 3-[(E)-4-phthalimido-2-butenyl]-3H-imidazo[4,5-b]pyridine. Changing the chromatography solvent to 5% methanol/ethyl acetate containing 5% NH$_4$OH afforded 1.66 g of 1-[(E)-4-phthalimido-2-butenyl]-1H-imidazo[4,5-b] pyridine; mass (CI) m/z=319 (M+H).

Preparation C: 1-(4-Amino-2-butenyl)-1H-imidazo[4,5-b] pyridine

A solution of 1-[(E)-4-phthalimido-2-butenyl]-1H-imidazo[4,5-b]pyridine (2.19 g, 6.87 mmol) in ethanol (100 mL) at room temperature was treated with hydrazine monohydrate (3.33 mL, 68.7 mmol). After 10 min., the reaction mixture was warmed to 60° C. for 2 h, allowed to cool to 25° C, and recooled to 0° C. in an ice bath. The resulting slurry was filtered, and the filtrate was concentrated in vacuo. Purification by flash chromatography (6% NH$_4$OH/ethanol) afforded 0.92 g of the title compound; mass (CI) m/z=211 (M+H).

Scheme 7

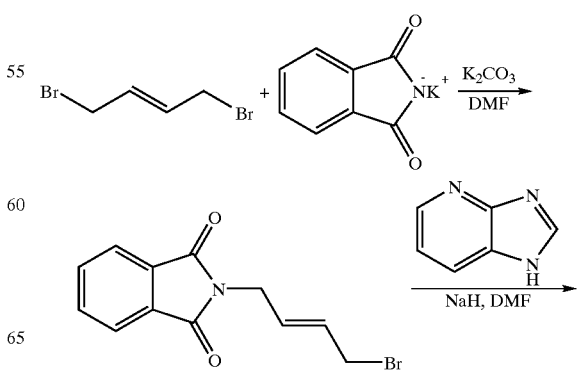

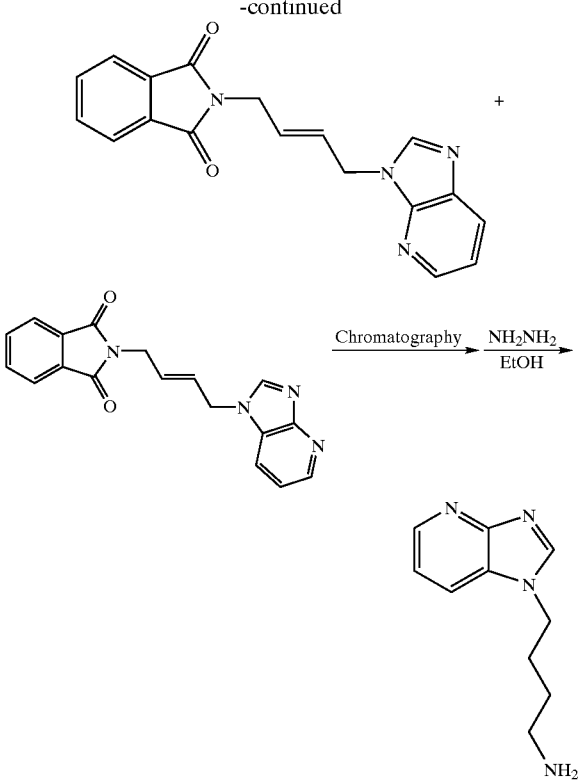

Example 22

Compound I where $R_6=OCH_3$ $R_{13}=$n-propyl. X=H, R=1H-Imidazo[4,5-b]pyridin-1-ylbutyl (Compound K in Table 1)

Step 1: Compound 19 (Scheme 2) where $R_a=CH_3$, R=n-Propyl, X=H, $R_2$=Acetyl

A solution of compound of formula 18 (Scheme 2) where $R_a=CH_3$, $R_{13}=$n-propyl, X=H, $R_2$=acetyl (625 mg, 1.00 mmol) in N,N-dimethylformamide (8 mL) at −10° C. under nitrogen is treated with sodium hydride (60 wt % in mineral oil, 80 mg, 2.00 mmol). After 30 minutes, the resulting reaction mixture is treated with 1,1'-carbonyldiimidazole (490 mg, 3.02 mmol) and the reaction mixture is allowed to stir for 2 hours at −10° C. The reaction mixture is quenched with water (30 mL) and extracted with ether (3×30 mL). The combined organic layers are washed with water (30 mL) and brine (30 mL), dried with magnesium sulfate, and concentrated in vacuo to afford 3 as an off-white foam.

Step 2: Compound I where $R_6=OCH_3$, $R_{13}=$n-Propyl, X=H, $R_a=$1H-Imidazo[4,5-b]pyridin-1-ylbutyl A solution of compound of formula 19 where $R_a=CH_3$, $R_{13}$ =n-propyl, X=H, $R_2$=acetyl (1.00 mmol) and 1H-imidazo[4,5-b]pyridin-1-ylbutylamine (570 mg, 3.00 mmol) in N,N-dimethylformamide (4 mL) is heated to 60° C. for 24 hours. The reaction mixture is allowed to cool to room temperature, diluted with water (30 mL), and extracted with ethyl acetate (3×30 mL). The combined organic layers are washed with water (2×30 mL) and brine (30 mL), dried with magnesium sulfate, filtered, and concentrated in vacuo to afford an oily residue. (Purification of 2'-acetyl I can be achieved by flash chromatography (0–5% methanol in dichloromethane containing 1–2% concentrated ammonium hydroxide) on a silica gel column.) The residue is dissolved in methanol (20 mL) and the resulting mixture is allowed to stir for 18 hours at room temperature. The reaction mixture is concentrated in vacuo and purification of I is achieved by flash chromatography on silica gel (95:5:0.5 dichloromethane/methanol/concentrated ammonium hydroxide) to provide the title compound (487 mg, 61%).

Example 23

Compound I where $R_6=OCH_3$, $R_{13}=$n-Propyl, X=F, $R_a=$1H-Imidazo[4,5-b]pyridin-1-ylbutyl (Compound O in Table 1)

The title compound was prepared as described in Example 21 except that the compound of formula 18 (Scheme 2) where $R_a=CH_3$, $R_{13}=$n-propyl, X=F, $R_2$=acetyl was substituted for the compound of formula 18 (Scheme 2) where $R_a=CH_3$, $R_{13}=$n-propyl, X=H, $R_2$ =acetyl. Yield=25%.

The following compounds can also be prepared by analogous procedures and methods as described in Example 22.

Compound of formula I where X=H, $R_6$=H, $R_{13}$=methyl, R=quinolin-4-ylbutyl

Compound of formula I where X=F, $R_6$=H, $R_{13}$=methyl, R=quinolin-4-ylbutyl

Compound of formula I where X=H, $R_6=OCH_3$, $R_{13}=$methyl, R=quinolin-4-ylbutyl (A)

Compound of formula I where X=F, $R_6=OCH_3$, $R_{13}=$methyl, R=quinolin-4-ylbutyl Compound of formula I where X=H, $R_6$=H, $R_{13}$=methyl, R=4-phenylimidazol-1-ylbutyl Compound of formula I where X F, $R_6$=H, $R_{13}$=methyl, R=4-phenylimidazol-1-ylbutyl Compound of formula I where X=H, $R_6=OCH_3$, $R_{13}=$methyl, R=4-phenylimidazol-1-ylbutyl Compound of formula I where X F, $R_6=OCH_3$, $R_{13}=$methyl, R=4-phenylimidazol-1-ylbutyl Compound of formula I where X=H, $R_6$=H, $R_{13}$=methyl, R=4-(pyridin-3-yl)imidazol-1-ylbutyl Compound of formula I where X=F, $R_6$=H, $R_{13}$=methyl, R=4-(pyridin-3-yl)imidazol-1-ylbutyl Compound of formula I where X=H, $R_6=OCH_3$, $R_{13}=$methyl, R=4-(pyridin-3-yl)imidazol-1-ylbutyl (B)

Compound of formula I where X=F, $R_6=OCH_3$, $R_{13}=$methyl, R=4-(pyridin-3-yl)imidazol-1-ylbutyl Compound of formula I where X=H, $R_6$=H, $R_{13}$=methyl, R=pyridin-4-ylbutyl Compound of formula I where X=F, $R_6$=H, $R_{13}$=methyl, R=pyridin-4-ylbutyl Compound of formula I where X=H, $R_6=OCH_3$, $R_{13}=$methyl, R=pyridin-4-ylbutyl Compound of formula I where X=F, $R_6=OCH_3$, $R_{13}=$methyl, R=pyridin-4-ylbutyl Compound of formula I where X=H, $R_6$=H, $R_{13}$=methyl, R=3H-imidazo[4,5-b]pyridin-3-ylbutyl Compound of formula I where X=F, $R_6$=H, $R_{13}$=methyl, R=3H-imidazo[4,5-b]pyridin-3-ylbutyl Compound of formula I where X=H, $R_6=OCH_3$, $R_{13}=$methyl, R=3H-imidazo[4,5-b]pyridin-3-ylbutyl (C)

Compound of formula I where X=F, $R_6=OCH_3$, $R_{13}=$methyl, R=3H-imidazo[4,5-b]pyridin-3-ylbutyl Compound of formula I where X=H, $R_6$=H, $R_{13}$=methyl, R=1H-imidazo[4,5-b]pyridin-1-ylbutyl Compound of formula I where X=F, $R_6$=H, $R_{13}$=methyl, R=1H-imidazo[4,5-b]pyridin-1-ylbutyl Compound of formula I where X=H, $R_6=OCH_3$, $R_{13}=$methyl, R=1H-imidazo[4,5-b]pyridin-1-ylbutyl (D)

Compound of formula I where X=F, $R_6=OCH_3$, $R_{13}=$methyl, R=1H-imidazo[4,5-b]pyridin-1-ylbutyl Compound of formula I where X=H, $R_6$=H, $R_{13}$=n-propyl, R=4-(pyridin-3-yl)imidazol-1-ylbutyl (P)

Compound of formula I where X=F, $R_6$=H, $R_{13}$=n-propyl, R=4-(pyridin-3-yl)imidazol-1-ylbutyl Compound of formula I where X=H, $R_6$=OCH$_3$, $R_{13}$=n-propyl, R=4-(pyridin-3-yl)imidazol-1-ylbutyl (H)

Compound of formula I where X=F, $R_6$=OCH$_3$, $R_{13}$=n-propyl, R=4-(pyridin-3-yl)imidazol-1-ylbutyl Compound of formula I where X=H, $R_6$=OCH$_3$, $R_{13}$=n-propyl, R=1H-imidazo[4,5-c]pyridin-1-ylbutyl (M)

Compound of formula I where X=F, $R_6$=OCH$_3$, $R_{13}$=n-propyl, R=1H-imidazo[4,5-c]pyridin-1-ylbutyl Compound of formula I where X=H, 16=OCH$_3$, $R_{13}$=n-propyl, R=3H-imidazo[4,5-c]pyridin-3-ylbutyl Compound of formula I where X=F, K =OCH$_3$, $R_{13}$=n-propyl, R=3H-imidazo[4,5-c]pyridin-3-ylbutyl Compound of formula I where X=H, $R_6$=OCH$_3$, $R_{13}$=n-propyl, R=purin-7-ylbutyl Compound of formula I where X=F, $R_6$=OCH$_3$, $R_{13}$=n-propyl, R=purin-7-ylbutyl Compound of formula I where X=H, $R_6$=OCH$_3$, $R_{13}$=n-propyl, R=purin-9-ylbutyl Compound of formula I where X=F, $R_6$=OCH$_3$, $R_{13}$=n-propyl, R=purin-9-ylbutyl Compound of formula I where X=H, $R_6$=OCH3, R,3=n-propyl, R=1H-imidazo[4,5-b]pyridin-1-ylbut-2-enyl (L)

Compound of formula I where X=F, $R_6$=OCH$_3$, $R_{13}$=n-propyl, R=1H-imidazo[4,5-b]pyridin-1-ylbut-2-enyl Compound of formula I where X=H, $R_6$=H, $R_{,3}$=n-propyl, R=4-(pyrimidin-5-yl)imidazol-1-ylbutyl Compound of formula I where X F, $R_6$=OCH$_3$, $R_{,3}$=n-propyl, R=4-(pyrimidin-5-yl)imidazol-1-ylbutyl Compound of formula I where X=H, $R_6$=H, $R_{13}$=n-propyl, R=1H-imidazo[4,5-b]pyridin-1-ylbutyl (Q)

Compound of formula I where X=F, $R_6$=H, $R_{,3}$=n-propyl, R=1H-imidazo[4,5-b]pyridin-1-ylbutyl Compound of formula I where X=H, $R_6$=H, $R_{13}$=n-propyl, R=3H-imidazo[4,5-b]pyridin-3-ylbutyl Compound of formula I where X=F, $R_6$=H, $R_{13}$=n-propyl, R=3H-imidazo[4,5-b]pyridin-3-ylbutyl Compound of formula I where X=H, $R_6$=OCH$_3$, $R_{,3}$=n-propyl, R=3H-imidazo[4,5-b]pyridin-3-ylbutyl (J)

Compound of formula I where X=F, $R_6$=OCH$_3$, $R_{13}$=n-propyl, R=3H-imidazo[4,5-b]pyridin-3-ylbutyl Compound of formula I where X=H, $R_6$=H, $R_{,3}$=vinyl, R=4-phenylimidazol-1-ylbutyl Compound of formula I where X=F, $R_6$=H, $R_{13}$=vinyl, R=4-phenylimidazol-1-ylbutyl Compound of formula I where X=H, $R_6$=OCH$_3$, $R_{13}$=vinyl, R=4-phenylimidazol-1-ylbutyl Compound of formula I where X=F, $R_6$=OCH$_3$, $R_{13}$=vinyl, R=4-phenylimidazol-1-ylbutyl Compound of formula I where X=H, $R_6$=H, $R_{,3}$=vinyl, R=4-pyridin-3-yl)imidazol-1-ylbutyl Compound of formula I where X=F, $R_6$=H, $R_{13}$=vinyl, R=4-(pyridin-3-yl)imidazol-1-ylbutyl Compound of formula I where X=H, $R_6$=OCH$_3$, $R_{13}$=vinyl, R=4-(pyridin-3-yl)imidazol-1-ylbutyl (E)

Compound of formula I where X=F, $R_6$=OCH$_3$, $R_{13}$=vinyl, R=4-(pyridin-3-yl)imidazol-1-ylbutyl Compound of formula I where X=H, $R_6$=H, $R_{,3}$=vinyl, R=4-(pyrimidin-5-yl)imidazol-1-ylbutyl Compound of formula I where X=F, $R_6$=H, $R_{13}$=vinyl, R=4-(pyrimidin-5-yl)imidazol-1-ylbutyl Compound of formula I where X=H, $R_6$=OCH$_3$, $R_3$=vinyl, R=4-(pyrimidin-5-yl)imidazol-1-ylbutyl Compound of formula I where X=F, $R_6$=OCH$_3$, $R_{,3}$=vinyl, R=4-(pyrimidin-5-yl)imidazol-1-ylbutyl Compound of formula I where X=H, $R_6$=H, $R_{13}$=vinyl, R=3H-imidazo[4,5-b]pyridin-3-ylbutyl Compound of formula I where X=F, $R_6$=H, $R_{,3}$=vinyl, R=3H-imidazo[4,5-b]pyridin-3-ylbutyl Compound of formula I where X=H, $R_6$=OCH$_3$, $R_{,3}$=vinyl, R=3H-imidazo[4,5-b]pyridin-3-ylbutyl (F)

Compound of formula I where X=F, $R_6$=OCH$_3$, $R_3$=vinyl, R=3H-imidazo[4,5-b]pyridin-3-ylbutyl Compound of formula I where X=H, $R_6$=H, $R_{,3}$=methyl, R=1H-imidazo[4,5-b]pyridin-1-ylbutyl Compound of formula I where X=F, $R_6$=H, $R_{13}$=methyl, R=1H-imidazo[4,5-b]pyridin-1-ylbutyl Compound of formula I where X=H, $R_6$=OCH$_3$, $R_3$=methyl, R=1H-imidazo[4,5-b]pyridin-1-ylbutyl (G)

Compound of formula I where X=F, $R_6$=OCH$_3$, $R_{,3}$=methyl, R=1H-imidazo[4,5-b]pyridin-1-ylbutyl.

Example 24

Synthesis of 2'-O-benzoyl-6-O-allyl-3-descladinosyl-3-oxo-11-deoxy-11-amino-2-fluoro-15-methylerythromycin A 11,12-Cyclic carbamate To a THF solution (0.5 ml) of 2'-O-benzoyl-6-O-allyl-3-descladinosyl-3-oxo-11-deoxy-11-amino-I 5-methylerythromycin A 11,12-cyclic carbamate (100 mg, 0.132 mmol, 1.0 eq) was added a THF solution of potassium tert-butoxide (0.3 ml, 1M, 2.3 eq.) at −78° C. The reaction mixture was then kept at −60° C. to 40° C. for 20 min., followed by introduction of N-Fluorobenzenesulfonimide (46 mg, 0.146 mmol, 1.1 eq.) in THF (0.2 ml) at −78° C. The reaction mixture was kept at −70° C. to −40° C. for 1 h before it was allowed to warm to 0° C. from −70° C. in 1.5 h. It was then diluted with EtOAc, washed with saturated aqueous NaHCO$_3$, water, and brine. The organic phase was dried over MgSO$_4$, filtered, and concentrated. Flash chromatography of the crude product (4:1 hexanes:acetone +1% Et$_3$N) yielded 76 mg (74%) of the desired product. $^{13}$C-NMR (100.6 MHz, CDCl$_3$) δ 217.5, 203 (d, J=27.6 Hz), 165.5 (d, J=23.8 Hz), 165.2, 157.5, 135.4, 132.9, 130.4, 129.8, 128.3, 118.0, 101.7, 98 (d, J=207 Hz), 83.5, 79.1, 78.6, 72.1, 69.4, 64.6, 63.5, 57.5, 44.2, 40.7, 40.4, 38.5, 37.3, 31.4, 31.3, 24.9 (d, J=24.3 Hz), 21.0, 20.7, 19.4, 17.7, 15.0, 13.9, 13.7, 13.3.

Example 25

Synthesis of 2 '-O-Benzoyl-6-O-propargyl-3-descladinosyl-3-oxo-10,11-anhydro-2-fluoro-15-methylerythromycin A A solution of 2'-O-benzoyl-6-O-propargyl-3-descladinosyl-3-oxo-10,11-anhydro-15-methyl-erythromycin A tetrahydrofuran under inert atmosphere is cooled to −78° C. and treated with 1.0 M potassium tert-butoxide in tetrahydrofuran. The mixture is stirred for 5 minutes, and a solution of N-fluorobenzenesulfonimide in tetrahydrofuran is added in three portions over 2 hours. After addition, the reaction is allowed to warm to ambient temperature and kept for an additional 5 hours. Aqueous K$_2$CO$_3$ is added, and the mixture is extracted with CH$_2$Cl$_2$. The organic extracts are combined, dried over MgSO$_4$, filtered, and evaporated. Chromatography on silica gel gives the product.

Example 26

15-(2-(3-Quinolyl)ethyl)-3-descladinosyl-3-oxo-6-O-methylerythromycin A 11,12-Cyclic Carbamate

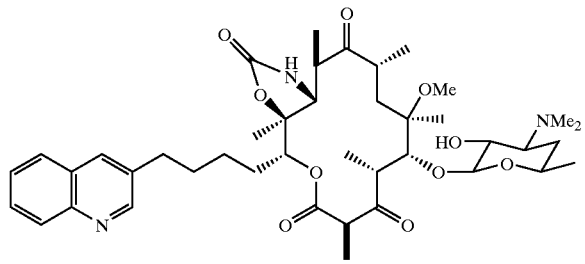

(A) 15-(2-(3-Quinolyl)ethyl)erythromycin A-9-Oxime 15-(2-(3-quinolyl)ethyl)erythromycin A (25.7 g, 28.9 mmol, 1.00 eq) is suspended in 42 mL of 2-propanol. Hydroxylamine (50 wt% in $H_2O$, 22.2 mL, 375 mmol, 13.0 eq) is added. The mixture is stirred until homogeneous. Glacial HOAc is added. The solution is stirred at 50° C. for 11 h. Saturated $NaHCO_3$ is added. The mixture is concentrated and extracted with $CHCl_3$ (4×400 mL); washed with $NaHCO_3$ and water. The combined aqueous layers are back-extracted with 400 mL $CHCl_3$. The combined organic phases are washed with brine, dried over $Na_2SO_4$, filtered, and concentrated to yield the crude material. This is carried on without further purification.

(B) 15-(2-(3-Quinolyl)ethyl)erythromycin A-9-(isopropoxycyclohexyl)oxime

The crude 15-(2-(3-quinolyl)ethyl)erythromycin A-9-oxime from above is dissolved in 72 mL of anhydrous $CH_2Cl_2$, and 1,1-diisopropoxycyclohexane (29.2 mL, 140 mmol, 4.86 eq) is added dropwise. A solution of pyridinium p-toluenesulfonate (10.5 g, 41.9 mmol, 1.45 eq) in $CH_2Cl_2$ (36 mL) is added dropwise. Dichloromethane (200 mL) is added after 15 h. The solution is washed with $NaHCO_3$ (2×100 mL) and water (100 mL). The combined aqueous phases are back-extracted with 100 mL $CH_2Cl_2$. The combined organic layers are washed with brine, dried over $MgSO_4$, filtered, and concentrated. The material is chromatographed over silica gel to give the desired product.

(C) 2',4"-Bis(O-Trimethylsilyl)-15-(2-(3-quinolyl)ethyl)erythromycin A-9-(Isopropoxycyclohexyl)oxime.

The 15-(2-(3-quinolyl)ethyl)erythromycin A-9-(isopropoxycyclohexyl)oxime (22.2 g, 21.3 mmol, 1.0 eq) is dissolved in 54 mL anhydrous $CH_2Cl_2$ and cooled in an ice/water bath. A mixture of chlorotrimethylsilane (4.05 mL, 31.9 mmol, 1.5 eq), N-(trimethylsilyl)-imidazole (7.81 mL, 53.2 mmol, 2.5 eq), and $CH_2Cl_2$ (18 mL) is added dropwise. The reaction is stirred for 15 minutes after complete addition and quenched with 600 mL EtOAc. The mixture is washed with sat. $NaHCO_3$ (2×200 mL), water (200 mL), and brine (200 mL). The organic layer is dried over $MgSO_4$, filtered, and concentrated to yield the crude product which was carried on without further purification.

(D) 2',4"-Bis(O-Trimethylsilyl)-6-O-methyl-15-(2-(3-quinolyl)ethyl)erythromycin A-9-(Isopropoxycyclohexyl)oxime Crude 2',4"-bis(O-trimethylsilyl)-15-(2-(3-quinolyl)ethyl)erythromycin A-9-(isopropoxycyclohexyl)oxime is dissolved in anhydrous tetrahydrofuran (41 mL) and cooled to 10° C. Anhydrous methylsulfoxide (41.4 mL) and methyl bromide (2.0 M in ether, 20.7 mL, 41.4 mmol, 2.0 eq) are added. A 1.0 M solution of potassium t-butoxide in THF (41.4 mL, 41.4 mmol, 2.0 eq) is diluted with anhydrous methylsulfoxide (41.4 mL). This is added to the reaction mixture at a rate of 0.5 eq/hr. The reaction is monitored by TLC (5:1 toluene:acetone). The reaction is quenched by the addition of ethyl acetate (200 mL) and sat. $NaHCO_3$ (70 mL). The mixture is transferred to a separatory funnel and diluted with 850 mL of ethyl acetate. The organic phase is washed with sat. $NaHCO_3$, water, and brine (300 mL each). The resulting emulsion is filtered through Celite. The separated organic phase is then dried over $MgSO_4$, filtered, and concentrated to give the crude product which is carried on without further purification.

(E) 6-O-Methyl-15-(2-(3-quinolyl)ethyl)erythromycin A-9-Oxime

The crude 2',4"-bis(trimethylsilyl)-6-O-methyl-15-(2-(3-quinolyl)ethyl)erythromycin A-9-(isopropoxycyclohexyl)oxime from above is dissolved in acetonitrile (110 mL). Glacial acetic acid (67 mL) diluted with water (55 mL) is added slowly. The solution is stirred 8 h. Toluene and 2-propanol are added, and the solution is concentrated. The product is then dissolved in toluene and concentrated twice to give the crude product which was carried on without further purification.

(F) 6-O-methyl-15-(2-(3-quinolyl)ethyl)erythromycin A

The crude 6-O-methyl-15-(2-(3-quinolyl)ethyl)erythromycin A-9-oxime from above and sodium hydrosulfite (23.1 g, 113 mmol, 5.63 eq) are placed in a round-bottom flask equipped with a condenser and flushed with $N_2$. Ethanol (140 mL) and water (140 mL) are added. Formic acid (3.75 mL, 95.4 mmol, 4.77 eq) is added dropwise. The mixture is stirred at 80° C. for 4.5 h. After the solution returned to room temperature, sat. $NaHCO_3$ was added. The pH is adjusted to 9–10 with 6 N NaOH. The mixture is then extracted with 3×400 mL of ethyl acetate. The combined organic phases are washed with sat. $NaHCO_3$ then water (250 mL each). The combined aqueous phases are back-extracted with ethyl acetate (400 mL). The combined organic phases are washed with brine, dried over $MgSO_4$, filtered, and concentrated to give the crude product which was carried on without further purification. Pure product can be obtained by chromatography on silica gel.

(G) 6-O-Methyl-15-(2-(3-quinolyl)ethyl)-3-descladinosylerythromycin A

The crude 6-O-methyl-15-(2-(3-quinolyl)ethyl)erythromycin A is stirred in 280 mL of 0.5 M HCl for 3 h. The pH is adjusted to 9–10 with 6 N NaOH. The precipitate is collected by vacuum filtration and washed with water. The mother liquor is extracted with 3×400 mL ethyl acetate. The combined organic phases are washed with sat. $NaHCO_3$ and water. The combined aqueous phases are back-extracted with ethyl acetate. The combined organic phases are washed with brine, dried over $MgSO_4$, filtered, and concentrated. The combined product is chromatographed over silica gel the desired product as a white solid.

(H) 2'-O-Acetyl-6-O-methyl-15-(2-(3-quinolyl)ethyl)-3-descladinosylerythromycin A 6-O-Methyl-15-(2-(3-quinolyl)ethyl)-3-descladinosyl erythromycin A (11.5 g, 15.5 mmol, 1.0 eq) is dissolved in 40 mL ethyl acetate. A solution of acetic anhydride (2.92 mL, 31.0 mmol, 2.0 eq) in ethyl acetate (35 mL) is added dropwise. The reaction is stirred for 30 min and then concentrated. The material is chromatographed over silica gel to give the desired product as a white solid.

(I) 2'-O-Acetyl-3-descladinosyl-3-oxo-6-O-methyl-15-(2-(3-quinolyl)ethyl)erythromycin A 2'-O-Acetyl-6-O-methyl-15-(2-(3-quinolyl)ethyl)-3-descladinosyl erythromycin A (10 g, 12.8 mmol, 1.0 eq) and 1-[3-(dimethylamino)propyl]-3-ethylcarbodiimide hydrochloride (16.51 g, 86.1 mmol, 6.7 eq) are combined in a round-bottom flask and flushed with $N_2$. The solids are dissolved in anhydrous $CH_2Cl_2$ (64 mL) and cooled in an ice water bath. Anhydrous DMSO (15.5 mL, 218 mmol, 17 eq) is added. A solution of pyridinium trifluoroacetate (12.14 g, 62.9 mmol, 4.9 eq) in $CH_2Cl_2$ (47 mL) is added over 3 h. The solution is diluted with 600 mL of ethyl acetate and washed with sat. $NaHCO_3$, water, and brine (200 mL each).

The organic phase is dried over MgSO$_4$, filtered, and concentrated. Chromatography over silica gel gives the desired product.

(J) 2'-O-Acetyl-3-oxo-3-descladinosyl-11-methanesulfonyl-6-O-methyl-15-(2-(3-quinolyl)ethyl)erythromycin A 2'-O-Acetyl-3-descladinosyl-3-oxo-6-O-methyl-15-(2-(3-quinolyl)ethyl)erythromycin A is dissolved in freshly distilled pyridine (35 mL) and cooled in an ice water bath. Methanesulfonyl chloride is added dropwise. The reaction is allowed to come to ambient temperature and stirred overnight. Ethyl acetate (700 mL) is added, and the solution is washed with sat. NaHCO$_3$, water, and brine (200 mL each). The organic phase is dried over MgSO$_4$, filtered, and concentrated. Chromatography over silica gel gives the desired compound.

(K) 2'-O-Acetyl-10,11-anhydro-3-descladinosyl-3-oxo-6-O-methyl-15-(2-(3-quinolyl)ethyl)erythromycin A 2'-O-Acetyl-3-oxo-3-descladinosyl-11-methanesulfonyl-6-O-methyl-15-(2-(3-quinolyl)ethyl)erythromycin A (6 g, 6.98 mmol, 1.0 eq) is dissolved in acetone (23 mL). 1,8-Diazabicyclo(5.4.0)undec-7-ene (5.22 mL, 34.9 mmol, 5.0 eq) is added dropwise. The reaction is stirred at ambient temperature for 4 h and then concentrated. Chromatography over silica gel gave the desired compound.

(L) 3-descladinosyl-3-oxo-6-O-methyl-15-(2-(3-quinolyl)ethyl)erythromycin A 11,12-Cyclic Carbamate A solution of 2'-O-Acetyl-10,11-anhydro-3-descladinosyl-3-oxo-6-O-methyl-15-(2-(3-quinolyl)ethyl)erythromycin A in dry tetrahydrofuran is added to a stirred suspension of NaH (3 eq.) in THF cooled to –10° C. To this is added a solution of carbonyldiimidazole (10 eq.) in THF/DMF (5:3), and the mixture is stirred for 2 hours. The reaction is warmed to ambient temperature and diluted with concentrated aqueous ammonia and stirred overnight. The mixture is diluted with ethyl acetate and washed with aq. NaHCO$_3$ and brine, dried over MgSO$_4$, and evaporated. Chromatography on silica gel yields the product.

Example 27

In Vitro Susceptibility Testing

Minimum inhibitory concentrations (MICs) were determined by the NCCLS broth microdilution procedure for susceptibility testing for bacteria that grow aerobically (National Committee for Clinical Laboratory Standards, 1997. Methods for dilution antimicrobial susceptibility tests for bacteria that grow aerobically, 4th ed. Approved standard. NCCLS Document M7-A4. National Committee for Clinical Laboratory Standards, Villanova, Pa.). Stock solutions were prepared on the day of the test and appropriate aliquots were added to cation adjusted Mueller-Hinton broth (CAMHB) or Haemophilus test media. Two-fold serial dilutions were prepared and added to wells in microtiter plates. Final test concentrations ranged from 16 to 0.015 pggml. Broth cultures of bacteria inoculated from growth on overnight plates for all test bacteria except *Streptococcus pneumoniae* and *Haemophilus influenzae* were incubated at 35° C. and then adjusted to the Kirby Bauer standard and diluted in CAMHB to achieve a final inoculum concentration of approximately 5×10$^5$ CFU/ml. Inocula for *S. pneumoniae* and *H. influenzae* were prepared by directly suspending colonies from an overnight plate, adjusting the turbidity and diluting as above. *S. pneumoniae* media was supplemented with 2.5% lysed horse blood. All plates were incubated in ambient air at 35° C. for 20–24 h for *S. pneumoniae* and *Haemophilus influenzae* and 16–20 h for all other bacteria.

The MIC endpoints were determined by reading the lowest concentration of test compound that completely inhibited the growth of the test bacteria.

TABLE 1

$^1$H-NMR and Mass Spectral Data for Selected Compounds (I) of the Invention

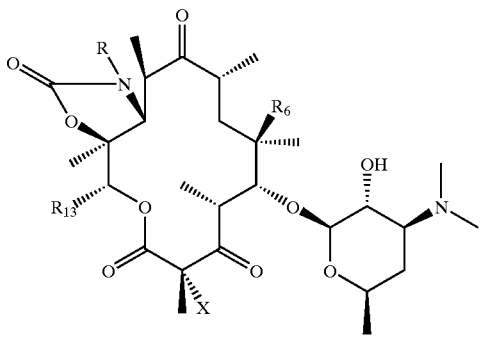

| Compound | X | R$_6$ | R$_{13}$ | R | Spectroscopic Data |
|---|---|---|---|---|---|
| A | H | OCH$_3$ | CH$_3$ | (3-quinolyl)ethyl | M + H$^+$ = 782 |

TABLE 1-continued

¹H-NMR and Mass Spectral Data for Selected Compounds (I) of the Invention

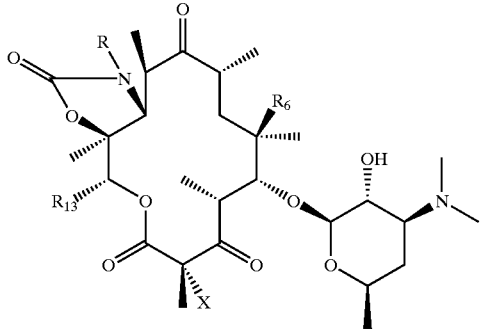

| Compound | X | $R_6$ | $R_{13}$ | R | Spectroscopic Data |
|---|---|---|---|---|---|
| B | H | $OCH_3$ | $CH_3$ | (3-pyridyl-imidazolyl-pentyl) | $M + H^+ = 810$ |
| C | H | $OCH_3$ | $CH_3$ | (imidazo[4,5-b]pyridinyl-pentyl) | ¹H-NMR(300 MHz, $CHCl_3$)δ 8.43(d, 1H), 8.15(s, 1H), 8.08(d, 1H), 7.17–7.14(m, 1H), 5.20 (m, 1H), 4.42–4.10 (m, 4H), 3.8–3.43(m, 4H), 3.38–3.0(m, 4H), 2.98–2.86(m, 2H), 2.62(s, 3H), 2.57(s, 6H), 2.1–1.10 (m, 31H) |
| D | H | $OCH_3$ | $CH_3$ | (imidazo[4,5-b]pyridinyl-pentyl) | $M + H^+ = 772$ |
| E | H | $OCH_3$ | $CH=CH_2$ | (3-pyridyl-imidazolyl-pentyl) | $M + H^+ = 798$ |

TABLE 1-continued

¹H-NMR and Mass Spectral Data for Selected Compounds (I) of the Invention

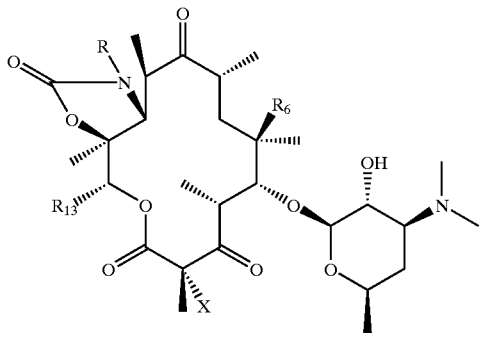

| Compound | X | R₆ | R₁₃ | R | Spectroscopic Data |
|---|---|---|---|---|---|
| F | H | OCH₃ | CH=CH₂ | (imidazopyridinyl-pentyl) | ¹H-NMR(300 MHz, CHCl₃)δ 8.43(d, 1H), 8.15(s, 1H), 8.08(d, 1H), 7.17–7.14(m, 1H), 6.05–5.93(m, 1H), 5.45–5.30(m, 2H), 5.39(s, 1H), 5.20(s, 1H), 4.42–4.10(m, 4H), 3.8–3.43(m, 4H), 3.38–3.0(m, 4H), 2.98–2.86(m, 2H), 2.62(s, 3H), 2.57(s, 6H), 2.1–1.10(m, 26H), 0.95(d, 3H) |
| G | H | OCH₃ | CH=CH₂ | (imidazopyridinyl-pentyl) | ¹H-NMR(300 MHz, CHCl₃)δ 8.59(d, 1H), 8.15(s, 1H), 7.76(d, 1H), 7.17–7.14(m, 1H), 6.11–5.93(m, 1H), 5.45–5.30(m, 2H), 5.22(s, 1H), 5.17(s, 1H), 4.30–4.10(m, 4H), 3.8–3.43(m, 4H), 3.28–3.12(m, 4H), 2.98–2.86(m, 2H), 2.62 (s, 3H), 2.48–2.39(m, 1H), 2.38(s, 6H), 2.1–1.10(m, 26H), 1.1(d, 3H) |
| H | H | OCH₃ | CH₂CH₂CH₃ | (pyridyl-imidazolyl-pentyl) | M + H⁺ = 826 |
| J | H | OCH₃ | CH₂CH₂CH₃ | (imidazopyridinyl-pentyl) | M + H⁺ = 800 |

TABLE 1-continued

¹H-NMR and Mass Spectral Data for Selected Compounds (I) of the Invention

| Compound | X | $R_6$ | $R_{13}$ | R | Spectroscopic Data |
|---|---|---|---|---|---|
| K | H | $OCH_3$ | $CH_2CH_2CH_3$ | imidazopyridine-(CH₂)₄- | $M + H^+ = 800$ |
| L | H | $OCH_3$ | $CH_2CH_2CH_3$ | imidazopyridine-CH₂-CH=CH-CH₂- | ¹H-NMR(300 MHz, CHCl₃)δ 8.59(d, 1H), 8.09(s, 1H), 7.78(d, 1H), 7.17–7.14(m, 1H), 5.95–5.71(m, 2H), 4.95(d, 1H), 4.81(d, 1H), 4.42–4.10(m, 4H), 3.62–3.43(m, 2H), 3.32–3.0(m, 4H), 2.57(s, 3H), 2.48–2.39 (m, 1H), 2.30(s, 6H), 1.72–1.10(m, 30H), 0.95(d, 3H), 0.85(t, 2H) |
| M | H | $OCH_3$ | $CH_2CH_2CH_3$ | imidazopyridine-(CH₂)₄- | ¹H-NMR(300 MHz, CHCl₃)δ 9.20(s, 1H), 8.43(d, 1H), 8.02(s, 1H), 7.41(d, 1H), 5.15(m, 1H), 4.42–4.10(m, 4H), 3.82–3.42(m, 5H), 3.32–3.02(m, 4H), 2.57(s, 3H), 2.48–2.39(m, 1H), 2.30(s, 6H), 2.10–0.95(m, 39H) |
| N | H | $OCH_3$ | $CH_2CH_2CH_3$ | purine-(CH₂)₄- | ¹H-NMR(300 MHz, CHCl₃)δ 9.20(s, 1H), 9.01(s, 1H), 8.17(s, 1H), 4.95(d, 1H), 4.42–4.10(m, 4H), 3.82–3.42(m, 5H), 3.32–3.02(m, 4H), 2.57(s, 3H), 2.48–2.39(m, 1H), 2.30(s, 6H), 2.10–0.95(m, 24H), 0.95(d, 3H), 0.85(t, 2H) |

TABLE 1-continued

¹H-NMR and Mass Spectral Data for Selected Compounds (I) of the Invention

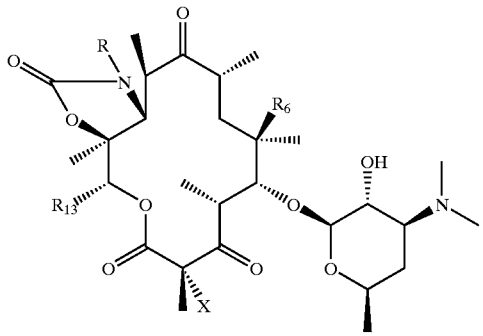

| Compound | X | R₆ | R₁₃ | R | Spectroscopic Data |
|---|---|---|---|---|---|
| O | F | OCH₃ | CH₂CH₂CH₃ | (imidazopyridine-CH₂CH₂CH₂CH₂CH₂-) | $^{13}$C-NMR(75 MHz, CDCl₃)δ 216.6, 202.7(d, J=28.0 Hz), 166.5(d, J=23.0Hz), 157.3, 156.3, 145.0, 144.8, 126.0, 118.0, 118.0, 104.3, 97.8(d, J=204.9Hz), 82.1, 80.7, 78.6, 70.4, 69.7, 65.8, 60.7, 53.5, 49.2, 45.0, 44.5, 42.4, 40.9, 40.2, 39.5, 39.2, 30.9, 28.2, 27.3, 25.2(d, J=22.3 Hz), 24.4, 21.2, 19.8, 19.1, 17.9, 15.0, 14.7, 13.7, 13.6. M + H⁺ = 818 |
| P | H | H | CH₂CH₂CH₃ | (pyridyl-imidazole-CH₂CH₂CH₂CH₂CH₂-) | ¹H-NMR(300 MHz, CHCl₃)δ 9.10(s, 1H), 8.52(s, 1H), 8.17(d, 1H), 7.60(s, 1H), 6.42(s, 1H), 4.42–4.21(m, 1H), 4.12–3.95(m, 2H), 3.65–0.85(m, 58H) |
| Q | H | H | CH₂CH₂CH₃ | (imidazopyridine-CH₂CH₂CH₂CH₂CH₂-) | M + H⁺ = 770 |

TABLE 2

In Vitro Susceptibility (MIC in µg/ml)

| Compound | E. coli OC2605 | S. aureus ATCC29213 | E. faecalis ATCC29212 | S. pneumoniae ATCC49619 | H. influenzae OC4883 |
|---|---|---|---|---|---|
| Erythromycin | >16 | 0.5 | 1 | 0.06 | 1 |
| A | >16 | 0.25 | 0.12 | 0.03 | 8 |
| B | >16 | 0.5 | 0.25 | 0.03 | 16 |
| C | >16 | 2 | 0.5 | 0.12 | >16 |

TABLE 2-continued

| | In Vitro Susceptibility (MIC in μg/ml) | | | | |
|---|---|---|---|---|---|
| | Microorganism | | | | |
| Compound | E. coli OC2605 | S. aureus ATCC29213 | E. faecalis ATCC29212 | S. pneumoniae ATCC49619 | H. influenzae OC4883 |
| D | >16 | 1 | 0.12 | 0.03 | 8 |
| E | >16 | 0.5 | 0.12 | 0.03 | 8 |
| F | >16 | 0.5 | 0.12 | 0.06 | 8 |
| H | >16 | 1 | 0.25 | 0.06 | 8 |
| J | >16 | 0.5 | 0.25 | 0.06 | 8 |
| K | 4 | 0.25 | 0.06 | ≦0.015 | 2 |
| L | 4 | 0.25 | 0.12 | 0.03 | 4 |
| M | 8 | 0.25 | 0.06 | 0.03 | 1 |
| N | 16 | 0.5 | 0.12 | 0.06 | 4 |
| O | 2 | 0.12 | 0.03 | ≦0.015 | ≦0.25 |
| P | >16 | >16 | 16 | 2 | >16 |
| Q | >16 | 8 | 1 | 0.25 | >16 |
| Compound of formula I wherein $R_6$ = O-3-(quinolin-3-yl)prop-2-enyl, $R_{13}$ = n-propyl, X = H, R = H | 8 | 0.12 | 0.06 | ≦0.015 | 1 |
| Compound of formula I wherein $R_6$ = O-3-(6-fluoro-quinolin-3-yl)prop-2-enyl, $R_{13}$ = n-propyl, X = H, R = H | 16 | 0.12 | 0.06 | ≦0.015 | 4 |
| Compound of formula I wherein $R_6$ = O-3-(6-chloro-quinolin-3-yl)prop-2-enyl, $R_{13}$ = n-propyl, X = H, R = H | 16 | 0.25 | 0.12 | 0.03 | 8 |

We claim:

1. A compound of the formula I:

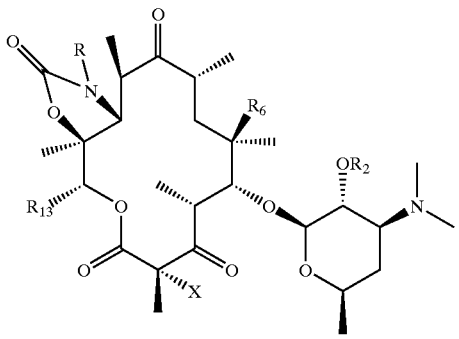

wherein:
X is H, F, Cl, Br, or I;
$R_2$ is selected from the group consisting of H, —COCH$_3$ and —COPhenyl;
$R_6$ is —O—$R_a$ where $R_a$ is substituted or unsubstituted alkenyl ($C_2$–$C_{10}$), or substituted or unsubstituted alkynyl($C_2$–$C_{10}$);
$R_{13}$ is selected from the group consisting of H, ($C_1$–$C_8$) alkyl, 1-alkenyl ($C_2$–$C_8$), 1-alkynyl ($C_2$–$C_8$), substituted ($C_1$–$C_8$)alkyl, and —CH$_2$—R" where R" is selected from the group consisting of H, ($C_1$–$C_8$) alkyl, substituted ($C_1$–$C_8$)alkyl, cycloalkyl, alkenyl ($C_2$–$C_8$), alkynyl ($C_2$–$C_8$), aryl, substituted-aryl, ($C_1$–$C_8$) alkylaryl, heterocyclo, and substituted heterocyclo;
provided that $R_{13}$ can not be ethyl;
R is selected from the group consisting of H, aryl, substituted-aryl, heterocyclo, substituted-heterocyclo, cycloalkyl, $C_1$–$C_8$-alkyl and $C_1$–$C_8$-alkenyl optionally substituted with one or more substituents selected from the group consisting of aryl, substituted-aryl, heterocyclo, substituted-heterocyclo, hydroxy, and $C_1$–$C_6$-alkoxy;
or a pharmaceutically acceptable salt, ester or pro-drug form thereof.

2. The compound of claim 1 wherein:
X is H or F;
$R_2$ is selected from the group consisting of H, —COCH$_3$ and —COPhenyl;
$R_6$ is —O—$R_a$ where $R_a$ is substituted or unsubstituted alkenyl ($C_2$–$C_{10}$), or substituted or unsubstituted alkynyl($C_2$–$C_{10}$);

R₁₃ is selected from the group consisting of H, (C₁–C₈) alkyl, 1-alkenyl (C₂–C₈), 1-alkynyl (C₂–C₈), haloalkyl, and —CH₂—R″ where R″ is selected from the group consisting of H, (C₁–C₈) alkyl, haloalkyl, 1-alkenyl (C₂–C₈), 1-alkynyl (C₂–C₈), phenyl, and (C₁–C₈) alkylphenyl (such as benzyl and phenethyl);

provided that R₁₃ can not be ethyl;

R is selected from the group consisting of H, aryl, substituted-aryl, heterocyclo, substituted-heterocyclo, cycloalkyl, C₁–C₈-alkyl and C₁–C₈-alkenyl optionally substituted with one or more substituents selected from the group consisting of aryl, substituted-aryl, heterocyclo, substituted-heterocyclo, hydroxy, and C₁–C₆-alkoxy;

or a pharmaceutically acceptable salt, ester or pro-drug form thereof.

3. The compound of claim 2 wherein R is selected from the group consisting of H, phenyl and C₁–C₈-alkyl optionally substituted with one or more substituents selected from the group consisting of phenyl, hydroxy, and C₁–C₆-alkoxy and the following substituted heterocyclo groups

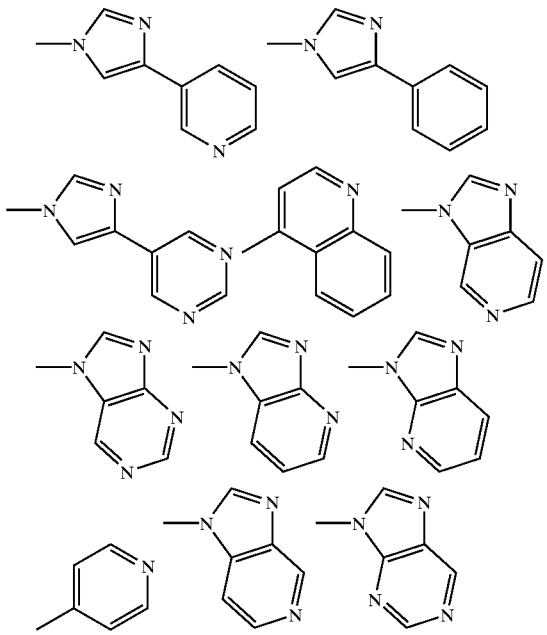

4. A compound of the formula:

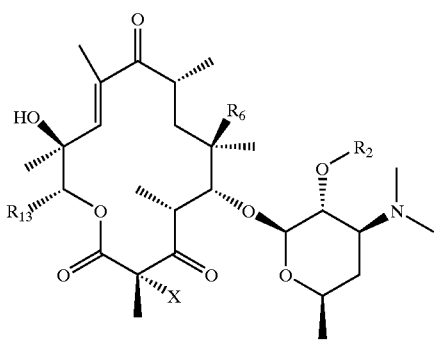

wherein;

X is H, F, Cl, Br, or I;

R₆ is —O—Rₐ where Rₐ is substituted or unsubstituted alkenyl (C₂–C₁₀), or substituted or unsubstituted alkynyl(C₂–C₁₀);

R₁₃ is selected from the group consisting of H, (C₁–C₈) alkyl, 1-alkenyl (C₂–C₈), 1-alkynyl (C₂–C₈), substituted (C₁–C₈)alkyl, and —CH₂—R″ where R″ is selected from the group consisting of H, (C₁–C₈) alkyl, substituted (C₁–C₈)alkyl, cycloalkyl, alkenyl (C₂–C₈), alkynyl (C₂–C₈), aryl, substituted-aryl, (C₁–C) alkylaryl, heterocyclo, and substituted heterocyclo;

provided that R₁₃ can not be ethyl.

5. A compound of the formula:

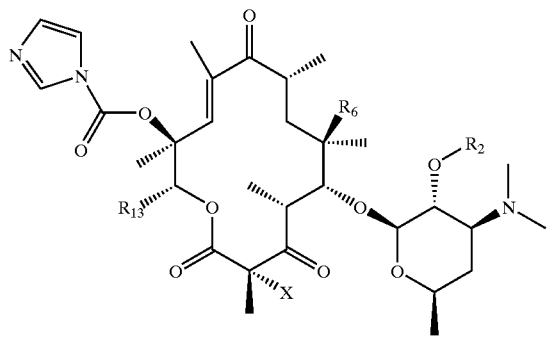

wherein:

X is H, F, Cl, Br, or I;

R₆ is —O—Rₐ where Rₐ is substituted or unsubstituted alkenyl (C₂–C₁₀), or substituted or unsubstituted alkynyl(C₂–C₁₀);

R₁₃ is selected from the group consisting of H, (C₁–C₈) alkyl, 1-alkenyl (C₂–C₆), 1-alkynyl (C₂–C₈), substituted (C₁–C₈)alkyl, and —CH₂—R″ where R″ is selected from the group consisting of H, (C₁–C₈) alkyl, substituted (C₁–C₈)alkyl, cycloalkyl, alkenyl (C₂–C₈), alkynyl (C₂–C₈), aryl, substituted-aryl, (C₁–C₈) alkylaryl, heterocyclo, and substituted heterocyclo;

provided that R₁₃ can not be ethyl; and

R₂ is hydrogen or a hydroxyl protecting group.

6. The compound of claim 1 wherein substituted heterocyclo is selected from moieties of the formula:

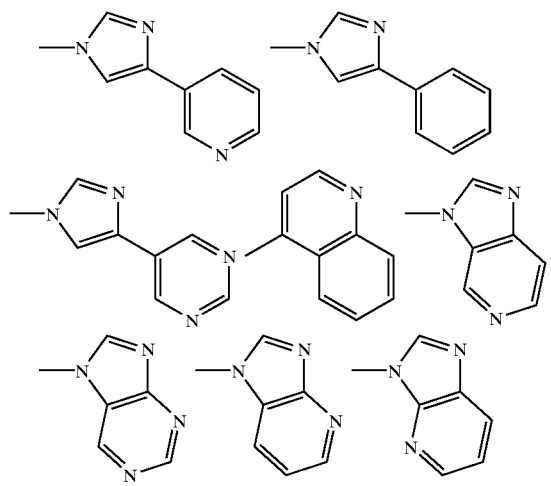

-continued

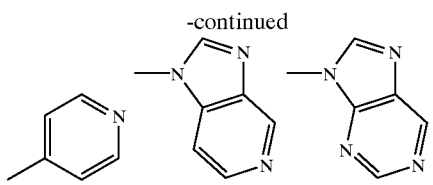

7. The compound of claim 1 wherein:
X is H or F;
$R_2$ is selected from the group consisting of H, —$COCH_3$ and —COPhenyl;
$R_6$ is —O—$R_a$ where $R_a$ is substituted or unsubstituted alkenyl ($C_2$-$C_{10}$), or substituted or unsubstituted alkynyl($C_2$-$C_{10}$);
$R_{13}$ is selected from the group consisting of H, ($C_1$-$C_8$) alkyl, 1-alkenyl ($C_2$-$C_8$), 1-alkynyl ($C_2$-$C_8$), haloalkyl, and —$CH_2$—R" where R" is selected from the group consisting of H, ($C_1$-$C_8$) alkyl, haloalkyl, 1-alkenyl ($C_2$-$C_8$), 1-alkynyl ($C_2$-$C_8$), phenyl, and ($C_1$-$C_8$) lkylphenyl;
provided that $R_{13}$ can not be ethyl;
R is H;
or a pharmaceutically acceptable salt, ester or pro-drug form thereof.

8. The compound of claim 1 wherein:
X is H, F, Cl, Br, or I;
$R_2$ is selected from the group consisting of H, —$COCH_3$ and —COPhenyl;
$R_6$ is —O—$R_a$ where $R_a$ is optionally substituted 3-(quinolin-3-yl)prop-2-enyl, optionally substituted 3-(quinolin-3-yl)prop-2-ynyl, optionally substituted 3-(quinolin-6-yl)prop-2-enyl, optionally substituted 3-(quinolin-6-yl)prop-2-ynyl, optionally substituted 3-(quinolin-7-yl)prop-2-enyl, optionally substituted 3-phenylprop-2-enyl, optionally substituted 3-(naphth-1-yl)prop-2-enyl, optionally substituted 3-(naphth-1-yl)prop-2-ynyl, optionally substituted 3-(naphth-2-yl)prop-2-enyl, optionally substituted 3-(naphth-2-yl) prop-2-ynyl, optionally substituted 5-phenylpent-4-en-2-ynyl, optionally substituted 3-(fur-2-yl)prop-2-ynyl, optionally substituted 3-(thien-2-yl)prop-2-enyl, optionally substituted 3-(carbazol-3-yl)prop-2-enyl, or optionally substituted 3-(quinoxalin-6-yl)prop-2-enyl;
$R_{13}$ is selected from the group consisting of H, ($C_1$-$C_8$) alkyl, 1-alkenyl ($C_2$-$C_8$), 1-alkynyl ($C_2$-$C_8$), substituted ($C_1$-$C_8$)alkyl, and —$CH_2$—R" where R" is selected from the group consisting of H, ($C_1$-$C_8$) alkyl, substituted ($C_1$-$C_8$)alkyl, cycloalkyl, alkenyl ($C_2$-$C_8$), alkynyl ($C_2$-$C_8$), aryl, substituted-aryl, ($C_1$-$C_8$) alkylaryl, heterocyclo, and substituted heterocyclo;
provided that $R_{13}$ can not be ethyl;
R is selected from the group consisting of H, aryl, substituted-aryl, heterocyclo, substituted-heterocyclo, cycloalkyl, $C_1$-$C_8$-alkyl and $C_1$-$C_8$-alkenyl optionally substituted with one or more substituents selected from the group of aryl, substituted-aryl, heterocyclo, substituted-heterocyclo, hydroxy, and $C_1$-$C_6$-alkoxy;
or a pharmaceutically acceptable salt, ester or pro-drug form thereof.

9. A pharmaceutical composition for treating bacterial infections comprising an effective amount of a compound of claim 1 in association with a pharmaceutically acceptable carrier.

10. A method of treating bacterial infections in mammals by administering to such mammal suffering from such infection a therapeutically acceptable amount of a compound of claim 1.

11. The compound of claim 1, wherein $R_{13}$ is propyl.

12. The compound of claim 1, wherein $RI_3$ is propyl and R is H.

13. The compound of claim 1, wherein $R_{13}$ is propyl and $R_6$ is $OCH_2CH=CH_2$.

14. A compound of formula I:

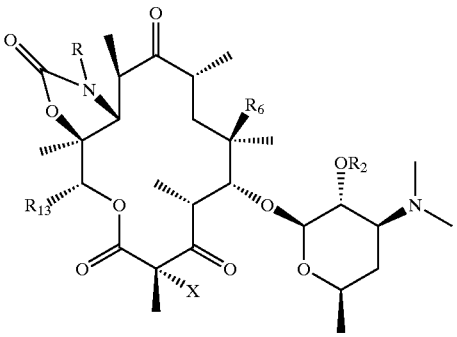

wherein:
X is H or halide;
R is H;
$R_2$ is H, —$COCH_3$ and —COPhenyl;
$R_6$ is —O-alkenylheterocyclo or —O-alkynylheterocyclo; and,
$R_{13}$ is propyl.

15. The compound as in claim 14 of the formula

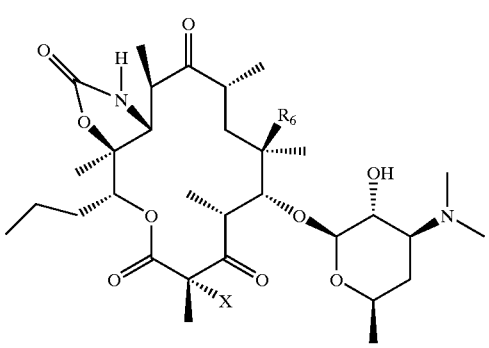

wherein X is H or F and $R_6$ is —O-propargylheterocyclo.

16. The compound as in claim 15 wherein $R_6$ is selected from:

—$OCH_2CC$-(3-quinolyl); —$OCH_2CC$-(4-quinolyl); —$OCH_2CC$- (5-quinolyl); —$OCH_2CC$-(3-(6-fluoroquinolyl)); —$OCH_2CC$-(3-(6-chloroquinolyl)); —$OCH_2CC$-(4-isoquinolyl); —$OCH_2CC$-(3-pyridyl); —$OCH_2CC$-(3-(6-methylquinolyl)); —$OCH_2CC$-(3-(6-aminoquinolyl)); —$OCH_2CC$-(3-(6-quinolyl)); —$OCH_2CC$-(3-quinoxal-6-yl); —$OCH_2CC$-(4-benzoxazolyl); —$OCH_2CC$-(7-benzimidazolyl); and —$OCH_2CC$-(5-(N-(2-pyridyl)-2-furamidyl).

17. The compound as in claim 14 of the formula

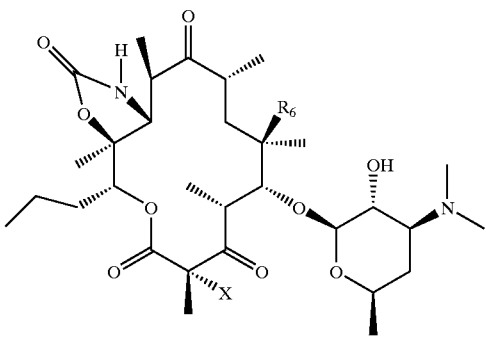

wherein X is H or F and R_6 is —O-allylheterocyclo.

18. The compound as in claim 17 wherein R_6 is selected from:

—OCH_2CH=CH-(3-quinolyl); —OCH_2CH=CH-(4-quinolyl); —OCH_2CH=CH-(5-quinolyl); —OCH_2CH=CH-(3-(6-fluoroquinolyl)); —OCH_2CH=CH-(3-(6-chloroquinolyl)); —OCH_2CH=CH-(4-isoquinolyl); —OCH_2CH=CH-(3-pyridyl); —OCH_2CH=CH-(3-(6-methylquinolyl)); —OCH_2CH=CH-(3-(6-aminoquinolyl)); —OCH_2CH=CH-(3-(6-quinolyl)); —OCH_2CH=CH-(3-quinoxal-6-yl); —OCH_2CH=CH-(4-benzoxazolyl); —OCH_2CH=CH-(7-benzimidazolyl); and —OCH_2CH=CH-(5-(N-(2-pyridyl)-2-furamidyl).

19. The compound of claim 18 wherein X is H and R_6 is —OCH_2CH=CH-(3-quinolyl).

20. The compound of claim 19 wherein X is F and R_6 is —OCH_2CH=CH-(3-quinolyl).

21. The compound of claim 18 wherein X is H and R_6 is —OCH_2CH=CH-(3-(6-quinolyl)).

22. The compound of claim 18 wherein X is F and R_6 is —OCH_2CH=CH-(3-(6-quinolyl)).

23. The compound of claim 18 wherein X is H and R_6 is —OCH_2CH=CH-(3-quinoxal-6-yl).

24. The compound of claim 18 wherein X is F and R_6 is —OCH_2CH=CH-(3-quinoxal-6-yl).

25. The compound of claim 18 wherein X is H and R_6 is —OCH_2CH=CH-(3-(6-fluoroquinolyl)).

26. The compound of claim 18 wherein X is F and R_6 is —OCH_2CH=CH-(3-(6-fluoroquinolyl)).

27. The compound of claim 18 wherein X is H and R_6 is —OCH_2CH=CH-(3-(6-methylquinolyl)).

28. The compound of claim 18 wherein X is F and R_6 is —OCH_2CH=CH-(3-(6-methylquinolyl)).

* * * * *